(12) United States Patent
Macnamara et al.

(10) Patent No.: US 11,733,542 B2
(45) Date of Patent: *Aug. 22, 2023

(54) LIGHT FIELD PROCESSOR SYSTEM

(71) Applicant: Magic Leap, Inc., Plantation, FL (US)

(72) Inventors: John Graham Macnamara, Plantation, FL (US); Nicole Elizabeth Samec, Ft. Lauderdale, FL (US); Nastasja U. Robaina, Coconut Grove, FL (US); Eric Baerenrodt, Milford, NH (US); Christopher M. Harrises, Nashua, NH (US)

(73) Assignee: Magic Leap, Inc., Plantation, FL (US)

( * ) Notice: Subject to any disclaimer, the term of this patent is extended or adjusted under 35 U.S.C. 154(b) by 60 days.

This patent is subject to a terminal disclaimer.

(21) Appl. No.: 17/229,669

(22) Filed: Apr. 13, 2021

(65) Prior Publication Data
US 2021/0231973 A1    Jul. 29, 2021

Related U.S. Application Data

(63) Continuation of application No. 16/563,750, filed on Sep. 6, 2019, now Pat. No. 11,048,101, which is a
(Continued)

(51) Int. Cl.
*G02C 7/02* (2006.01)
*G02C 11/00* (2006.01)
(Continued)

(52) U.S. Cl.
CPC ................ *G02C 7/027* (2013.01); *A61B 3/00* (2013.01); *A61B 3/0025* (2013.01); *A61B 3/028* (2013.01);
(Continued)

(58) Field of Classification Search
CPC .... G02C 7/027; G02C 11/10; G02C 2202/22; A61B 3/00; A61B 3/0025; A61B 3/028;
(Continued)

(56) References Cited

U.S. PATENT DOCUMENTS 6,850,221 B1   2/2005  Tickle
8,950,867 B2   2/2015  Macnamara
(Continued)

FOREIGN PATENT DOCUMENTS

CN    2082601 U      8/1991
CN    103190883 A    7/2013
(Continued)

OTHER PUBLICATIONS

US 11,009,721 B2, 05/2021, Macnamara et al. (withdrawn)
(Continued)

*Primary Examiner* — Mohammed A Hasan
(74) *Attorney, Agent, or Firm* — Tobias Intellectual Property Law, PLLC

(57) ABSTRACT

A wearable ophthalmic device is disclosed. The device may include a head-mounted light field display configured to generate a physical light field comprising a beam of light. The head-mounted light field display may direct the beam of light into a user's eye, thereby producing a retinal reflex. The device may also include a head-mounted photodetector array configured to receive the retinal reflex and to generate numerical image data. The device may also include a light field processor configured to control the light field display, to analyze the retinal reflex using the numerical image data, and to determine an optical prescription for the user's eye based on the analysis of the retinal reflex.

16 Claims, 21 Drawing Sheets

Related U.S. Application Data continuation of application No. 15/658,262, filed on Jul. 24, 2017, now Pat. No. 10,451,895.

(60) Provisional application No. 62/440,286, filed on Dec. 29, 2016, provisional application No. 62/366,524, filed on Jul. 25, 2016.

(51) Int. Cl.

| | |
|---|---|
| *G02B 27/01* | (2006.01) |
| *A61B 3/14* | (2006.01) |
| *A61B 3/10* | (2006.01) |
| *A61B 3/13* | (2006.01) |
| *G06F 1/14* | (2006.01) |
| *G06F 1/16* | (2006.01) |
| *G06F 3/01* | (2006.01) |
| *A61B 3/00* | (2006.01) |
| *A61B 3/028* | (2006.01) |
| *G06T 13/40* | (2011.01) |

(52) U.S. Cl.
CPC ............ *A61B 3/1015* (2013.01); *A61B 3/13* (2013.01); *A61B 3/14* (2013.01); *G02B 27/017* (2013.01); *G02B 27/0172* (2013.01); *G02C 11/10* (2013.01); *G06F 1/14* (2013.01); *G06F 1/163* (2013.01); *G06F 3/011* (2013.01); *G06F 3/013* (2013.01); *G06T 13/40* (2013.01); *G02B 2027/011* (2013.01); *G02B 2027/014* (2013.01); *G02B 2027/0132* (2013.01); *G02B 2027/0138* (2013.01); *G02B 2027/0178* (2013.01); *G02B 2027/0181* (2013.01); *G02C 2202/22* (2013.01)

(58) Field of Classification Search
CPC ........... A61B 3/1015; A61B 3/13; A61B 3/14; A61B 5/1116; A61B 2562/0219; G02B 27/017; G02B 27/0172; G02B 2027/011; G02B 2027/0132; G02B 2027/0138; G02B 2027/014; G02B 2027/0178; G02B 2027/0181; G02B 7/28; G06F 1/14; G06F 1/163; G06F 3/011; G06F 3/013; G06T 13/40; G16H 30/40; G16H 40/63; G16H 50/20
USPC ........................................................ 351/206
See application file for complete search history.

(56) References Cited

U.S. PATENT DOCUMENTS

| | | |
|---|---|---|
| 9,081,426 B2 | 7/2015 | Armstrong |
| 9,215,293 B2 | 12/2015 | Miller |
| 9,310,559 B2 | 4/2016 | Macnamara |
| 9,348,143 B2 | 5/2016 | Gao et al. |
| D758,367 S | 6/2016 | Natsume |
| 9,417,452 B2 | 8/2016 | Schowengerdt et al. |
| 9,470,906 B2 | 10/2016 | Kaji et al. |
| 9,547,174 B2 | 1/2017 | Gao et al. |
| 9,671,566 B2 | 6/2017 | Abovitz et al. |
| 9,740,006 B2 | 8/2017 | Gao |
| 9,791,700 B2 | 10/2017 | Schowengerdt et al. |
| 9,851,563 B2 | 12/2017 | Gao et al. |
| 9,857,591 B2 | 1/2018 | Welch et al. |
| 9,874,749 B2 | 1/2018 | Bradski |
| 10,451,895 B2 | 10/2019 | Macnamara et al. |
| 11,048,101 B2 * | 6/2021 | Macnamara ............ A61B 3/00 |
| 2006/0028436 A1 | 2/2006 | Armstrong |
| 2007/0027442 A1 | 2/2007 | Campin et al. |
| 2007/0081123 A1 | 4/2007 | Lewis |
| 2008/0309879 A1 | 12/2008 | Hirji |
| 2011/0213664 A1 | 9/2011 | Osterhout et al. |
| 2012/0002168 A1 | 1/2012 | Bonnin |
| 2012/0127062 A1 | 5/2012 | Bar-Zeev et al. |
| 2012/0162549 A1 | 6/2012 | Gao et al. |
| 2012/0212400 A1 | 8/2012 | Border et al. |
| 2012/0249956 A1 | 10/2012 | Narasimha-Iyer et al. |
| 2013/0082922 A1 | 4/2013 | Miller |
| 2013/0117377 A1 | 5/2013 | Miller |
| 2013/0125027 A1 | 5/2013 | Abovitz |
| 2013/0208234 A1 | 8/2013 | Lewis |
| 2013/0242262 A1 | 9/2013 | Lewis |
| 2014/0055746 A1 | 2/2014 | Nistico et al. |
| 2014/0055747 A1 | 2/2014 | Nistico et al. |
| 2014/0071539 A1 | 3/2014 | Gao |
| 2014/0177023 A1 | 6/2014 | Gao et al. |
| 2014/0218468 A1 | 8/2014 | Gao et al. |
| 2014/0267420 A1 | 9/2014 | Schowengerdt |
| 2014/0306866 A1 | 10/2014 | Miller et al. |
| 2014/0340390 A1 | 11/2014 | Lanman et al. |
| 2015/0016777 A1 | 1/2015 | Abovitz et al. |
| 2015/0103306 A1 | 4/2015 | Kaji et al. |
| 2015/0178923 A1 | 6/2015 | Liang et al. |
| 2015/0178939 A1 | 6/2015 | Bradski et al. |
| 2015/0205126 A1 | 7/2015 | Schowengerdt |
| 2015/0222883 A1 | 8/2015 | Welch |
| 2015/0222884 A1 | 8/2015 | Cheng |
| 2015/0235427 A1 | 8/2015 | Nobori et al. |
| 2015/0262424 A1 | 9/2015 | Tabaka et al. |
| 2015/0268415 A1 | 9/2015 | Schowengerdt et al. |
| 2015/0302652 A1 | 10/2015 | Miller et al. |
| 2015/0309263 A2 | 10/2015 | Abovitz et al. |
| 2015/0326570 A1 | 11/2015 | Publicover et al. |
| 2015/0346490 A1 | 12/2015 | Tekolste et al. |
| 2015/0346495 A1 | 12/2015 | Welch et al. |
| 2016/0011419 A1 | 1/2016 | Gao |
| 2016/0026253 A1 | 1/2016 | Bradski et al. |
| 2016/0066780 A1 * | 3/2016 | Pamplona ............ A61B 5/6898 351/246 |
| 2016/0116979 A1 | 4/2016 | Border |
| 2016/0270656 A1 * | 9/2016 | Samec ................. A61B 3/0008 |
| 2018/0136486 A1 | 5/2018 | Macnamara et al. |
| 2020/0073143 A1 | 3/2020 | Macnamara et al. |

FOREIGN PATENT DOCUMENTS

| | | |
|---|---|---|
| CN | 104434020 A | 3/2015 |
| CN | 104618710 A | 5/2015 |
| JP | 2012-513604 | 6/2012 |
| JP | 2012-513604 A | 6/2012 |
| JP | 2014-508016 | 4/2014 |
| WO | WO 2010/087366 | 8/2010 |
| WO | WO 2014/100891 | 7/2014 |
| WO | WO 2014/203440 | 12/2014 |
| WO | WO 2015/081313 | 6/2015 |
| WO | WO 2018/022521 | 2/2018 |

OTHER PUBLICATIONS

International Search Report and Written Opinion for PCT Application No. PCT/US2017/43552, dated Oct. 6, 2017.

International Preliminary Report on Patentability for PCT Application No. PCT/US2017/43552, dated Jan. 29, 2019.

Azuma, "A Survey of Augmented Reality," Teleoperators and Virtual Environments 6, 4 (Aug. 1997), pp. 355-385. https://web.archive.org/web/20010604100006/http://www.cs.unc.edu/~azuma/ARpresence.pdf.

Azuma, "Predictive Tracking for Augmented Realty," TR95-007, Department of Computer Science, UNC-Chapel Hill, NC, Feb. 1995.

Bimber, et al., "Spatial Augmented Reality—Merging Real and Virtual Worlds," 2005 https://web.media.mit.edu/~raskar/book/BimberRaskarAugmentedRealityBook.pdf.

Jacob, "Eye Tracking in Advanced Interface Design," Human-Computer Interaction Lab Naval Research Laboratory, Washington, D.C. / paper/ in Virtual Environments and Advanced Interface Design, ed. by W. Barfield and T.A. Furness, pp. 258-288, Oxford University Press, New York (1995).

(56) References Cited

OTHER PUBLICATIONS

Tanriverdi and Jacob, "Interacting With Eye Movements in Virtual Environments," Department of Electrical Engineering and Computer Science, Tufts University, Medford, MA—paper/Proc. ACM CHI 2000 Human Factors in Computing Systems Conference, pp. 265-272, Addison-Wesley/ACM Press (2000).
ARToolKit: https://web.archive.org/web/20051013062315/http://www.hitl.washington.edu:80/artoolkit/documentation/hardware.htm, archived Oct. 13, 2005.

\* cited by examiner

LIGHT FIELD PROCESSOR SYSTEM

INCORPORATION BY REFERENCE TO ANY PRIORITY APPLICATIONS

This application is a continuation of U.S. patent application Ser. No. 16/563,750, filed Sep. 6, 2019, and entitled "LIGHT FIELD PROCESSOR SYSTEM," which is a continuation of U.S. patent application Ser. No. 15/658,262, filed Jul. 24, 2017, and entitled "LIGHT FIELD PROCESSOR SYSTEM," which claims priority to U.S. Provisional Patent Application 62/366,524, filed Jul. 25, 2016, and entitled "LIGHT FIELD PROCESSOR SYSTEM," and to U.S. Provisional Patent Application 62/440,286, filed Dec. 29, 2016, and entitled "LIGHT FIELD PROCESSOR SYSTEM." The entire contents of any and all applications, including each of the foregoing applications, for which a foreign or domestic priority claim is identified in the Application Data Sheet as filed with the present application are hereby incorporated by reference under 37 CFR 1.57.

BACKGROUND

Field

This disclosure relates to various methods and systems for diagnosing, monitoring, and treating health conditions and ailments.

Related Art

Ophthalmic instruments and techniques are routinely used by clinicians to diagnose and treat eye-related ailments. An example of a traditional ophthalmic device is shown in FIG. 1. During use of the illustrated device, the patient may be positioned in a specific, seated position for the entire duration of the procedure, which typically may last anywhere from a few seconds to a few minutes.

Undesirably, ophthalmic devices tend to be large, bulky and expensive devices, and are typically used exclusively in doctor's offices. Thus, patients may be required to make an appointment with an optometrist and visit the doctor for any diagnoses or treatment to take place. This can be a deterring factor for many patients, who may delay the trip to the doctor's office for long periods of time, possibly until a condition has worsened. The worsened condition may require even more drastic therapies or procedures to address when the condition could have been more easily alleviated had the patient been timely diagnosed or treated. Furthermore, the large and bulky nature of most ophthalmic devices forces patients to be placed in an uncomfortable position, which in turn may increase risks of misdiagnoses and patient error.

Accordingly, there is a need for health systems that address one or more of the difficulties described above.

SUMMARY

In some embodiments, a wearable ophthalmic device comprises: a head-mounted light field display configured to generate a physical light field comprising a beam of light and to direct the beam of light into a user's eye, thereby producing a retinal reflex; a head-mounted photodetector array configured to receive the retinal reflex and to generate numerical image data; and a light field processor configured to control the light field display, to analyze the retinal reflex using the numerical image data, and to determine an optical prescription for the user's eye based on the analysis of the retinal reflex.

In some embodiments, a method of using a wearable ophthalmic device comprises: generating a physical light field comprising a beam of light and directing the beam of light into a user's eye using a head-mounted light field display, thereby producing a retinal reflex; receiving the retinal reflex and generating numerical image data using a head-mounted photodetector array; and controlling the light field display, analyzing the retinal reflex using the numerical image data, and determining an optical prescription for the user's eye based on the analysis of the retinal reflex using a light field processor.

BRIEF DESCRIPTION OF THE DRAWINGS

The drawings illustrate some examples of embodiments disclosed herein and do not limit the invention. It should be noted that the figures are not drawn to scale and that elements of similar structures or functions are represented by like reference numerals throughout the figures.

DETAILED DESCRIPTION

Figure 1:
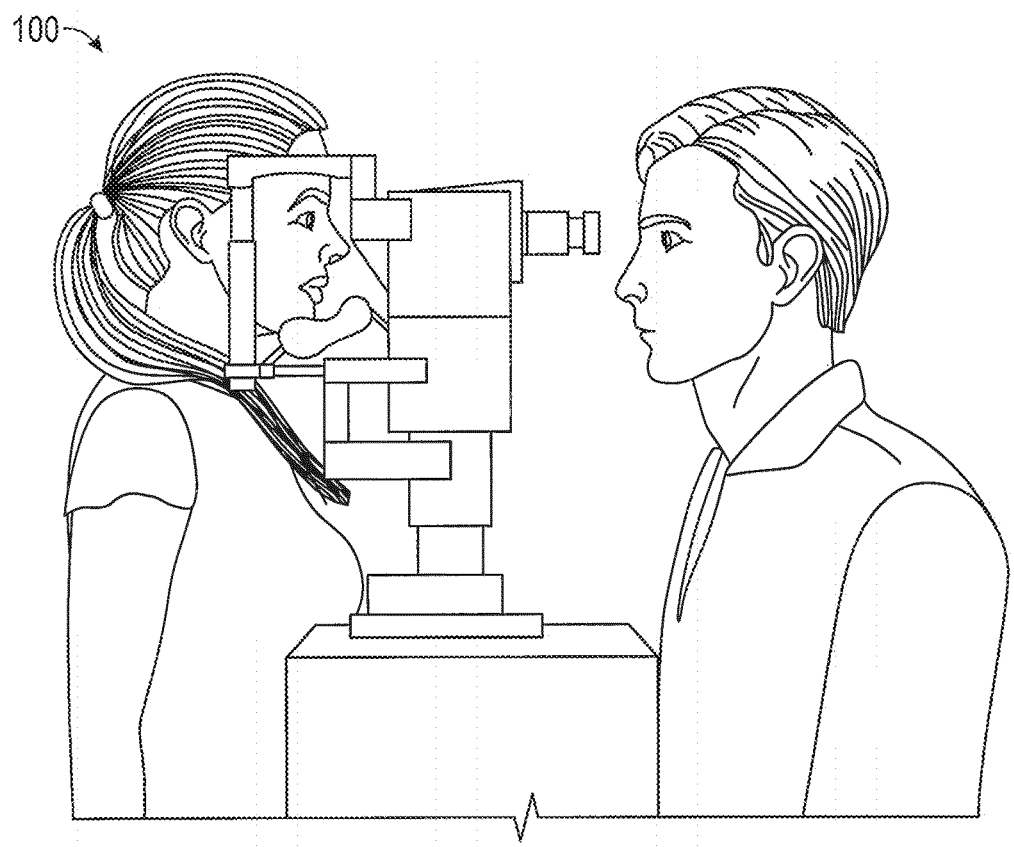
FIG. 1 illustrates a traditional ophthalmic instrument being used at a clinician's office.

Various embodiments of the invention are directed to devices, methods, systems, and articles of manufacture for implementing a user-wearable health system, which may be used for performing health-related diagnostics, monitoring, and therapeutics on the user. Various objects, features, and advantages of certain embodiments of the invention are described in the detailed description, figures, and claims, though it is not required that any single embodiment include or meet all such objects, features, and advantages.

Various embodiments will be described in detail with reference to the drawings, which are provided as illustrative examples so as to enable those skilled in the art to practice the inventions. Notably, the figures and the examples below are not meant to limit the scope of the inventions described herein. Where certain elements of the inventions may be partially or fully implemented using known components (or methods or processes), only those portions of such known components (or methods or processes) that are necessary for an understanding of the present inventions will be described, and the detailed descriptions of other portions of such known components (or methods or processes) will be omitted so as not to obscure the inventions. Further, embodiments of the inventions also encompass present and future known equivalents to the components referred to herein.

Methods and systems for diagnosing, treating, and or monitoring health ailments of patients through a user-wearable health system (e.g., a user-wearable ophthalmic device that interacts with the user's eyes) are disclosed herein. In one or more embodiments, the device may be a head-mounted system capable of performing one or more diagnostic or treatment regimens. In some other embodiments, the device may be stationary (e.g., stationary at a physician's office). In one or more embodiments, the device may be a virtual reality (VR), augmented reality (AR), and/or mixed reality (MR) system that advantageously combines many VR, AR, and/or MR techniques for health or ophthalmic purposes. VR systems create a simulated environment for a user to experience. This can be done by presenting computer-generated image data or other light signals to the user through a display. This image data creates a sensory experience which immerses the user in the simulated environment. A VR scenario typically involves presentation of only computer-generated image data rather than also including actual real-world image data. AR systems generally supplement a real-world environment with simulated elements. For example, AR systems may provide a user with a view of the surrounding real-world environment via a display. However, computer-generated image data or other light signals can also be presented on the display to enhance the real-world environment. This computer-generated image data can include elements which are contextually-related to the real-world environment. Such elements can include simulated text, images, objects, etc. The simulated elements can often times be interactive in real time. An MR scenario is a type of AR scenario and typically involves virtual objects that are integrated into, and responsive to, the natural world. For example, in an MR scenario, AR image content may be presented in a way so as to be perceived as interacting with objects in the real world.

In some other embodiments, a clinician may wear the device for the purpose of diagnosis and/or simulation and training. Various embodiments described below discuss a new paradigm of health systems in relation to AR systems, but it should be appreciated that the techniques disclosed herein may be used independently of any existing and/or known AR systems. Thus, the examples discussed below are for example purposes only and should not be read to be limited to AR systems.

As noted above, embodiments of the present inventions present a new paradigm in which user-wearable diagnostic health or health therapy systems (generally referred to herein as health systems), such as ophthalmic instruments, are worn by the patient, and may be programmed with one or more applications specific to various health-related (e.g., eye-related) ailments. In some embodiments, diagnoses and/or treatment may be provided by optical devices, mechanical structures, processing algorithms, or any combination of the above. In some other embodiments, the patient worn health system may further entail sensing and/or stimulating capabilities, for enhanced treatment or diagnostic purposes. In some embodiments, a head-worn augmented reality system may be used to provide various health-related (e.g., ophthalmic) measurements, assessments, diagnoses, or treatments.

Given that the head-mounted augmented reality display system interacts with the user's eyes, many applications may be envisioned for eye-related diagnostics and therapeutics. Further, many other applications in non-eye diagnostics and therapeutics may be similarly envisioned. Accordingly, the disclosure presented herein is not limited to diagnosing, monitoring, and/or treating the eye. Embodiments disclosed herein may also be applied to diagnose, monitor, and/or treat other areas of the user's health, including but not limited to the user's cardiovascular and neurological health.

Many embodiments of the health system will be discussed in relation to various eye-related and other ailments. Prior to delving into various embodiments of the health system, the biological mechanisms of the human eye will be briefly discussed below to provide context to common ailments that may affect patients.

Figure 2:
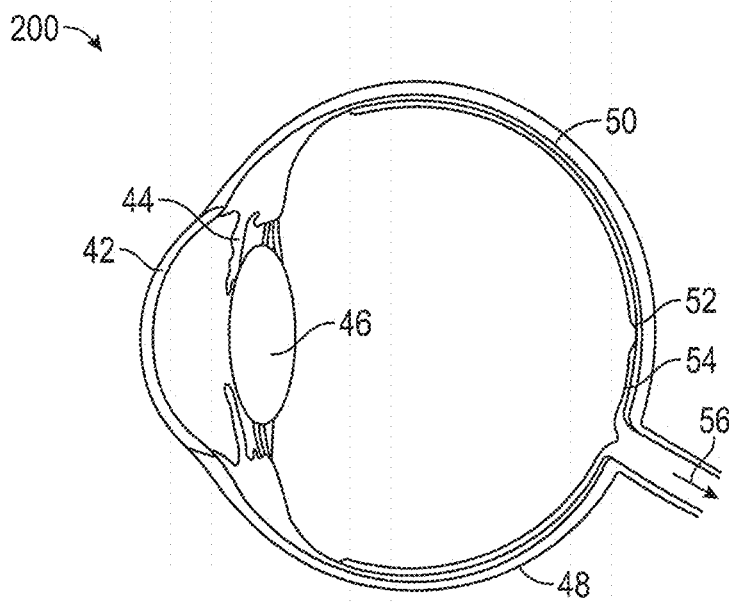
FIG. 2 illustrates a cross-section of a human eye.

With reference to FIG. 2, a simplified cross-sectional view of a human eye is depicted featuring a cornea 42, iris 44, lens—or "crystalline lens" 46, sclera 48, choroid layer 50, macula 52, retina 54, and optic nerve pathway 56 to the brain. The macula is the center of the retina, which is utilized to see moderate detail. At the center of the macula is a portion of the retina that is referred to as the "fovea," which is utilized for seeing the finest details, and which contains more photoreceptors (approximately 120 cones per visual degree) than any other portion of the retina. The human visual system is not a passive sensor type of system; it is configured to actively scan the environment. In a manner somewhat akin to use of a flatbed scanner to capture an image, or use of a finger to read Braille from paper, the photoreceptors of the eye fire in response to changes in stimulation, rather than constantly responding to a constant state of stimulation. Thus, motion is required to present photoreceptor information to the brain. Indeed, experiments with substances such as cobra venom, which has been utilized to paralyze the muscles of the eye, have shown that a human subject will experience blindness if positioned with his eyes open, viewing a static scene with venom-induced paralysis of the eyes. In other words, without changes in stimulation, the photoreceptors do not provide input to the brain and blindness is experienced. It is believed that this is at least one reason that the eyes of normal humans have been observed to move back and forth, or dither, in side-to-side motion in what are called "microsaccades."

As noted above, the fovea of the retina contains the greatest density of photoreceptors, and while humans typically have the perception that they have high-resolution visualization capabilities throughout their field of view, they generally actually have only a small high-resolution center that is swept around, along with a persistent memory of the high-resolution information recently captured with the fovea. In a somewhat similar manner, the focal distance control mechanism of the eye (ciliary muscles operatively coupled to the crystalline lens in a manner wherein ciliary relaxation causes taut ciliary connective fibers to flatten out the lens for longer focal lengths used to view at greater distances, while ciliary contraction causes loose ciliary connective fibers, which allow the lens to assume a more rounded geometry for shorter focal lengths used to view at shorter distances) dithers back and forth by approximately ¼ to ½ diopter to cyclically induce a small amount of what is called "dioptric blur" on both the close side and far side of the targeted focal length. This is utilized by the accommodation control functionality of the brain as cyclical negative feedback that helps to constantly correct accommodation and keep the retinal image of a fixated object approximately in focus.

The visualization center of the brain also gains valuable perception information from the motion of both eyes and components thereof relative to each other. Vergence movements (i.e., rolling movements of the pupils toward or away from each other to converge the lines of sight of the eyes to fixate upon an object) of the two eyes relative to each other are closely associated with focusing (or "accommodation") of the lenses of the eyes. Under normal conditions, changing the focus of the lenses of the eyes, or accommodating the eyes, to focus upon an object at a different distance will automatically cause a matching change in vergence to the same distance, under a relationship known as the "accommodation-vergence reflex." Likewise, a change in vergence will trigger a matching change in accommodation, under normal conditions. Working against this reflex, as do some conventional stereoscopic AR or VR configurations, is known to produce eye fatigue, headaches, or other forms of discomfort in users.

Movement of the head, which houses the eyes, also has a key impact upon visualization of objects. Humans move their heads to visualize the world around them; they often are in a fairly constant state of repositioning and reorienting the head relative to an object of interest. Further, most people prefer to move their heads when their eye gaze needs to move more than about 20 degrees off center to focus on a particular object (i.e., people do not typically like to look at things "from the corner of the eye"). Humans also typically scan or move their heads in relation to sounds to improve audio signal capture and utilize the geometry of the ears relative to the head. The human visual system gains powerful depth cues from what is called "head motion parallax," which is related to the relative motion of objects at different distances as a function of head motion and eye vergence distance (i.e., if a person moves his head from side to side and maintains fixation on an object, items farther out from that object will appear to move in the same direction as the head, while items in front of that object will appear to move opposite the head motion; these are very salient cues for where things are located spatially in the environment relative to the person—perhaps as powerful as stereopsis). Head motion also is utilized to look around objects, of course.

Further, head and eye motion are coordinated with something called the "vestibulo-ocular reflex," which stabilizes image information relative to the retina during head rotations, thus keeping the object image information approximately centered on the retina. In response to a head rotation, the eyes are reflexively and proportionately rotated in the opposite direction to maintain stable fixation on an object. As a result of this compensatory relationship, many humans can read a book while shaking their head back and forth. (Interestingly, the same generally is not true if the book is panned back and forth at the same speed with the head approximately stationary—the person is not likely to be able to read the moving book. The vestibulo-ocular reflex is one of head and eye motion coordination, generally not developed for hand motion.) This paradigm may be significant for patient-worn health systems because head motions of the user may be associated relatively directly with eye motions, and the system preferably will be ready to work with this relationship. Thus, when designing a patient-worn or stationary display-based health system, characteristics, and sometimes limitations, of the human eye are preferably taken into account to provide meaningful virtual content that works with the eye's natural mechanisms rather than stressing them. Furthermore, in the context of health-related applications of AR display systems, this can provide a variety of advantages, as disclosed herein. As discussed above, the display of the health system may be implemented independently of AR systems, but many embodiments below are described in relation to AR systems for illustrative purposes only.

Referring now to FIGS. 3A-3D, some general componentry options are illustrated. It should be appreciated that although the embodiments of FIGS. 3A-3D illustrate head-mounted displays, the same components may be incorporated in stationary health systems as well in some embodiments.

Figure 3A:
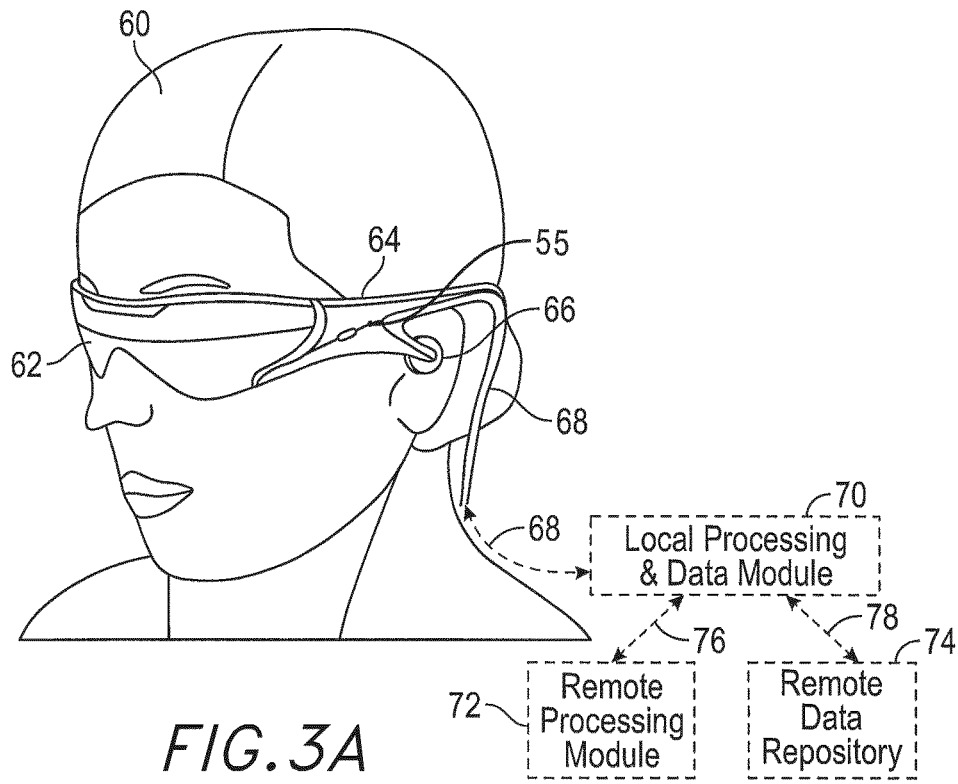
FIGS. 3A-3D illustrate various configurations of an example ophthalmic device.

As shown in FIG. 3A, a user 60 is depicted wearing a patient-worn ophthalmic device that includes a frame 64 structure coupled to a display system 62 positioned in front of the eyes of the user. The frame 64 may be coupled to a number of ophthalmic-specific measurement subsystems depending on the application of the health system. Some embodiments may be built for one or more ophthalmic applications, and other embodiments may be general AR systems that are also capable of ophthalmic applications. In either case, the following disclosure describes possible components of the health system or an AR system used for ophthalmic instrumentation and/or treatment.

In one or more embodiments, the health system is patient, or user, worn. In some other embodiments, the health system may be worn by another person (e.g., a physician or clinician) and may be used to perform a set of diagnostics tests and/or treatment protocols on a patient that is not the wearer of the system. It should be appreciated that any of the applications below may be used for health systems worn by other persons as well for conducting diagnostics tests, treatment protocols, and/or monitoring (real-time or longitudinal) on a patient.

Figure 3B:
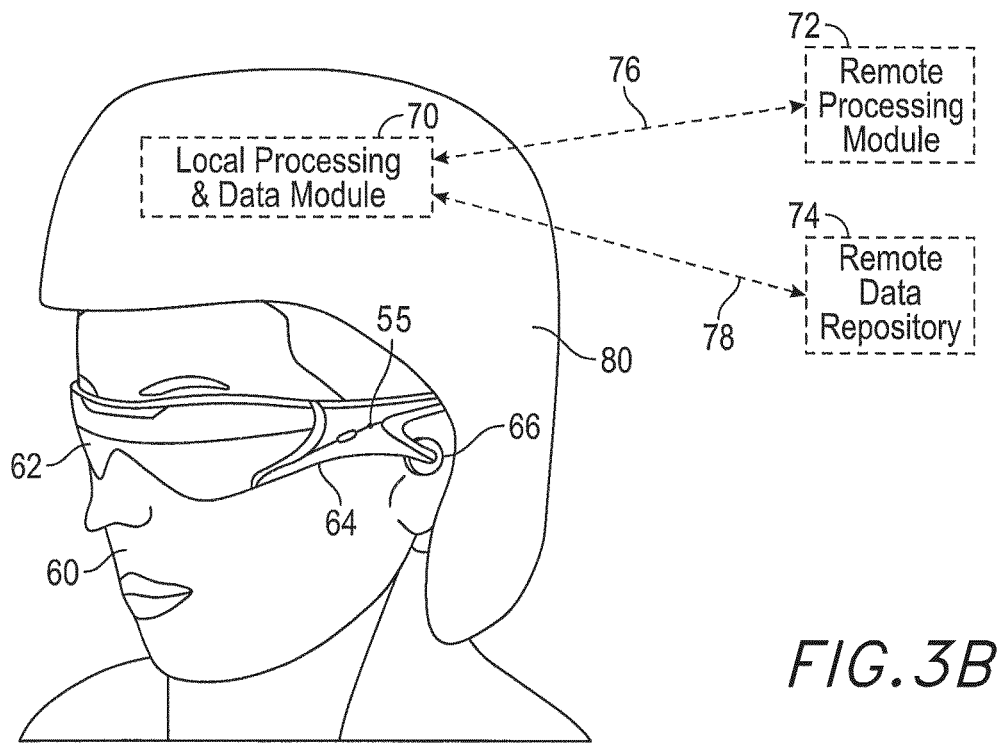
Figure 3C:
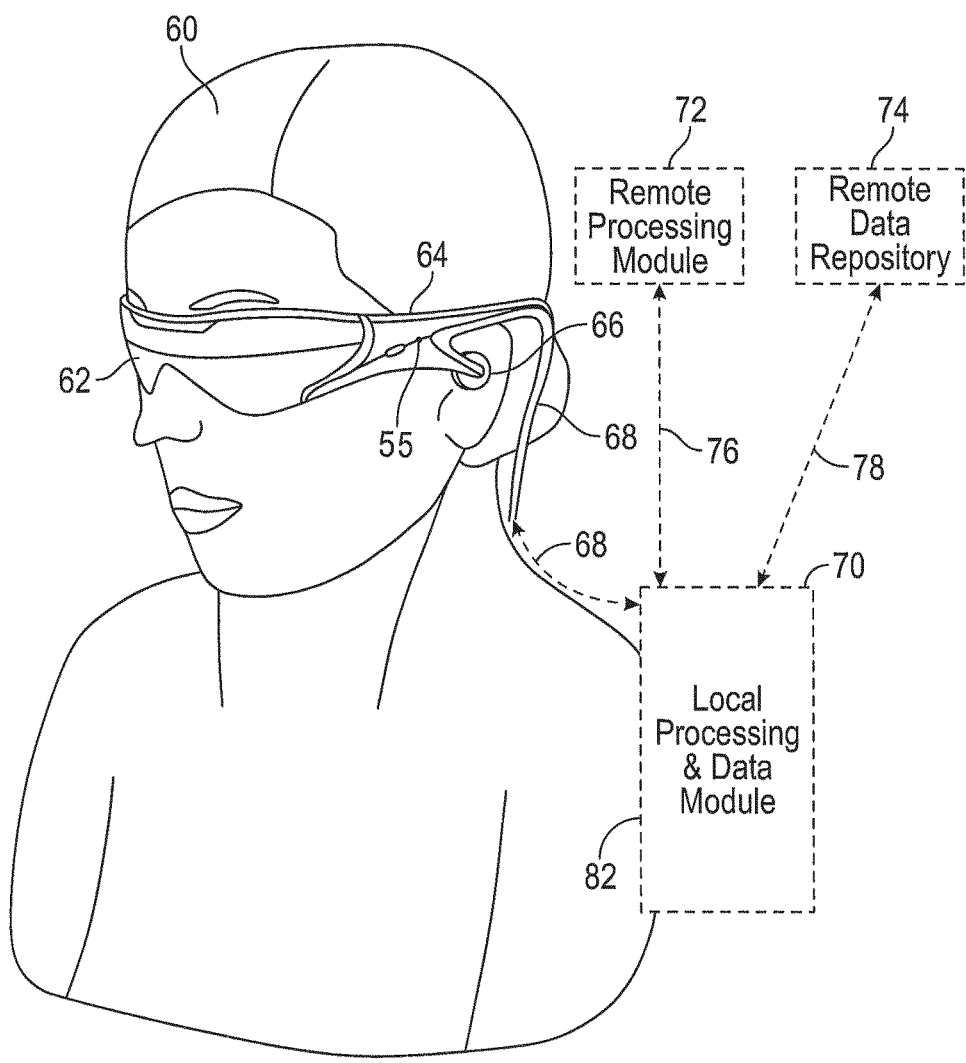
Figure 3D:
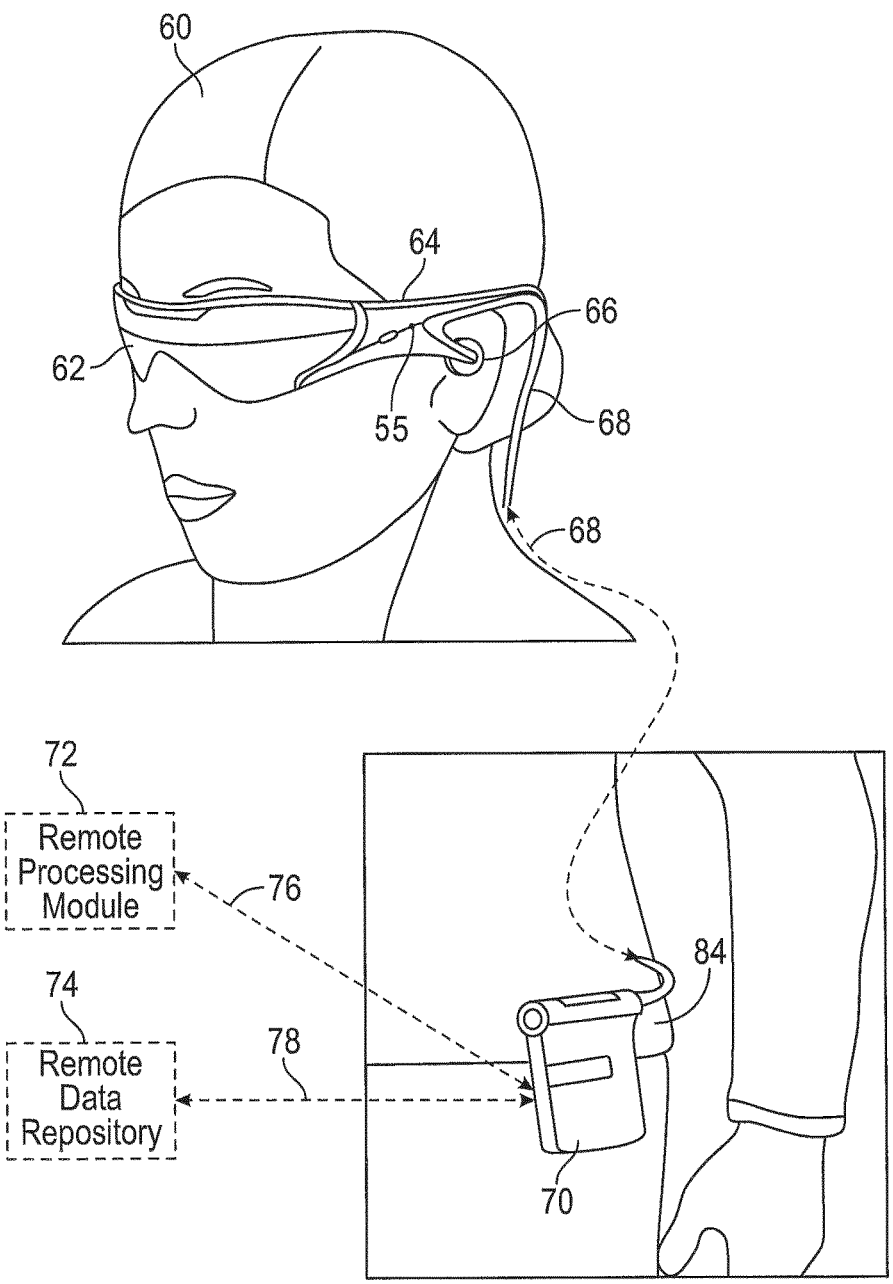

A speaker 66 may be coupled to the frame 64 in the depicted configuration and positioned adjacent to the ear canal of the user. (In one embodiment, another speaker (not shown) is positioned adjacent to the other ear canal of the user to provide for stereo/shapeable sound control.) A microphone 55 may also be coupled to the frame, to detect sound from the user or the ambient environment. In some embodiments, another microphone (not illustrated) may be provided (e.g., coupled the frame 64 on the right hand side of the user). In one or more embodiments, the health system may have a display 62 that is operatively coupled, such as by a wired lead or wireless connectivity 68, to a local processing and data module 70 which may be mounted in a variety of configurations, such as fixedly attached to the frame 64, fixedly attached to a helmet or hat 80 as shown in the embodiment of FIG. 3B, embedded in headphones, removably attached to the torso 82 of the user 60 in a backpack-style configuration as shown in the embodiment of FIG. 3C, or removably attached to the hip 84 of the user 60 in a belt-coupling style configuration as shown in the embodiment of FIG. 3D.

The local processing and data module 70 may include a power-efficient processor or controller, as well as digital memory, such as flash memory, both of which may be utilized to assist in the processing, caching, and storage of data a) captured from sensors which may be operatively coupled to the frame 64, such as image capture devices (such as cameras), microphones, inertial measurement units, accelerometers, compasses, GPS units, radio devices, and/or gyros; and/or b) acquired and/or processed using the remote processing module 72 and/or remote data repository 74, possibly for passage to the display 62 after such processing or retrieval. The local processing and data module 70 may be operatively coupled, such as via a wired or wireless communication links 76, 78, to the remote processing module 72 and remote data repository 74 such that these remote modules 72, 74 are operatively coupled to each other and available as resources to the local processing and data module 70.

In some embodiments, the remote processing module 72 may include one or more relatively powerful processors or controllers configured to analyze and process data and/or image information. In some embodiments, the remote data repository 74 may include a relatively large-scale digital data storage facility, which may be available through the Internet or other networking configuration in a "cloud" resource configuration. In some embodiments, all data is stored and all computation is performed in the local processing and data module, allowing fully autonomous use from any remote modules.

Advantageously, health systems (or AR systems having ophthalmic applications) similar to those described in FIGS. 3A-3D provide unique access to a user's eyes and head. Given that the health system interacts with the user's eye to allow the user to perceive 3D virtual content, and in many embodiments tracks various biometrics related to the user's eyes (e.g., eye vergence, eye motion, retinal structures, anterior and posterior eye geometry, patterns of eye movements, etc.), the resultant tracked data may be advantageously used in health-related applications, as described in further detail herein. This unprecedented access to the user's eyes is beneficial to the implementation of various health applications. Depending on the type of health ailment, the health system may be configured to provide imaging of, sensing of (including measurements), and/or stimulation to the user's eyes to diagnose and/or treat the ailment.

In one or more embodiments, the augmented reality display system may be used as a patient-worn, or user-worn, ophthalmic device. Ophthalmic instrumentation is used by clinicians to view into and examine a patient's eye, to execute a medical procedure, and/or to perform tests or therapy on the user's eyes. Traditionally, ophthalmic devices have been large and bulky stationary devices, and often require a patient to go to a doctor's office, wherein a clinician or the doctor performs eye-related tests on the patient. Typically, the patient is confined to the ophthalmic instrumentation device (e.g., chin on chin-resting component of ophthalmic device, head forward, etc.) until the clinician has completed the series of tests. Thus, the current approach has a number of limitations.

In addition to using a heavy and bulky device for the tests, the traditional approach requires doctor supervision, and the patient may need to return to the clinician's office repeatedly for further tests/progress evaluations and may need to be in uncomfortable or restrictive positions for extended periods of time. Further, given the short duration of time during which the patient is exposed to the ophthalmic device, there are limitations on the amount of data the clinician is able to collect in order to diagnose or treat the patient. The traditional approach does not take into account the user's behavior and dynamic changes in the orientation of the user. Many tests performed under the traditional approach require that the user be constrained in a particular, usually static, position. However, if the user is taking, for example, a visual fields test and has limited attention span, they may move their head and eyes, thereby creating noise and possibly causing inaccurate test results. In addition, the traditional approach is not engaging, interesting, or interactive.

In one or more embodiments, a head-worn health (e.g., ophthalmic) device similar to the ones shown in FIGS. 3A-3D may be used by a patient to track data, identify and correct one or more eye-related ailments, and/or help prevent other health issues. In one or more embodiments, an AR display system may be used as a head-worn health (e.g., ophthalmic) device. It should be appreciated that a number of the embodiments described below may be implemented in head-worn embodiments, while other embodiments may be implemented in stationary devices. Further, some embodiments may utilize AR technology to implement systems and methods for diagnosis, monitoring, and/or treatments with doctor supervision (e.g., for medical safety concerns, regulatory concerns, etc.), while other embodiments may be implemented for self-diagnosis and/or monitoring through the head-worn health devices or AR devices, or may be implemented as part of a treatment protocol for a particular ailment, as described herein. For illustrative purposes, the disclosure will mainly focus on head-worn health devices and particularly AR devices, but it should be appreciated that the same principles may be applied to non-head-worn embodiments as well.

In one or more embodiments, the AR display device may be used as a patient-worn health device. The device may be typically fitted for a particular user's head and/or facial features, and the optical components are aligned to the user's eyes. These configuration steps may be used in order to help ensure that the user is provided with an augmented reality experience generally free of physiological side-effects, such as headaches, nausea, discomfort, etc. Thus, in one or more embodiments, the patient-worn health system is configured (both physically and digitally) for each individual user, and a set of programs may be calibrated specifically for the user. In other scenarios, an AR device may be used comfortably by a variety of users. For example, in some embodiments, the patient worn health system knows one or more of the distance between the user's eyes, the distance from the head worn display and the user's eyes, the curvature of the user's forehead, the distance to the ears, or the height of the bridge of the nose for correct fitting purposes. All of these measurements may be used to provide the right head-worn display system for a given user. In some other embodiments, such measurements may not be necessary in order to perform the ophthalmic functions. In the context of patient-worn health systems, this aspect of the head-worn devices may be advantageous because the system already has a set of measurements about the user's physical features (e.g., eye size, head size, distance between eyes, etc.), and other data that may be used in therapy and diagnosis of the patient.

Figure 4A:
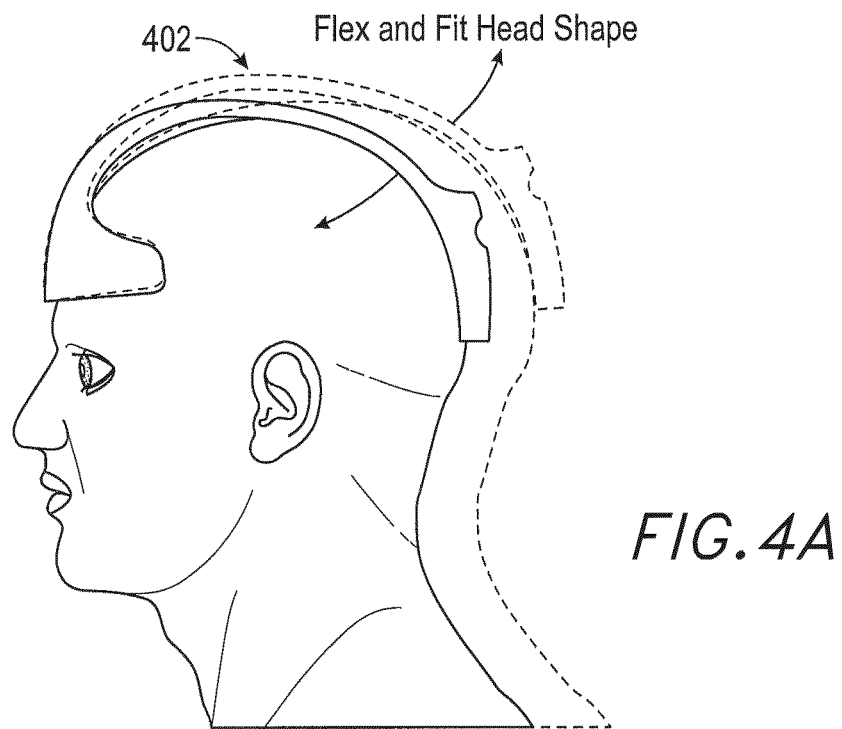
FIGS. 4A-4D illustrate various eye and head measurements taken in order to configure the ophthalmic device for a particular user.
Figure 4B:
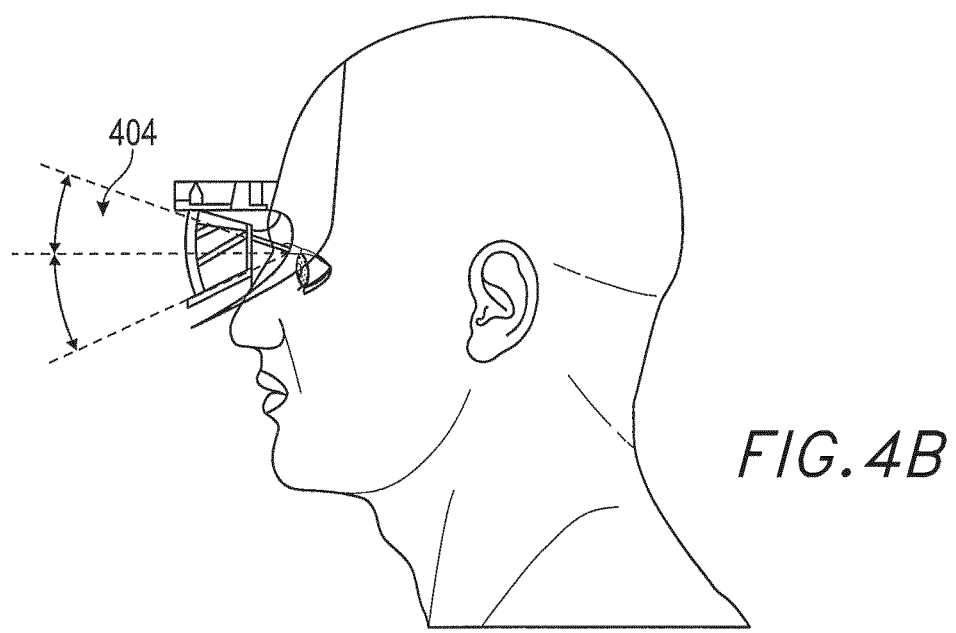
Figure 4C:
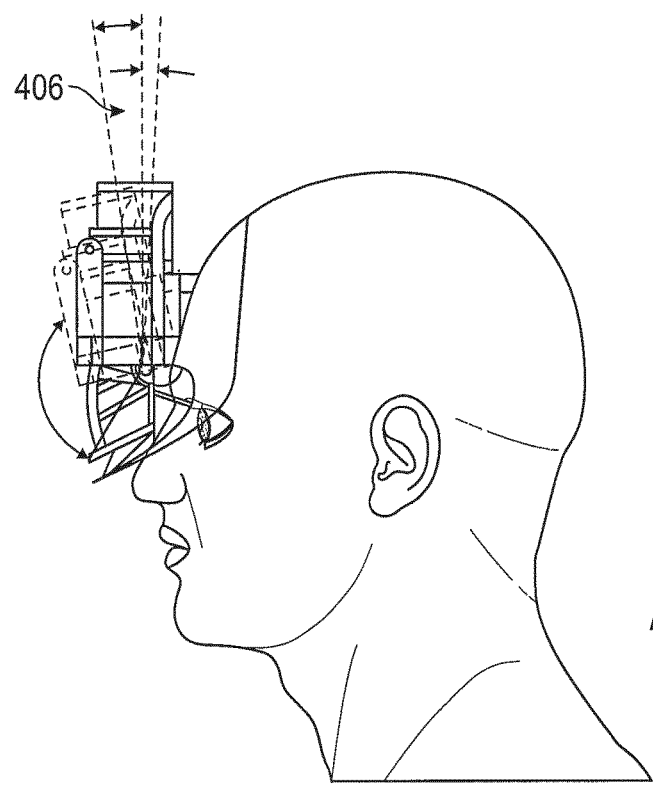
Figure 4D:
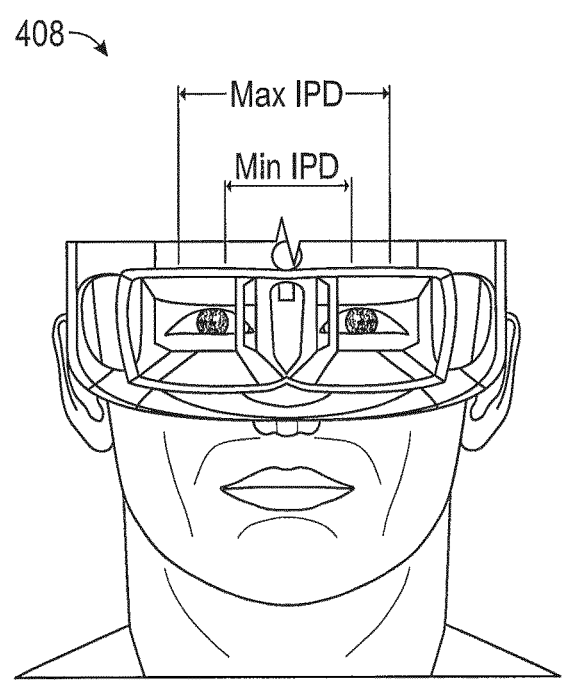

With reference to FIGS. 4A-4D, the health system may be customized for each user. The user's head shape 402 may be taken into account when fitting the head-mounted patient-worn health system, as shown in FIG. 4A. Similarly, the eye components 404 (e.g., optics, structure for the optics, etc.) may be rotated or adjusted for the user's comfort both horizontally and vertically, as shown in FIG. 4B. In one or more embodiments, as shown in FIG. 4C, a rotation point of the head set with respect to the user's head may be adjusted based on the shape of the user's head. Similarly, the inter-pupillary distance (IPD) (i.e., the distance between the user's eyes) may be compensated for, as shown in FIG. 4D.

In addition to the various measurements and calibrations performed on the user, the patient-worn health system may be configured to track a set of biometric data about the user for patient identification and secure communications. For example, the system may perform iris recognition and/or retinal matching for patient identification, track eye movements, eye movement patterns, blinking patterns, eye vergence, fatigue parameters, changes in eye color, changes in focal distance, and many other parameters that may be used in providing an optical augmented reality experience to the user. In the case of AR devices used for healthcare applications, it should be appreciated that some of the above-mentioned aspects may be part of generically-available AR devices, and other features may be incorporated for particular health-related applications.

Figure 5:
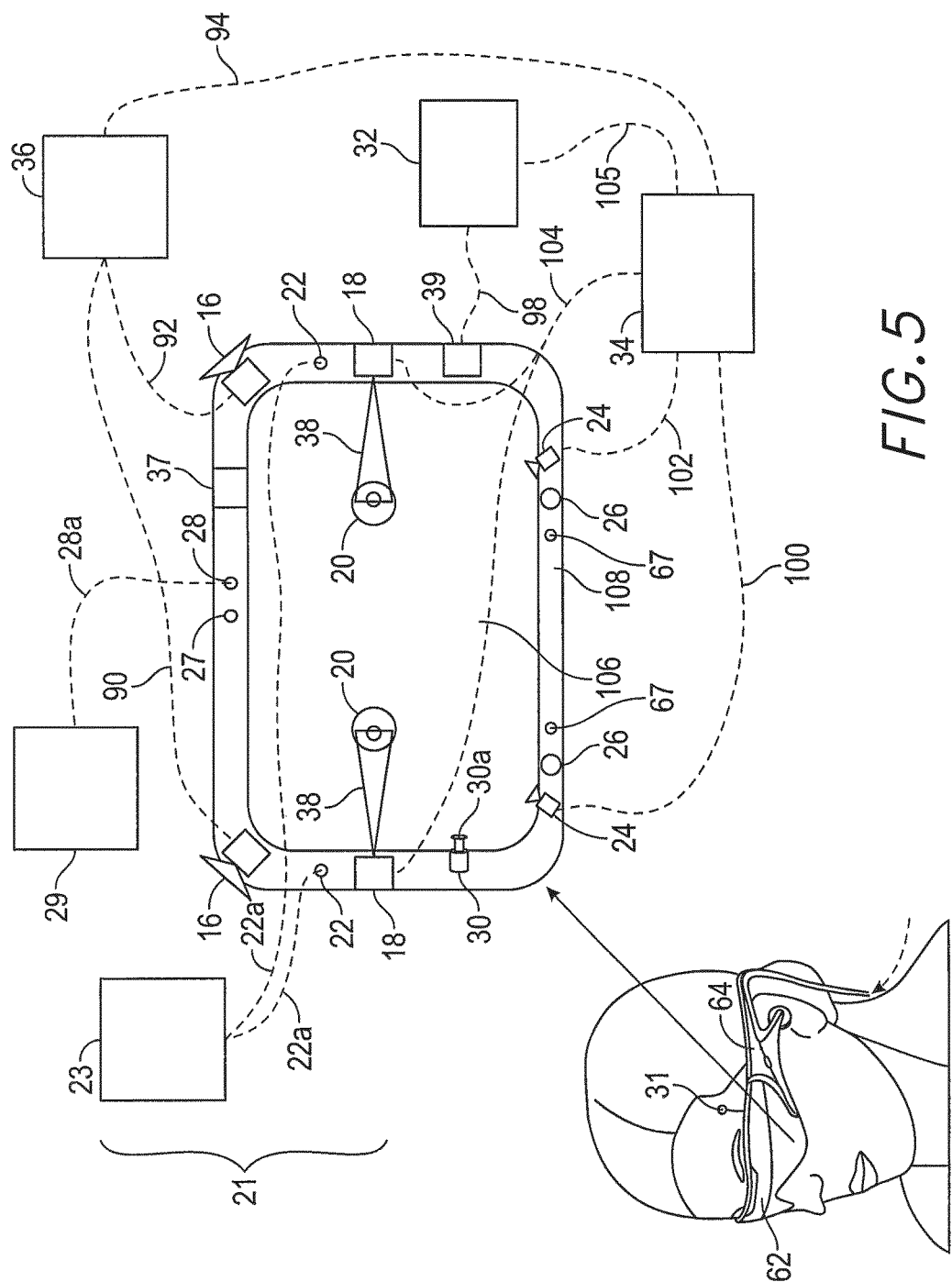
FIG. 5 shows a schematic view of various components of an ophthalmic device according to some embodiments.

With reference now to FIG. 5, the various components of an example patient-worn health display device will be described. It should be appreciated that other embodiments may have additional or fewer components depending on the application (e.g., a particular diagnostic tool) for which the system is used. Nevertheless, FIG. 5 provides a basic idea of some of the various components and types of biometric data that may be collected and stored through the patient-worn health system or AR device. FIG. 5 shows a simplified version of the head-mounted health system 62 in the block diagram to the right for illustrative purposes.

With reference to FIG. 5, one embodiment of a suitable user display device 62 is shown, comprising a display lens 106 that may be mounted to a user's head or eyes by a housing or frame 108, which corresponds to the frame 64 (FIGS. 3A-3D). The display lens 106 may comprise one or more semi-transparent mirrors positioned by the housing 108 in front of the user's eyes 20 and configured to reflect projected light 38 into the eyes 20 and facilitate beam shaping, while also allowing for transmission of at least some light from the local environment. As illustrated, two wide field-of-view machine vision cameras 16 are coupled to the housing 108 to image the environment around the user. In some embodiments, these cameras 16 are dual capture visible light/non-visible (e.g., infrared) light cameras.

With continued reference to FIG. 5, a pair of scanned-laser shaped-wavefront (e.g., for depth) light projector modules with display mirrors and optics configured to project light 38 into the eyes 20 are shown. The depicted embodiment also comprises two miniature infrared cameras 24 paired with infrared light sources 26, such as light emitting diodes "LED"s, which are configured to be able to track the eyes 20 of the user to support rendering and user input. The system 62 further features a sensor assembly 39, which may include three-axis accelerometer capability as well as a magnetic compass and three-axis gyro capability, preferably providing data at a relatively high frequency, such as 200 Hz. The depicted system also comprises a sensor head pose processor 32, such as an ASIC (application specific integrated circuit), FPGA (field programmable gate array), and/or ARM processor (advanced reduced-instruction-set machine), which may be configured to execute digital and/or analog processing to calculate real-time or near real-time user head pose from the gyro, compass, and/or accelerometer data from the sensor assembly 39. The system may also include an image head pose processor 36 which may use wide field-of-view image information output from the capture devices 16 to determine the user's head pose.

The depicted embodiment also features a GPS (global positioning satellite) subsystem 37 to assist with pose and positioning analyses. In addition, the GPS may further provide remotely-based (e.g., cloud-based) information about the user's environment. This information may be used for diagnostic purposes. For example, if the user is situated in an area having high pollen in the surrounding air, this information may be useful to diagnose and/or treat a particular ailment. Or, in another example, information about air pollution in a particular area may be advantageously used when considering treatment options for a particular user. Other types of information (e.g., pollen count, pollution, demographics, environmental toxins, climate and air quality conditions, lifestyle statistics, proximity to health-care providers, etc.) may be similarly used in one or more applications.

The depicted embodiment may also include a rendering engine 34 that may feature hardware running a software program configured to provide virtual content to be displayed to the user. The rendering engine 34 is operatively coupled via wired or wireless connectivity (e.g., 105, 94, 100, 102, 104) to the sensor head pose processor 32, the image head pose processor 36, the eye tracking cameras 24, and/or the projecting subsystem 18 such that rendered image data can be projected to the user (e.g., using a scanned laser arrangement 18 in a manner similar to a retinal scanning display). The wavefront of the projected light beam 38 may be modified to coincide with a desired focal distance of the projected light.

The cameras 24 (e.g., mini infrared cameras) may be utilized to track the eyes to support rendering and user input (e.g., where the user is looking, at what depth he or she is focusing—eye vergence may be utilized to estimate depth of focus/accommodation, etc.). The GPS 37, gyros, compass, and accelerometers 39 may be utilized to provide coarse and/or fast pose estimates. The camera 16 images and pose, in conjunction with data from an associated cloud computing resource, may be utilized to map the local world and share user views with others and/or a virtual or augmented reality community and/or healthcare providers. In one or more embodiments, the cameras 16 may be used to analyze food, drug, nutrients and toxins that the user intakes as part of a comprehensive health-care and/or wellness system or health-care surveillance system.

With continued reference to FIG. 5, the display device 62 may include a medication dispensing module 21 to deliver medication to the user. The medication dispensing module 21 may include one or more outlets 22 and at least one medication container 23, which may be a reservoir storing the medication to be dispensed out through the outlets 22.

The outlet 22 may be connected to the container 23 by one or more channels 22a, which convey the medication (e.g., a liquid or gas) from the container 23 to the outlets 22. In some embodiments, the outlets 22 may simply be openings in the frame 108, or may be nozzles attached to or integral with the frame 108. In some embodiments, the nozzles may be atomizers. In some embodiments, the channels 22a are formed by openings in the frame 108 and/or tubing.

In one or more embodiments, the display device may include a light emitting module 27 to selectively administer light to the wearer, such as for treatment of the wearer's eyes based on a treatment protocol. The light emitting module 27 may comprise a light source, which may include a light emitter which emits polychromatic polarized light, a laser, a light-emitting diode, a fluorescent lamp, a dichroic lamp, a full spectrum light source, etc. In some embodiments, one light emitting module 27 may be provided for both eyes. In some other embodiments, the display device may include multiple light emitting modules 27, and each eye may have at least one light emitting module configured to direct light to that eye.

While much of the hardware in the display system 62 featured in FIG. 5 is depicted directly coupled to the housing 108 which is adjacent the display 106 and eyes 20 of the user, the hardware components depicted may be mounted to or housed within other components, such as a belt-mounted component, as shown, for example, in FIG. 3D. In addition, as noted herein, multiple sensors and other functional modules are shown together for ease of illustration and description. It will be appreciated, however, that some embodiments may include only one or a subset of these sensors and/or modules.

In some embodiments, all of the components of the system 62 featured in FIG. 5 are directly coupled to the display housing 108 except for the image head pose processor 36, sensor head pose processor 32, and rendering engine 34, and communication between the latter three and the remaining components of the system may be by wireless communication, such as ultra-wideband, or by wired communication. The depicted housing 108 preferably is head-mountable and wearable by the user. It may also feature speakers (e.g., speakers 66, FIGS. 3A-3D), such as those which may be inserted into the ears of a user and utilized to provide sound to the user.

Regarding the projection of light 38 into the eyes 20 of the user, in some embodiments, the cameras 24 may be utilized to measure where the user's eyes 20 are looking (e.g., where the lines of sight of the two eyes intersect), which information may be used to determine the state of focus or accommodation of the eyes 20. A 3-dimensional surface of all points focused by the eyes is called the "horopter." The focal distance may take on a finite number of depths, or may be infinitely varying. Light projected physically or virtually from the vergence distance appears to be focused to the subject eye 20, while light in front of or behind the vergence distance is blurred.

Further, without being limited by theory, it has been discovered that spatially coherent light with a beam diameter of less than about 0.7 millimeters is correctly resolved by the human eye regardless of where the eye focuses. Given this understanding, to create an illusion of proper focal depth, the eye vergence may be tracked with the cameras 24, and the rendering engine 34 and projection subsystem 18 may be utilized to render all virtual objects on or close to the horopter in focus, and all other virtual objects at varying degrees of defocus (i.e., using intentionally-created blurring). Preferably the system 62 renders to the user at a frame rate of about 60 frames per second or greater. As described above, preferably the cameras 24 may be utilized for eye tracking, and software may be configured to pick up not only vergence geometry but also focus location cues to serve as user inputs. Preferably, such a display system is configured with brightness and contrast suitable for day or night use.

In some embodiments, the display system preferably has latency of less than about 20 milliseconds for visual object alignment, less than about 0.1 degree of angular alignment, and about 1 arc minute of resolution, which, without being limited by theory, is believed to be approximately the limit of the human eye. The display system 62 may be integrated with a localization system, which may involve GPS elements, optical tracking, compass, accelerometers, and/or other data sources, to assist with position and pose determination. Localization information may be utilized to facilitate accurate rendering in the user's view of the pertinent world (e.g., such information would facilitate the display system to know where it is with respect to the real world).

Having described the general components of some embodiments of a user-worn heath system (e.g., an ophthalmic system), additional components and/or features pertinent to healthcare and diagnostics will be discussed below. It should be appreciated that some of the features described below will be common to various embodiments of the user-worn health system or many embodiments of AR systems used for health purposes, while others will require additional or fewer components for health diagnostics and treatment purposes.

In some embodiments, the user-worn health system is configured to display one or more virtual images based on the accommodation of the user's eyes. Unlike prior 3D display approaches that force the user to focus where the images are being projected, in some embodiments, the user-worn health system is configured to automatically vary the focus of projected virtual content to allow for a more comfortable viewing of one or more images presented to the user. For example, if the user's eyes have a current focus of 1 m, the image may be projected to coincide with the user's focus. Or, if the user shifts focus to 3 m, the image is projected to coincide with the new focus. Thus, rather than forcing the user to a predetermined focus, the user-worn health system or AR display system of some embodiments allows the user's eye to function in a more natural manner.

Such a user-worn health system may eliminate or reduce the incidences of eye strain, headaches, and other physiological symptoms typically observed with respect to virtual reality devices. To achieve this, various embodiments of the patient-worn health system are configured to project virtual images at varying focal distances, through one or more variable focus elements (VFEs). In one or more embodiments, 3D perception may be achieved through a multi-plane focus system that projects images at fixed focal planes away from the user. Other embodiments employ variable plane focus, wherein the focal plane is moved back and forth in the z-direction to coincide with the user's present state of focus.

In both the multi-plane focus systems and variable plane focus systems, the patient-worn health system may employ eye tracking to determine the vergence of the user's eyes, to determine the user's current focus, and to project the virtual image at the determined focus.

Light of any wavelength may be projected into the user's eye. In addition to visible light, infrared light or other wavelengths of light may be similarly projected through the patient-worn health system. This aspect of the patient-worn health system may be used for imaging, diagnosing, treating, and/or compensating for health anomalies, as will be described below.

In the context of health-care and diagnostics, the type, frequency, color-scheme, placement, etc. of one or more images presented to the user may be advantageously manipulated for diagnoses, patient monitoring, and/or treatment of one or more disorders. For example, certain ailments may require strengthening of one eye in relation to the other. To this end, a treatment protocol may be devised in order to "train" the weak eye, by providing increased stimulation to the weak eye in comparison to the strong eye, for example. Or, in another example, a particular portion of the retina may have decreased sensitivity due to macular degeneration. To counter this, images may be modulated, or re-formatted and projected to the peripheries of the retina, thereby compensating for the user's decreased field of vision. Thus, as will be described in further detail below, the ability of the health system to modulate a number of parameters related to virtual image projection may be used to diagnose, monitor, and/or treat certain health anomalies.

Additionally, using the various principles outlined above, the health system may be designed to provide diagnosis using a stimulus-response measurement analysis process. Devices such as these may either be used by a clinician, or in other embodiments, certain ailments may simply be assessed or have symptoms acknowledged by the patient (e.g., eye fatigue, dry eye, hypertension, onset of stroke or seizures etc.). This may crucially help the user to actively take control of his/her health and prevent the onset of diseases by proactively taking care of them at the onset of certain symptoms. Such diagnoses and/or assessments may be made, for example, by analyzing contemporaneous data with historical data related to one or more tracked biometric parameters and environmental changes. In one or more embodiments, the health system may also be configured to provide informational cues, to send alerts to the user and/or doctor or others, or assisting in other response means.

It should be appreciated that the health system may be configured to be autonomous (i.e., to provide results directly to the user or other person or entity without input or control from a clinician or other person) as in, for example, a software-controlled implementation of the health system for diagnosing, monitoring, or treating the user, or semi-autonomous (i.e., some degree of input or control from the clinician or other person). In other embodiments, the health system may be completely controlled by the clinician or other person (e.g., in a networked or all remotely based, such as a cloud-based, implementation or in an implementation in which the health system is worn by the clinician to examine a patient).

In some embodiments, the health system may be designed with a number of additional health-related sensors. These may include, for example, accelerometers, gyroscopes, temperature sensors, pressure sensors, light sensors, non-invasive blood glucose sensors, ETCO2, EEG, and/or other physiological sensors, etc. to monitor one or more physiological responses of the user.

As described herein, the health system comprises an eye-tracking module in one or more embodiments. The eye tracking module may be configured to determine the vergence of the user's eyes in order to determine what the appropriate normal accommodation would be (through the direct relationship between vergence and accommodation) for the projection of one or more virtual images, and may also be configured to track one or more eye-related parameters (e.g., position of the eye, eye movements, eye patterns, etc.). This data may be used for several health-related diagnoses and treatment applications as will be described below.

As is apparent from the description herein, the health system may be used for diagnosis, monitoring, and therapy, which can include eye-related diagnosis, monitoring, and therapy. In eye-related applications, the health system may be referred to as an ophthalmic system. As is also apparent from the description herein, the user (or wearer) of the device may be referred to as the patient where the diagnosis, monitoring, and therapy are conducted on that user by the device. In some other embodiments, the user may be a clinician and the patient may be a third party, who may be evaluated and treated by the user. It will also be appreciated that the diagnosis and monitoring may be referred to generally as health analysis.

Light Field Processor System

Figure 6:
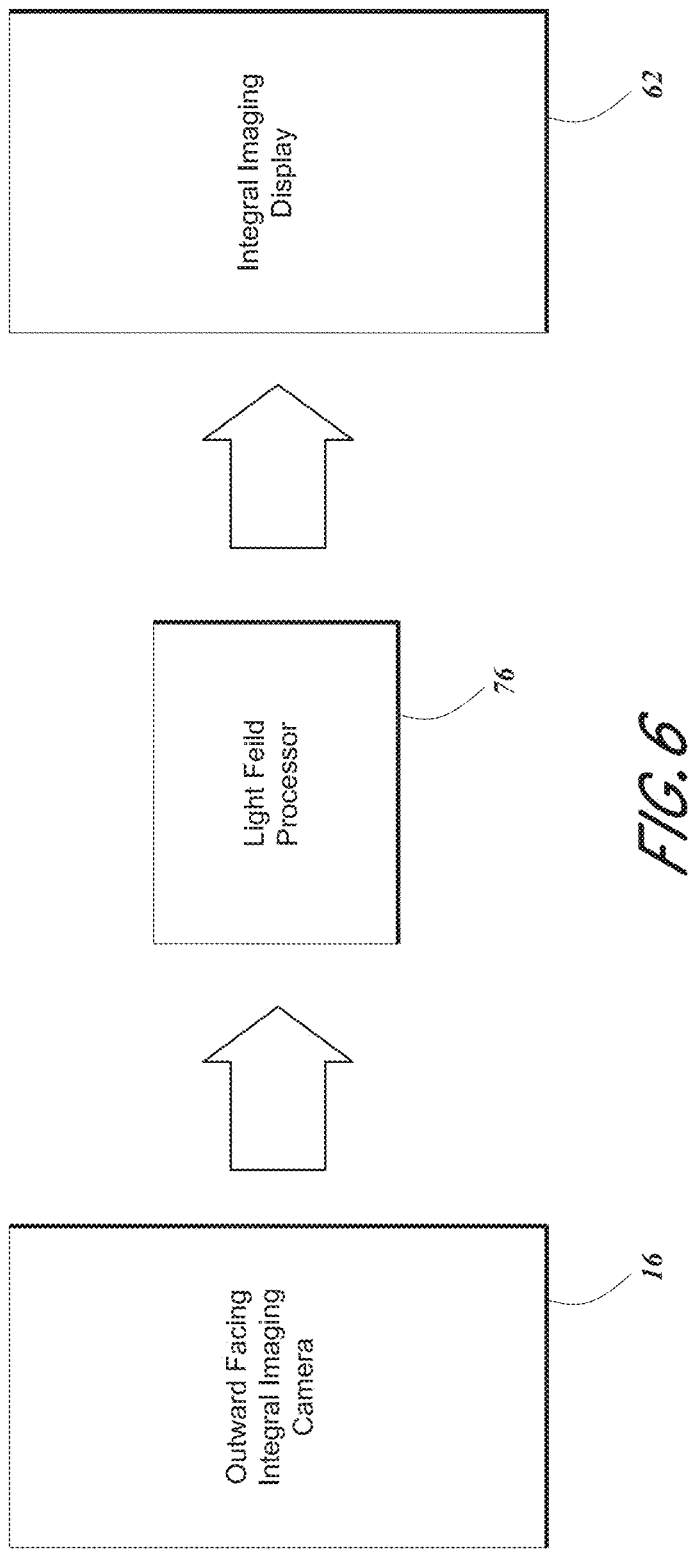
FIG. 6 illustrates a light field processor system for capturing light field image data (e.g., photographs and/or video) from at least a portion of a user's field of view and then processing the captured light field image data and displaying the processed light field image data to the user.

FIG. 6 illustrates a light field processor system 600 for capturing light field image data (e.g., photographs and/or video) from at least a portion of a user's field of view and then processing the captured light field image data and displaying the processed light field image data to the user. The light field processor system 600 can include one or more outward facing integral imaging cameras 16, a light field processor 70, and one or more integral imaging displays 62. Each of these components can be provided as part of the wearable virtual/augmented reality and health systems discussed herein. In some embodiments, the light field image data is captured, processed, and displayed substantially in real time such that the user does not perceive a lag or delay in the light field image data that is displayed.

As just mentioned, one aspect of the light field processor system 600 is that it captures, processes, and displays light field image data rather than conventional two-dimensional photographs and/or videos. The spatial world is three-dimensional, yet conventional photographs and videos record only two-dimensional images. Thus, conventional cameras reduce the complex interplay of light and matter in the three-dimensional world to a flat, two-dimensional map of the light intensity that is detected from the object space within the field of view of the camera. This flattening effect is a result of imaging, in which light rays emitted, reflected, and/or scattered at different points on an object plane within the field of view of the camera are focused by a lens to corresponding points on an image plane. Angular information is lost in this process; the light intensity recorded at a given pixel in a conventional image does not indicate the respective intensity contributions of light rays that originate with different angular orientations from the corresponding point on the object plane in the field of view. Instead, in conventional photographs and video, the intensity measured at each point in the image plane is indicative of the combined intensity of the various light rays that enter the camera with different angular orientations from the corresponding point on the object plane in the field of view. The flattening from three dimensions to two dimensions in a conventional camera significantly limits the information content of the image.

In contrast, light field data includes information about the direction and intensity of light coming from various points within the field of view. Thus, while a typical picture obtained with a conventional camera is a two-dimensional image irradiance map, light field data can be thought of as being four-dimensional because it can include information about the intensity or irradiance of light rays emanating at a plurality of angles $(\theta_x, \theta_y)$ from each of a plurality of $(x, y)$ points within the field of view. When reproduced with a light field display, a light field image provides a three-dimensional representation to the viewer similar to as if he or she were directly viewing an actual physical scene.

The outward facing integral imaging camera(s) 16 can be any camera or device that is capable of capturing light field data. An example of one such device is described herein with respect to FIG. 7. In some embodiments, one or more outward facing integral imaging cameras 16 can be integrated with a wearable system, as shown in FIGS. 3-5. Two (or more) outward facing integral imaging cameras 16 can be provided, each generally being used to capture numerical light field image data which will be displayed to one of the user's eyes. Specifically, a left outward facing integral imaging camera 16 can be provided and aligned to have a field of view that overlaps with the normal field of view of the user's left eye. Similarly, a right outward facing integral imaging camera 16 can be provided and aligned to have a field of view that overlaps with the normal field of view of the user's right eye.

The light field processor 70 can be implemented using, for example, the local processing and data modules 70 described herein. The light field processor 70 receives the captured four-dimensional numerical light field image data from the integral imaging camera(s) 16 and/or from a non-transitory computer memory. The light field processor can computationally perform a variety of operations on the captured light field image data. Such operations can include computationally adding positive or negative spherical and/or cylindrical power to the numerical light field image data, identifying one or more wavefronts represented by the numerical light field image data and computationally altering the curvature of such wavefronts; focusing the light field image data at a selected depth plane; adding prismatic power to the light field image data; adding a virtual object or other VR/AR content to the image data; deleting an object or other content from the image data; shifting the light field image data up, down, left, or right; magnifying a selected sub-portion of the captured light field image data; performing spatial and/or wavelength filtering of the image data, etc.

In some embodiments, the light field processor 70 processes the captured numerical light field image data based on an ophthalmic prescription or other characteristic of the user's eyes. (The ophthalmic prescription or other eye characteristic can be inputted to the light field processor 70 from the user or another device (e.g., a non-transitory computer memory), or the ophthalmic prescription or other eye characteristic can be measured by the light field processor system 600 itself, as described further herein.) For example, the captured numerical light field image data can be processed so as to improve at least one aspect of the user's vision. In some embodiments, the numerical light field image data can be processed so as to at least partially correct for a user's myopia, hyperopia, astigmatism, presbyopia, strabismus, amblyopia, macular degeneration, higher-order refractive errors, chromatic aberration, or micro defects. Other types of corrections are also possible.

The integral imaging display 62 can be any device that is capable of displaying light field image data. An example of one such device is described herein with respect to FIG. 7. In some embodiments, one or more integral imaging display(s) 62 can be integrated with a wearable system, as shown in FIGS. 3-5. The integral imaging display(s) 62 can be partially transparent so as to allow the user a view of his or her real world environment. Alternatively, the integral imaging display(s) may instead completely rely on the outward facing integral imaging camera(s) 16 to provide the user with image data from his or her real world environment. Two integral imaging displays 62 can be provided, each generally being used to display processed light field image data to one of the user's eyes. Specifically, a left integral imaging display 62 can be provided and aligned to display light field image data to the user's left eye. Similarly, a right integral imaging display 62 can be provided and aligned to display light field image data the user's right eye.

Figure 7:
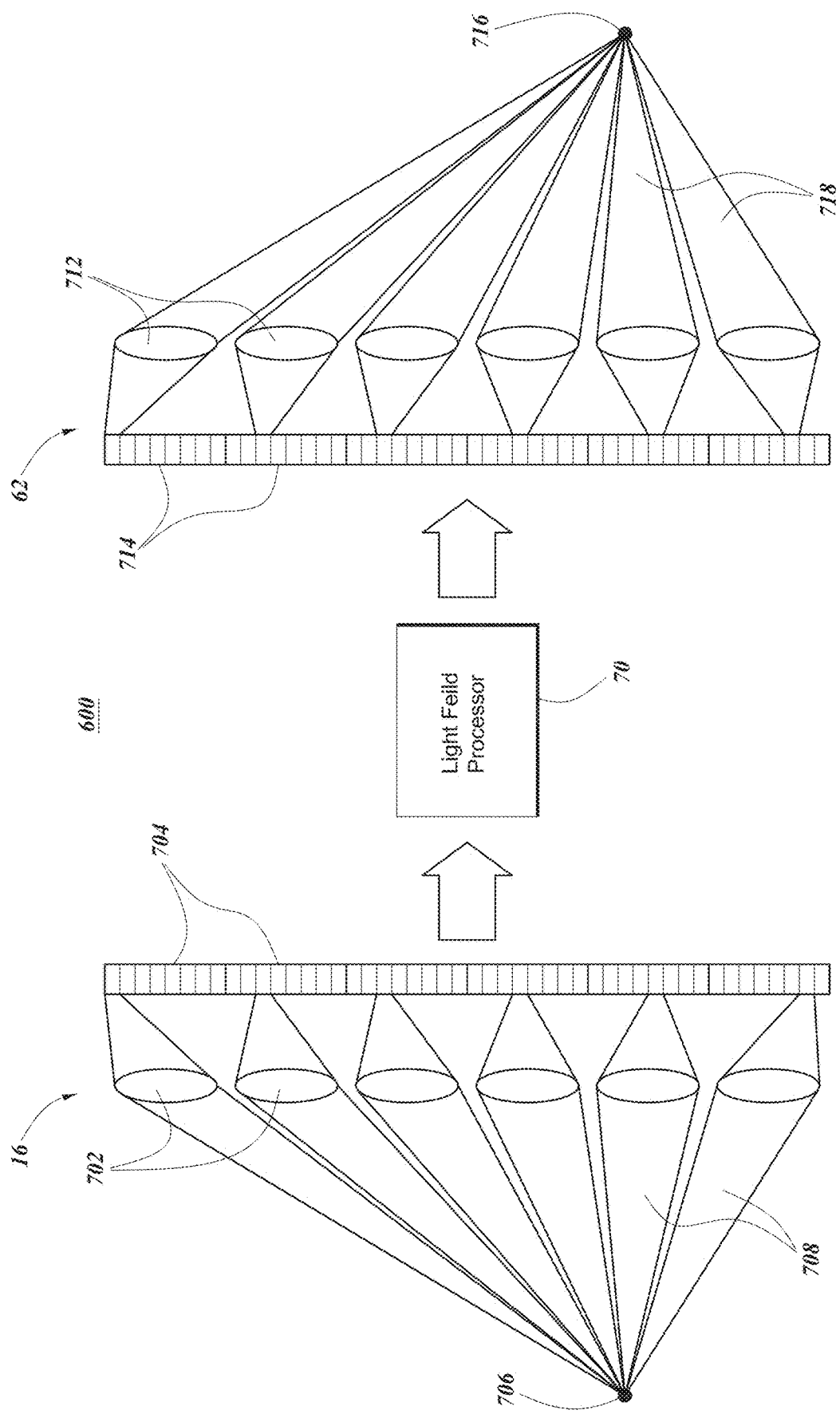
FIG. 7 is a schematic illustration of an embodiment of the light field processor system of FIG. 6.

FIG. 7 is a schematic illustration of an embodiment of the light field processor system 600 of FIG. 6. The outward facing integral imaging camera 16 can include a two-dimensional array of micro-lenses 702 and a corresponding two-dimensional array of photodetectors 704 with light-sensitive pixels. The photodetector array 704 can be, for example, a complementary metal-oxide-semiconductor (CMOS) sensor, a charge-coupled device (CCD) sensor, an array of CMOS or CCD sensors, or any other device capable of detecting and digitizing light energy. The array of photodetectors can form a planar surface or a curved surface (e.g., the array of photodetectors can be curved radially around the eye to facilitate capture of light from any location where the eye may be looking). The micro-lens array 702 gathers light from a point 706 in object space within the user's field of view. Each micro-lens, or lenslet, samples a spatially localized region of the wavefronts of light that enter the integral imaging camera 16 from the field of view, and allows local angular information to be recorded on the photodetector array 704. In this way, the photodetector array 704 can detect the respective intensity of light rays that arrive at the instrument from different angular directions. For example, as shown in FIG. 7, various cones of light 708 originate from the point 706 at different angles ($\theta_x$, $\theta_y$) in the object space. Each lenslet 702 focuses a cone of light 708 which originates from the point 706 with a different angular orientation onto the photodetector array 704. Although only a single point 706 is illustrated, each lenslet 702 performs this function for each point on an (x, y) plane in the object space. In other words, each lenslet 702 creates an elemental image of the scene in object space with a slightly different perspective than the elemental images created by other lenslets 702 in the array. Each elemental image is recorded by a group of photodetectors in the photodetector array 704. Collectively, this two-dimensional array of elemental images form what is referred to as an integral image. The integral image is one of various possible light field representations of the scene. It includes a two-dimensional array of elemental images, each captured from a slightly different perspective.

The captured light field image data from the integral imaging camera 16 can be represented in various numerical forms after being digitized by the integral imaging camera. This allows the light field processor 70 to perform mathematical manipulations (such as those described above) on the captured light field image data. Once the light field processor 70 has performed the desired mathematical manipulations on the captured light field image data, the processed light field image data is then passed to the integral imaging display 62. In some embodiments, the processed light field image data can be passed to the integral imaging display 62 in the form of one or more processed integral images, each consisting of a set of processed elemental images.

As shown in FIG. 7, the integral imaging display 62 includes a two-dimensional array of micro-lenses 712 and a two-dimensional array of light sources 714. The integral imaging display 62 may include a controller to modulate the array of light sources 714 using, for example, the processed light field image data. The array of light sources 714 can be, for example, a red, green, blue (RGB) array of light emitting diodes (LEDs). Some embodiments may also include infrared emitting light sources to project infrared light into the wearer's eyes for any of the reasons discussed later herein. Alternatively, the array of light sources 714 can be implemented as a liquid crystal display (LCD) panel or some other type of display panel. Each light source can be used to emit light corresponding to a pixel or sub-pixel of the processed integral image. The light emitted from each light source 714 is then projected by one of the lenslets 712 to a corresponding point 716 in space before the user's eye. In some embodiments, each lenslet 712 projects one of the processed elemental images. The overlap of light from each of the projected elemental images re-creates a physical light field which can be viewed by a user. This physical light field is perceived as three-dimensional by the user, similar to as if he or she were viewing an actual three-dimensional scene. If the light field processor 70 were to not alter the integral image collected by the integral imaging camera 16, then the physical light field created by the integral imaging display 62 would be a representation of the same physical light field that existed in the object space within the field of view of the camera 16. This is shown in FIG. 7, where the intersection of all the projected cones of light 718 results in an irradiance distribution which reproduces the radiance of the original three-dimensional scene. Otherwise, if the light field processor 70 is used to alter the integral image, then the physical light field projected by the integral imaging display 62 is a similarly altered version of the physical light field that existed in the object space within the field of view of the camera 16.

While FIG. 7 illustrates one embodiment of a light field capturing/processing/displaying system 600, other embodiments are also possible. For example, the integral imaging camera 16 shown in FIG. 7 could be replaced with any type of device capable of capturing light field image data. Similarly, the integral imaging display 62 shown in FIG. 7 could also be replaced with any type of device capable of displaying light field image data.

Correction of Myopia, Hyperopia, Astigmatism, and Higher-Order Aberrations

Figure 8:
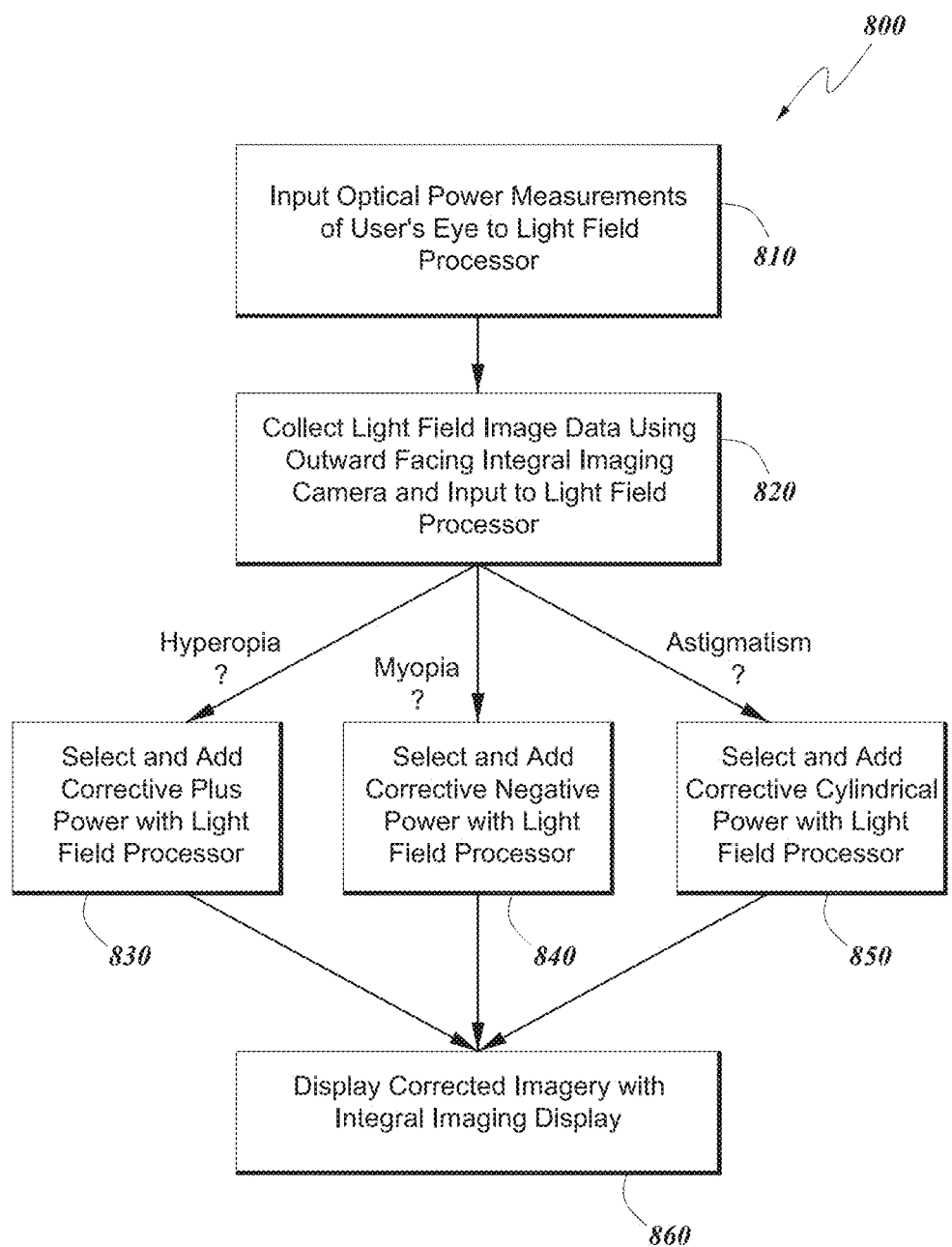
FIG. 8 is a flowchart that illustrates a method for using the light field processor system shown in FIGS. 6 and 7 to correct myopia, hyperopia, and/or astigmatism for a user.

FIG. 8 is a flowchart that illustrates a method 800 for using the light field processor system 600 shown in FIGS. 6 and 7 to correct myopia, hyperopia, and/or astigmatism for a user. The method 800 begins at block 810, where the light field processor 70 of the system 600 receives the user's optical power measurements. The optical power measurements may comprise the user's optical prescription for eyeglasses, including spherical power, cylindrical power, and/or cylindrical power axis measurements. These measurements may be performed by the system 600 itself (as discussed further herein), or they may be received from the user or a separate diagnostic device. The optical prescription may be determined during initialization of the light field processor system 600, during calibration of the system 600, as part of an eye-prescription configurator program (e.g., using a phoropter or other visual acuity examination), or at any time during use of the light field processor system. Biometric data may be used to identify a user and associated optical prescription.

As just mentioned, there are many ways in which optical power measurements of the user's eye can be input to the light field processor system 600. In some embodiments, the user may simply provide the light field processor system 600 with the information. For example, the user may input a prescription into a user interface. Or, in other embodiments, the light field processor system 600 may be configured to automatically or interactively determine an optical prescription of a user. For example, the light field processor system may go through an eye-prescription configurator program to manually and interactively determine the user's prescription. The light field processor 70 may be pre-programmed with discrete granular steps in adjusting focus or altered wavefronts of the collected light field image data. Adjusting the focus or altering wavefronts may include adjusting spherical power and/or adjusting cylindrical power/axis. The user may specify a desired amount of power alteration to the light field processor system through an appropriate feedback mechanism (e.g., a user interface). Or, in some embodiments, the user may have the option of incrementally increasing or decreasing a prescription value until the user arrives at a comfortable viewing prescription.

In some embodiments, the light field processor system 600 may automatically measure the user's optical prescription for each eye (and incrementally change the applied corrections in real-time for each eye), without requiring user input, based on monitoring and tracking the eyes via an eye-tracking system, autorefraction, abberometry, or other systems as described herein. In some embodiments, the light field processor system 600 may utilize a biofeedback system (discussed herein) to automatically change the applied corrective prescription.

In some embodiments, the light field processor system 600 may be configured to receive the user's optical prescription from a third party system. For example, a doctor may be able to send a user optical prescription wirelessly (e.g., over the internet, Blue-tooth connection, etc.), which is received by a receiver and stored in the digital memory of the light field processor 70.

At block 820, the outward facing integral imaging camera 16 of the system 600 captures light field image data and inputs the captured light field image data to the light field processor 70. As discussed herein, the captured light field can be mathematically manipulated prior to being displayed by the integral imaging display 62. While a wide variety of mathematical manipulations can be performed, some of the mathematical manipulations may be used to at least partially correct the captured light field image data based on one or more characteristics of the user's eye(s), such as his or her optical prescription, the shape or curvature of the cornea, the length of the eye, etc. The light field processor 70 can be used to make real-time changes to the user's incoming light field before then displaying the altered light field to the user.

In some embodiments, the specific corrections which are applied by the light field processor can be adjusted dynamically to correct vision defects as the user's vision changes over time. For example, in some embodiments, the light field processor system 600 may implement dynamic vision correction by initiating an eye-prescription configurator program. The light field processor system can be configured to determine the user's prescription at intervals of time with or without user activation. Thus, the light field processor system may dynamically identify a first optical prescription at a first time and may adjust the vision correction based on that prescription, and may identify a second optical prescription at a second time and may adjust the vision correction based on that second prescription.

Common vision defects which can be at least partially corrected by the light field processor 70 include short-sightedness (i.e., myopia), far-sightedness (i.e., hyperopia), and astigmatism. Conventionally, these defects are corrected using spherical and/or cylindrical lenses. However, the light field processor system 600 can alternatively correct these defects via computational manipulations of the captured light field.

Figure 9A:
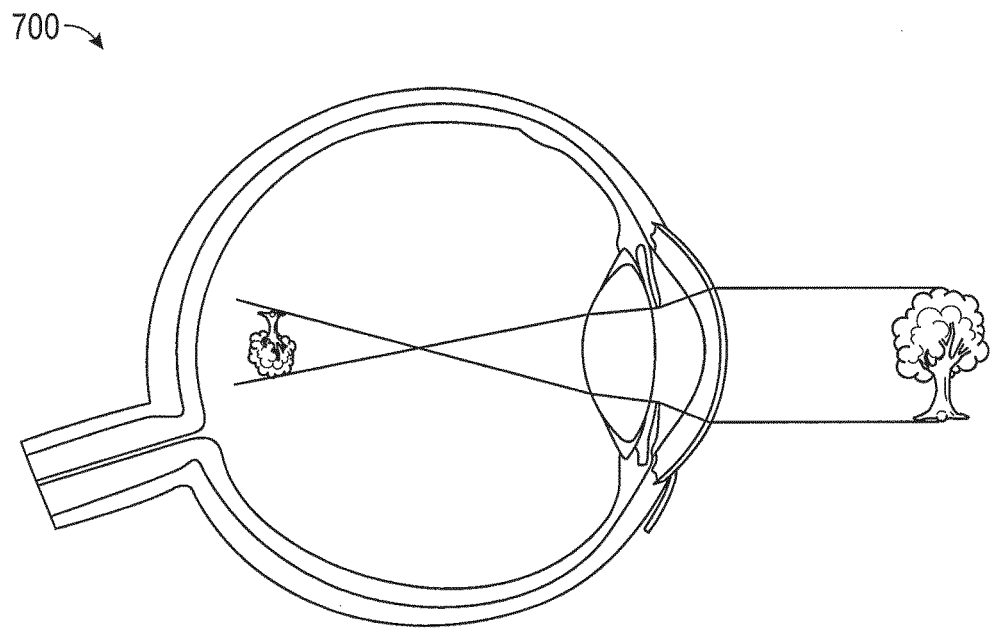
FIGS. 9A-9B illustrate a schematic, cross-sectional view of a user's eye suffering from myopia.
Figure 9B:
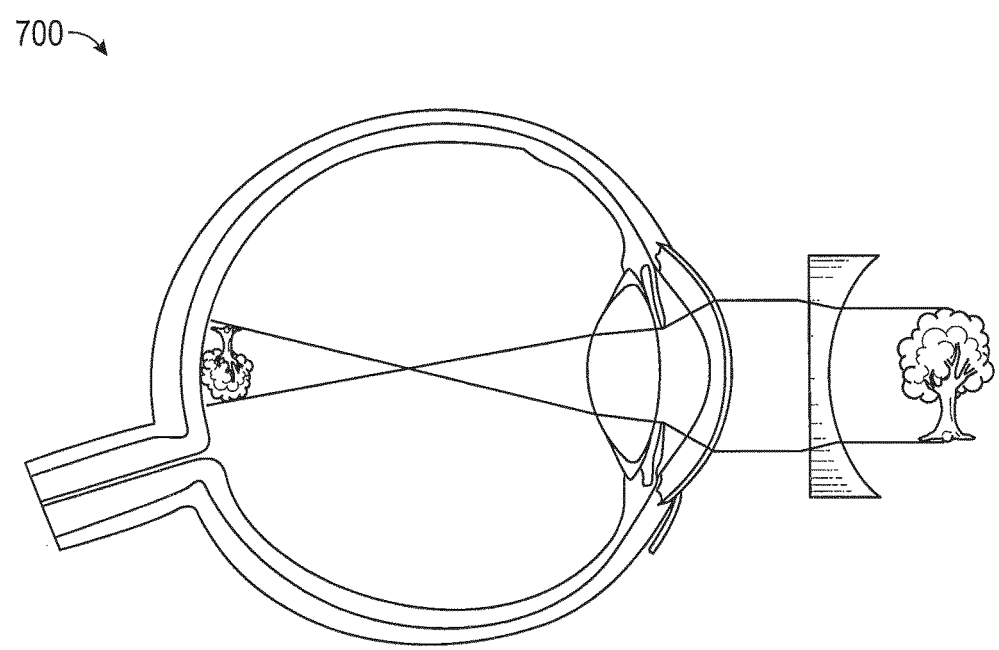

In the case of myopia, light associated with one or more objects in the user's field of view is focused in front of the retina, as shown in FIG. 9A, rather than onto the retina. This causes the objects to appear out of focus. Referring now to FIG. 9B, conventionally, a negative powered concave lens can be used to compensate for the disorder, introducing negative optical power which causes the light to be focused on the retina. The light field processor 70 can replace the corrective concave lens shown in FIG. 9B with mathematical manipulations of the numerical light field image data captured by the outward facing integral imaging camera 16 shown in FIGS. 6 and 7. For example, as shown in block 840 of FIG. 8, if the user's optical prescription indicates that he or she has myopia, then the light field processor 70 selects and computationally introduces an amount of negative spherical power wavefront curvature to the captured light field image data so as to at least partially correct for the user's myopia.

Figure 10A:
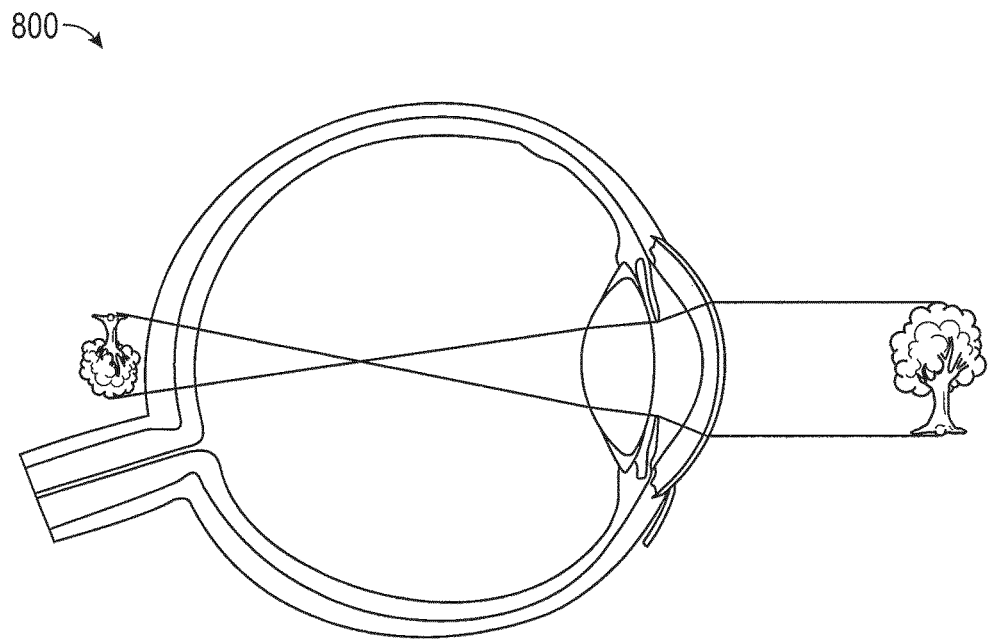
FIGS. 10A-10B illustrate a schematic, cross-sectional view of a user's eye suffering from hyperopia.
Figure 10B:
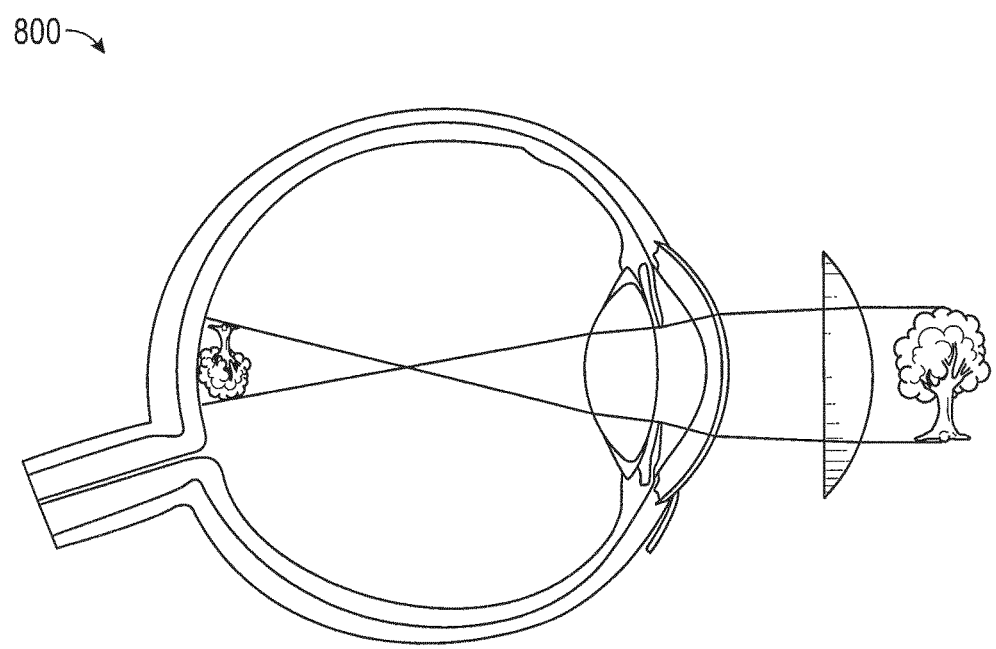

In the case of hyperopia, light associated with one or more objects is focused behind the retina, as shown in FIG. 10A, rather than on the retina. This causes the objects to appear out of focus. Referring now to FIG. 10B, conventionally, a positive powered convex lens can be used to compensate for the disorder. Once again, the light field processor 70 can replace the corrective convex lens shown in FIG. 10B with mathematical manipulations of the light field captured by the outward facing integral imaging camera 16 shown in FIGS. 6 and 7. For example, as shown in block 830 of FIG. 8, if the user's optical prescription indicates that he or she has hyperopia, then the light field processor 70 selects and computationally introduces an amount of positive spherical power wavefront curvature to the captured light field image data so as to at least partially correct for the user's hyperopia.

Figure 11A:
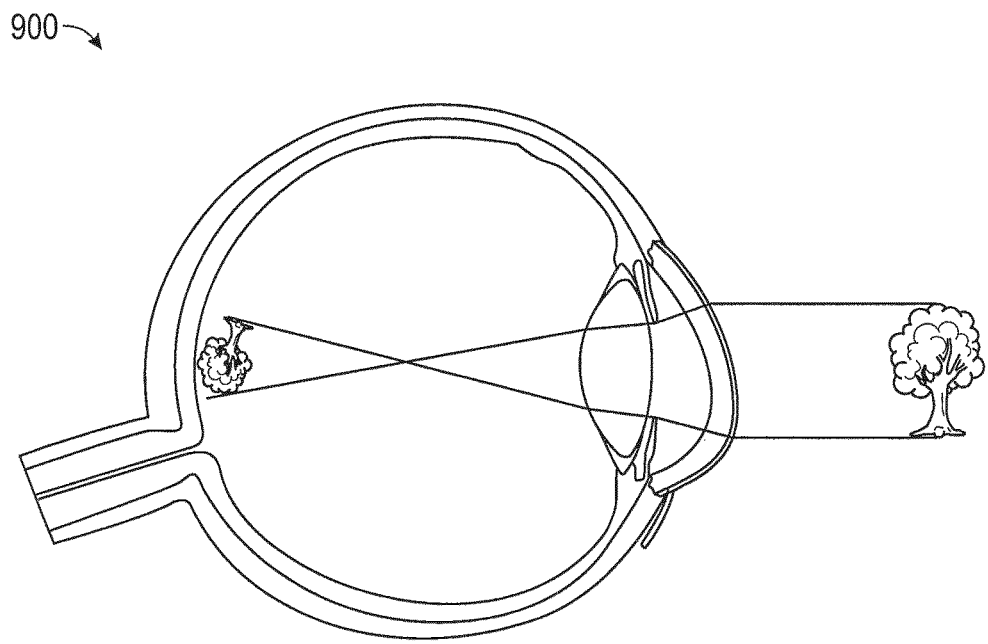
FIGS. 11A-11B illustrate a schematic, cross-sectional view of a user's eye suffering from astigmatism.
Figure 11B:
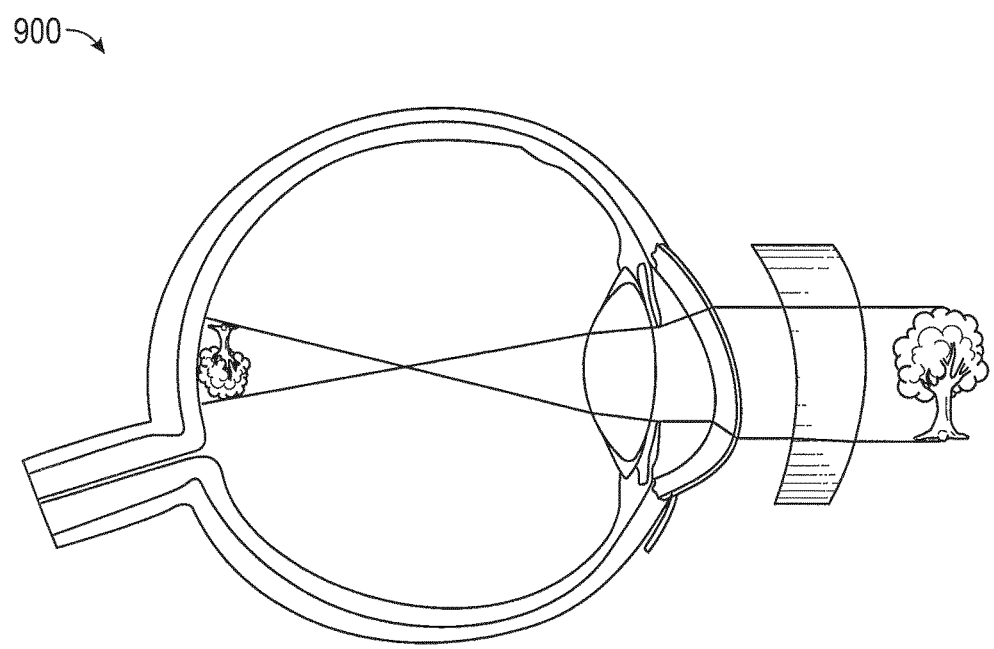

Astigmatism is a condition wherein the eye exhibits cylindrical optical power (i.e., the power of the eye is different when measured with respect to one meridian than it is with respect to the orthogonal meridian). As is schematically illustrated in FIG. 11A, this can be caused by an irregularly shaped cornea. For example, the curvature along one meridian may be different than the curvature along the perpendicular meridian. Referring now to FIG. 11B, conventionally, astigmatism can be corrected by introduction of an appropriately oriented cylindrical lens. Yet again, the light field processor system 600 can replace the corrective lens shown in FIG. 11B with mathematical manipulations of the light field captured by the outward facing integral imaging camera 16 shown in FIGS. 6 and 7. Specifically, as shown in block 850 of FIG. 8, the light field processor 70 can select and computationally introduce an amount of cylindrical optical power (oriented at the angular axis indicated by the user's prescription) so as to at least partially correct the captured light field image data for the user's astigmatism.

The light field processor system 600 is not limited to correction of simple lower-order optical aberrations such as defocus and/or astigmatism, however. Indeed, the light field processor 70 can also apply computational corrections to the captured light field for complex higher-order optical aberrations, as well. In some cases, these higher-order aberrations may account for about 10% of all refractive errors. These higher-order refractive errors may be caused by irregularly shaped optical surfaces in the eye, and are particularly common after refractive surgeries. For example, shape irregularities in the cornea and/or crystalline lens of the eye may introduce higher-order refractive errors to the light that passes through the eye to the retina. Such higher-order aberrations may be reduced with appropriate refractive correction.

Various implementations of the light field processor system 600 described herein may be applicable for providing computational correction to incoming wavefronts for these higher-order aberrations. Such computational corrections can be applied by the light field processor 70 based on a measurement of the higher-order aberrations of the user's eye. Wavefront corrections, including corrections of all aberrations described by Zernike modes (e.g., astigmatism, coma, trefoil, spherical aberrations, quatrefoil, etc.), may be made utilizing the light field processor system 600 described herein.

In some embodiments, the light field processor system 600 may have the capability to measure higher-order aberrations of the user's eyes, as described herein. These measurements can then be used by the light field processor 70 to computationally alter the light field image data collected by the integral imaging camera 16. In other embodiments, the light field processor 70 receives higher-order aberration measurements of the user's eyes from an external device. For example, the light field processor system 600 may include one or more transmitters and receivers to allow transmission and reception of data between the system and the remote processing module 72 and/or remote data repository 74. The transmitter and receiver may be combined into a transceiver. In some embodiments, the remote processing module 72 and/or remote data repository 74 may be part of a third party server and database that enable a third party (e.g., a doctor or other medical administrator) to transmit data, such as for example, an optical prescription, to the ophthalmic device.

In some embodiments, the method for correcting for higher-order aberrations may be similar to method 800 described in FIG. 8 for correcting myopia, hyperopia, or astigmatism. The light field processor 70 first receives measurements of the higher-order aberrations of the user's eye(s). These measurements can be provided as Zernike coefficients, as a map of the topography of the cornea, or in any other suitable format. The light field processor 70 then receives light field image data collected by the integral imaging camera 16. Finally, the light field processor 70 selects one or more adjustments to make to the wavefronts of the captured light field data so as to at least partially reduce one or more higher-order aberrations. These corrections are applied computationally.

The eye of a user may experience higher-order refractive errors which vary with changing accommodation. Accordingly, in some embodiments the light field processor 70 may select a different set of wavefront adjustments to make to the incoming light field based on the current accommodation of the user's eye(s) and/or based on the focal plane of the light field image data.

In some implementations, the light field processor system 600 may also be configured to alter the collected light field image data so as to reduce the effects of microscopic defects in the cornea, crystalline lens, and/or other anatomy of the eye. These defects can generate complex refraction, reflection, and scattering patterns that impair visual quality. The light field processor 70 can spatially filter rays of light which would interact with these defects, thus blocking those optical pathways that contribute to impaired visual quality. This can be done by identifying light rays in the collected light field image data which would interact with defects in the user's eye(s) and then computationally removing those selected rays from the processed light field.

Once the light field processor 70 has performed the desired computational corrections on the captured light field image data, at block 860 the integral imaging display 62 displays the corrected light field image data to the user.

In some embodiments, the light field processor system 600 may comprise a biofeedback system configured to determine a comfort level of the user in viewing an object or image. For example, if a user's eyes are shifting, changing accommodation, changing pupil size, changing vergence, etc., these may be indicators that the user is unable to comfortably view an object or image. Instability or oscillation in accommodation or behaviors associated with accommodation may be a sign that the user is struggling with focusing on an object. Accordingly, the biofeedback system may receive real-time inputs relating to the state or properties of the user's eye.

In various embodiments, the light field processor system 600 includes one or more eye tracking cameras or other cameras or imaging systems to track one or more eyes of the user. For example, some embodiments may utilize cameras 24 (e.g., infrared cameras) paired with light sources 26 (e.g., infrared light sources) configured to monitor and track the eyes of the user. These cameras and sources can be operatively coupled to the light field processor system 600. Such cameras and/or imaging systems can monitor the orientation of the eyes, pupil sizes of the eyes, vergence of the eyes, and the corresponding directions of the respective lines of sight of the eyes. In some embodiments, the cameras 24 may be used to determine the convergence point of the eyes. In addition, as described herein, the system 600 may be configured to determine accommodation of the eyes of the user. The eye tracking system may detect a fluctuation in the accommodation of the eyes by comparing multiple measurements. In some embodiments, the accommodation may be monitored based on the shape of the lens(es) of the eye(s), vergence of the eyes, pupil size, etc. In some embodiments, monitoring the accommodation state may comprise projecting a small image into the eye (e.g., a dot or multiple dots) and, using inward facing cameras, monitoring whether the image is focused on the retina. Fluctuations in accommodation may indicate an uncomfortable focal depth or blurred image. Thus, the light field processor system may computationally increase or decrease the prescription until the fluctuations cease or lessen, thereby arriving at a comfortable viewing prescription.

In some embodiments, the ophthalmic device comprises gyroscopic sensors, accelerometers, other sensors, or a combination thereof to monitor changes in the head position, head pose or orientation. In some embodiments, the system 600 may comprise a sensor assembly 39 configured to detect movement and/or orientation of the system due to movement of the user's head. The biofeedback system may be configured to receive the detected head movement, and if the frequency and/or magnitude of movement is beyond a threshold, the system may be configured to determine that the user is unable to comfortably view the image. For example, constant head movement may be indicative of a searching for a comfortable viewing position of the image. If such signs that the person may not be focusing well are present, then the light field processor system may be configured to alert the user of such, perform a subjective vision test, or objectively and automatically evaluate the user's prescription to improve vision quality.

The following paragraphs describe various example embodiments of the devices, systems, and methods described herein.

A wearable ophthalmic device, comprising: an outward facing head-mounted light field camera configured to receive light from a user's surroundings and to generate numerical light field image data; a light field processor configured to access the numerical light field image data, to obtain an optical prescription for an eye of the user, and to computationally introduce an amount of positive or negative optical power to the numerical light field image data based on the optical prescription to generate modified numerical light field image data; and a head-mounted light field display configured to generate a physical light field corresponding to the modified numerical light field image data.

The device of the preceding paragraph, wherein the optical power comprises spherical or cylindrical optical power.

The device of any of the preceding paragraphs, wherein the modified numerical light field image data is at least partially corrected for the optical prescription.

The device of any of the preceding paragraphs, wherein the light field processor is configured to generate the modified numerical light field image data by identifying one or more wavefronts represented by the numerical light field image data and computationally modifying the curvature of the one or more wavefronts based on the optical prescription.

The device of any of the preceding paragraphs, wherein the light field processor is further configured to add virtual reality or augmented reality image content to the numerical light field image data.

The device of any of the preceding paragraphs, wherein the optical prescription comprises a prescription for myopia.

The device of any of the preceding paragraphs, wherein the optical prescription comprises a prescription for hyperopia.

The device of any of the preceding paragraphs, wherein the optical prescription comprises a prescription for astigmatism.

The device of any of the preceding paragraphs, wherein the optical prescription comprises information regarding higher-order aberrations of the user's eye.

The device of any of the preceding paragraphs, wherein the light field camera comprises an integral imaging camera with a two-dimensional array of micro-lenses and a corresponding two-dimensional array of photodetectors.

The device of any of the preceding paragraphs, wherein the light field display comprises an integral imaging display with a two-dimensional array of micro-lenses and a corresponding two-dimensional array of light sources.

The device of any of the preceding paragraphs, wherein the light field display comprises one or more infrared light sources configured to project infrared light into the user's eye to measure the optical prescription.

The device of any of the preceding paragraphs, wherein the light field processor is configured to generate the modified numerical light field image data in real-time.

The device of any of the preceding paragraphs, wherein the light field processor is configured generate the optical prescription.

The device of the preceding paragraph, wherein the light field processor is configured to generate the optical prescription by: computationally introducing a first test amount of positive or negative optical power to the numerical light field image data; receiving feedback from the user regarding the first test amount of positive or negative optical power;

and computationally introducing a second test amount of positive or negative optical power to the light field image data.

The device of any of the preceding paragraphs, wherein the light field processor is further configured to generate the modified numerical light field image data by removing one or more light rays which would interact with a defect in the user's cornea or crystalline lens if generated as part of the physical light field.

A method for using a wearable ophthalmic device, the method comprising: computationally introducing an amount of positive or negative optical power to numerical light field image data of a user's surroundings so as to generate modified numerical light field image data, the amount of optical power being based on an optical prescription for the user; and generating a physical light field corresponding to the modified numerical light field image data using a light field display.

The method of the preceding paragraph, wherein the optical power comprises spherical or cylindrical optical power.

The method of any of the preceding paragraphs, wherein generating the modified numerical light field image data comprises at least partially correcting the numerical light field image data for the optical prescription.

The method of any of the preceding paragraphs, wherein generating the modified numerical light field image data comprises identifying one or more wavefronts represented by the numerical light field image data and computationally modifying the curvature of the one or more wavefronts based on the optical prescription.

The method of any of the preceding paragraphs, further comprising adding virtual reality or augmented reality image content to the numerical light field image data.

The method of any of the preceding paragraphs, wherein the optical prescription comprises a prescription for myopia.

The method of any of the preceding paragraphs, wherein the optical prescription comprises a prescription for hyperopia.

The method of any of the preceding paragraphs, wherein the optical prescription comprises a prescription for astigmatism.

The method of any of the preceding paragraphs, wherein the optical prescription comprises information regarding higher-order aberrations of the user's eye.

The method of any of the preceding paragraphs, further comprising receiving light from the user's surroundings and generating the numerical light field image data using a light field camera, wherein the light field camera comprises an integral imaging camera with a two-dimensional array of micro-lenses and a corresponding two-dimensional array of photodetectors.

The method of any of the preceding paragraphs, wherein the light field display comprises an integral imaging display with a two-dimensional array of micro-lenses and a corresponding two-dimensional array of light sources.

The method of any of the preceding paragraphs, further comprising projecting infrared light into the user's eye to measure the optical prescription.

The method of any of the preceding paragraphs, further comprising generating the modified numerical light field image data in real-time.

The method of any of the preceding paragraphs, further comprising generating the optical prescription.

The method of the preceding paragraph, wherein generating the optical prescription comprises: computationally introducing a first test amount of positive or negative optical power to the numerical light field image data; receiving feedback from the user regarding the first test amount of positive or negative optical power; and computationally introducing a second test amount of positive or negative optical power to the light field image data.

The method of any of the preceding paragraphs, further comprising generating the modified numerical light field image data by computationally removing one or more light rays which would interact with a defect in the user's cornea or crystalline lens if generated as part of the physical light field.

Correction of Chromatic Aberration

In various embodiments, the light field processor system 600 may be used to at least partially correct or compensate for chromatic aberrations. Chromatic aberrations are those which result from different wavelengths of light interacting differently with the optics of the light field processor system or the eye of the user. Chromatic aberrations are typically caused by the fact that the refractive indexes of optical materials usually vary somewhat as a function of the wavelength of light. There are generally two types of chromatic aberrations: longitudinal chromatic aberrations and lateral chromatic aberrations. Longitudinal chromatic aberrations occur when different wavelengths of light focus at different distances from a lens. Lateral chromatic aberrations occur when different wavelengths of light are focused to a different position on the focal plane of an optical system. Chromatic aberration can cause the color components of an image to be shifted or displaced relative to each other.

The light field image data that is to be projected by the light field processor system 600 and viewed by a user may typically comprise multiple color components. The different color components of the image data may be projected using light of different wavelengths. For example, color light field image data may include a red component, a green component, and a blue component (though different numbers of color components can be used, as too can different color primaries). In some embodiments, the light field processor system 600 may be configured to compensate for longitudinal chromatic aberrations by changing the focus of light of different wavelengths. As already discussed, the light field processor system 600 can computationally adjust the focus of light field image data by introducing positive or negative optical power. By computationally introducing positive or negative optical power to the light field image data on a color-by-color basis (i.e., computationally introducing a first amount of optical power to a first color component and a different second amount of optical power to a second color component, etc.), the light field processor system 600 can adjust the focus of the different colors of the image data so as to at least partially reduce longitudinal chromatic aberration.

In addition, the light field processor system 600 can be configured to computationally alter the angles at which different colors of light are projected so as to at least partially reduce lateral chromatic aberrations. The amount of this angular shift can be different for different color components. In some embodiments, changes to the projection angles for the color components are constant across the entire image, while, in other embodiments, changes to the projection angles for the color components may vary as a function of position in the image.

In some embodiments, the light field processor system 600 may be configured to compensate for chromatic aberrations based on an optical prescription of the user, or based on chromatic aberrations introduced by the optics of the light field processor system 600 itself, or both.

The eye of the user may impart chromatic aberrations to the image data received at the retina. Chromatic aberrations caused by the eye may be determined based on an optical prescription. The optical prescription may comprise a prescription for longitudinal chromatic aberrations and/or lateral chromatic aberrations. In some embodiments, the light field processor system 600 itself can determine an optical prescription of the user. Additionally, or alternatively, the system may include a user interface whereby the user inputs an optical prescription or the light field processor system 600 may go through an eye-prescription configurator program to determine chromatic aberrations of the eye. In some embodiments, as described herein, the light field processor system 600 may be configured to objectively monitor and dynamically adjust (e.g., in real-time) the user's optical prescription based on inputs received from the biofeedback system.

Similarly, the light field processor system 600 may also impart chromatic aberrations to the light field image data which passes through its optics. Chromatic aberrations caused by the system 600 may be determined based on the specifications, manufacturing requirements, and/or characterization measurements of the system. The light field processor system 600 may be configured to at least partially compensate for these pre-determined aberrations when projecting an image to the eye of the wearer.

Once information about the chromatic aberrations introduced by the user's eye and/or the light field processor system 600 itself are known, the system can select an appropriate image modification program to apply to the image data projected to the user by the display of the light field processor system 600. As discussed further below, the image modification program may, for example, change the focus of one or more color components of an image to compensate for longitudinal chromatic aberrations. In another embodiment, alternatively or in combination, the image modification program may change the projection angles of one or more color components of an image to compensate for lateral chromatic aberrations.

The light field processor 70 may be configured to correct for chromatic aberration by providing a different amount of optical power for each of the color components of the light field image data to be displayed to the user. For example, the light field processor 70 could be configured to computationally provide a first optical power adjustment for a first color component of the light field image data. The light field processor 70 could be configured to computationally provide a second optical power adjustment, different from the first optical power adjustment, for a second color component of the light field image data. Similarly, the light field processor 70 could be configured to computationally provide a third optical power adjustment, different from the first and second optical power adjustments, for a third color component of the light field image data. Any of the optical power adjustments could be a positive or negative. The specific amount of optical power adjustment provided to any color component of the image data can be selected so as to bring the respective focal planes associated with the color components of the image data closer together. In this way, the focal depth of each color component of an image may be selectively altered to reduce longitudinal chromatic aberration.

In some embodiments, the light field processor 70 may be configured to computationally vary the projected angle or position of different color components of the light field image data. The projected angles/positions may be varied so as to substantially align the different color components of the image data. In some embodiments, the light field processor 70 may computationally alter the projection angle and/or position for a first color component of the light field image data by a first adjustment amount. The same can be done for other color components of the image data (i.e., the projection angle and/or position for a second color component can be computationally altered by a second adjustment amount and the projection angle and/or position for a third color component can be computationally altered by a third adjustment amount) so as to reduce lateral chromatic aberration.

After selecting an appropriate image modification program to carry out the foregoing adjustments, the light field processor system 600 may apply the image modification program to computationally compensate for chromatic aberrations in the projected light field image data. This can be done on a real-time basis. When the system 600 compensates for chromatic aberrations, not all the chromatic aberration need necessarily be removed. For example, some chromatic aberrations may contribute to creating a realistic focus of depth cue for a given user. Thus, the compensation of chromatic aberration may be controlled to permit some aberrations while correcting others to provide improved or optimal vision quality.

The following paragraphs describe various example embodiments of the devices, systems, and methods described herein.

A wearable ophthalmic device, comprising: an outward facing head-mounted light field camera configured to receive light from a user's surroundings and to generate numerical light field image data, the numerical light field image data comprising multiple color components; a light field processor configured to computationally modify the numerical light field image data to generate modified numerical light field image data, different ones of the color components being modified differently so as to at least partially compensate for chromatic aberration; and a head-mounted light field display configured to generate a physical light field corresponding to the modified numerical light field image data.

The device of the preceding paragraph, wherein the chromatic aberration comprises longitudinal chromatic aberration.

The device of the preceding paragraph, wherein the light field processor is configured to computationally introduce a first amount of optical power to a first color component of the numerical light field image data, and to computationally introduce a second amount of optical power to a second color component of the numerical light field image data, the second amount of optical power being different from the first amount of optical power.

The device of the preceding paragraph, wherein the first amount of optical power and the second amount of optical power cause a difference between a focal plane of the first color component and a focal plane of the second color component to be reduced.

The device of any of the preceding paragraphs, wherein the chromatic aberration comprises lateral chromatic aberration.

The device of the preceding paragraph, wherein the light field processor is configured to project a first color component of the light field image data at a first angle and to project a second color component of the light field image data at a second angle that is different from the first angle to compensate for the lateral chromatic aberration.

The device of any of the preceding paragraphs, wherein the color components of the light field image data are modified based on an optical prescription for an eye of the user.

The device of any of the preceding paragraphs, wherein the color components of the light field image data are modified based on a measurement of the chromatic aberration of the device.

The device of any of the preceding paragraphs, wherein the color components comprise red, green, and blue color components.

A method for using a wearable ophthalmic device, the method comprising: receiving light from a user's surroundings and generating numerical light field image data using an outward facing head-mounted light field camera, the numerical light field image data comprising multiple color components; computationally modifying the numerical light field image data to generate modified numerical light field image data using a light field processor, different ones of the color components being modified differently so as to at least partially compensate for chromatic aberration; and generating a physical light field corresponding to the modified numerical light field image data using a head-mounted light field display.

The method of the preceding paragraph, wherein the chromatic aberration comprises longitudinal chromatic aberration.

The method of the preceding paragraph, further comprising using the light field processor to computationally introduce a first amount of optical power to a first color component of the numerical light field image data, and to computationally introduce a second amount of optical power to a second color component of the numerical light field image data, the second amount of optical power being different from the first amount of optical power.

The method of the preceding paragraph, wherein the first amount of optical power and the second amount of optical power cause a difference between a focal plane of the first color component and a focal plane of the second color component to be reduced.

The method of any of the preceding paragraphs, wherein the chromatic aberration comprises lateral chromatic aberration.

The method of the preceding paragraph, further comprising using the light field processor to project a first color component of the light field image data at a first angle and to project a second color component of the light field image data at a second angle that is different from the first angle to compensate for the lateral chromatic aberration.

The method of any of the preceding paragraphs, wherein the color components of the light field image data are modified based on an optical prescription for an eye of the user.

The method of any of the preceding paragraphs, wherein the color components of the light field image data are modified based on a measurement of the chromatic aberration of the device.

The method of any of the preceding paragraphs, wherein the color components comprise red, green, and blue color components.

Correction of Presbyopia

In some embodiments, the light field processor system may be used to compensate for presbyopia. Presbyopia is a reduction in the amplitude of accommodation of the crystalline lens of the eye, and is typically associated with aging. For close objects, ciliary muscles change the shape of the crystalline lens to provide accommodative power which focuses the light received by the eye onto the retina to form an image thereon. With age, the ability of the crystalline lens of the eye to change shape and accommodate for near distance viewing is diminished. Conventionally, presbyopia is treated by using a multi-focal corrective lens system that comprises a divided lens (e.g., bifocals, trifocals, etc.), or by using lenses with a continuous focal length gradient (e.g., progressive lenses) or variable focus mechanically-deformable or liquid crystal lenses.

In some embodiments, the light field processor system 600 may be configured to assist with presbyopia. In various embodiments, the light field processor system 600 can computationally function as a variable focus lens. As described above, for example, in correcting for myopia, hyperopia, or astigmatism, the light field processor system 600 may apply computational transforms on the captured light field image data to add spherical wavefront curvature which can be dynamically altered by varying the computational transforms which are applied. By using the light field processor 70 to add positive spherical power for near distance viewing, the system can provide presbyopia correction. The added correction for near distance viewing can be applied to the light field image data of the entire field of view or just a portion of it (e.g., a lower portion of the field of view).

In some embodiments, the user may be able to manually adjust the focusing power added to the captured light field by the light field processor 70. For example, in some embodiments, the light field processor system 600 may have a feedback mechanism (e.g., user interface controls) to increase or decrease the optical power which is computationally applied to the captured light field by the light field processor 70. The user can provide feedback based on the focus of the image data being presented to him or her.

Alternatively or additionally, the light field processor system 600 may be configured to automatically or interactively adjust the optical power added by the light field processor 70 based on subjective or objective measurements of the user's eyes. For example, in some embodiments, the light field processor system 600 includes one or more eye tracking cameras or imaging systems to track the eyes. Such cameras and/or imaging systems can monitor the orientation of the eyes and the corresponding direction of the line of sight of the respective eyes. For example, if the user's eyes are looking downward, the user may be looking at a nearby object, such as a book, or may be looking at projected image content corresponding to images placed in a location (lower part of field of view) typically associated with nearby objects. The gaze may also be determined based the vergence of the eyes—how the lines of sight of the pair of eyes converge on a location and how far that location is with respect to the wearer. Accordingly, by monitoring the vergence, the distance at which the viewer is intending to view an object may be determined. When the light field processor system 600 detects that the user is looking down or viewing a nearby object, the light field processor 70 can add spherical power to the captured light field image data to help correct for presbyopia.

In some embodiments, the light field processor system 600 may include sensors that detect the user's head position. In one embodiment, the distance at which the viewer is intending to view an object may be estimated or detected based on a user's head position (e.g., head pose, or orientation). For example, if the user's head is tilted forward and/or downward the wearer may be looking at a relatively close object such as a book or may be looking at projected image content corresponding to images placed in a location (lower part of field of view) typically associated with nearby objects.

In some embodiments, the light field processor system 600 may comprise a sensor assembly 39 with one or more accelerometers, gyroscopic sensors, etc. configured to determine a user's head positions (e.g., head pose or head orientation—straight, tilted down, looking up, etc.) and/or head movements, as discussed elsewhere herein. The light field processor system 600 may also include a processor 32 (e.g., a head pose processor) operably coupled to the sensor assembly 39 and configured to execute digital and/or analog processing to derive head positions, head pose, and/or orientation from movement detected by the sensor assembly 39. In one embodiment, the sensor assembly 39 may generate movement data stored in a digital memory. In some embodiments, the movement data may be used to reduce signal noise while diagnosing visual defects (e.g., detecting a head movement during a test may be indicative of a faulty test and result). The processor 32 may retrieve this movement data and execute processing logic to determine head positions (e.g., head pose or orientation).

In one or more embodiments, gaze orientation may also be based on tracking eye movement through an eye tracking system. In one embodiment, the prescription may be correlated with a set of user eye convergence points that are indicative of a focus depth of the eye. For example, while the user's head position may be unchanged, the user's eyes may be tracked to a convergence point that is below the horizon. Such movement may be indicative of the eye focusing on an object located at a near-field focal depth. Also, as discussed above, the vergence of the eyes can assist in determining the distance at which the viewer is directing his or her attention (e.g., focusing). This distance may be ascertained from the convergence of the lines of sight of the eyes. Accordingly, in various embodiments, the user's eyes may be tracked to a convergence point at a particular distance from the wearer.

Likewise, in various embodiments, the light field processor system may be configured to determine a focal depth at which the eyes are focused or accommodated. In some embodiments, eye-tracking system may be used to triangulate the user's convergence point and adjust the focus of the images to be presented to the user accordingly. For example, the eye-tracking system may determine a direction along which each eye is viewing (e.g., a line extending from each eye) and determine a convergence angle where the directions intersect. The convergence point may be determined from the determined angle of convergence. In some embodiments, the eye-tracking system may be included as part of the biofeedback system. As described above, in various embodiments, the light field processor system may utilize cameras 24 paired with light sources 26 (e.g., an infrared light source and infrared camera) to track the position of each eye, which can be operatively coupled to the local processing module 70. The local processing module 70 may include software that, when executed, may be configured to determine the convergence point of the eyes. From this determination, the light field processor system may also execute logic device to determine a focus location or depth based on the orientation or direction of the user's gaze.

In another embodiment, gaze orientation may be determined through glint detection. The eye tracking system may be configured to discern one or more glints or reflections from the eye and determine a position of the one or more glints on the eye relative to the features of the eye (e.g., pupil, cornea, etc.). As the eye is moved, the relative position of the glint on the eye may change. For example, if a glint is located at the top of an eye and the space between the glint and the pupil increases, this may be indicative that the gaze orientation has tilted downward, the eyes may be accommodating at a near-field focal depth.

Figure 12:
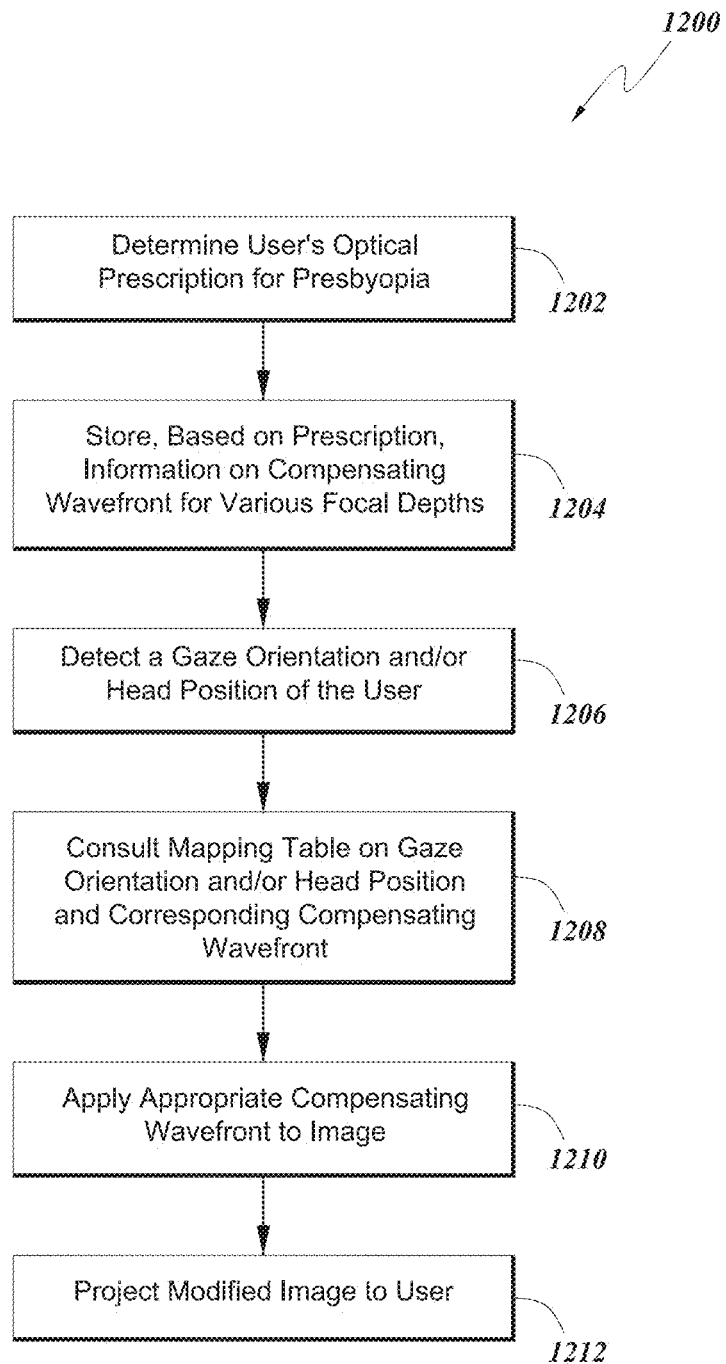
FIG. 12 shows an example method for using the light field processor system to correct presbyopia.

FIG. 12 shows an example method for using the light field processor system 600 to correct presbyopia. The method 1200 is directed to modifying light field image data presented to the user based on a prescription of the user. In some embodiments, method 1200 may be performed by patient-worn ophthalmic devices, such as those described in connection with FIGS. 3A-5. In various embodiments, the light field processor system described in FIGS. 6 and 7 may be used to provide correction for presbyopia based on the user's optical prescription.

At 1202, a presbyopia prescription is determined for the user. The prescription may be determined by receiving information from the user, or may be determined by the light field processor system itself by adjusting the wavefront presented to the user and the user selecting a desired prescription. For example, the light field processor system may be configured to test for an optical prescription for different focal planes of accommodation. In some embodiments, the light field processor system may be pre-programmed with discrete granular steps in altering wavefronts of light field image data presented to the user through the display device 62 for a plurality of focal depths. For example, the light field processor system may employ phoropter technology, as described herein. The prescription may be entered by the user through a user interface and may be stored in the remote data repository 74. The prescription may be retrieved by one or more processors of the light field processor system, for example, remote processing module 72.

In another embodiment, the light field processor system may automatically and possibly incrementally change the user's prescription via the biofeedback system. The biofeedback system may be configured to determine a comfort level of the user in viewing an object or image. For example, if a user's eyes are unstable, shifting, oscillating, changing accommodation (e.g., in an unsteady or random manner), etc., these may be indicators that the user is unable to comfortably view the object. Accordingly, the accommodation, vergence, pupil size, etc., may be monitored and/or an autorefractor or other device (e.g., scanning laser ophthalmoscope (SLO)) may be used to see if an image is focused on the fovea of the retina.

In some embodiments, the light field processor system may be configured to receive an optical prescription for presbyopia correction (e.g., the added optical power) from a third party. For example, a doctor may be able to send a user's optical prescription wirelessly (e.g., over the internet, Blue-tooth connection, hospital network, etc.), which is received by a receiver or transceiver and stored in the digital memory of the local processing module 70.

At 1204, the system may store information on compensating wavefronts. The compensating wavefronts may be based on the optical prescription of the user for various focal depths of accommodation. In some embodiments, the information may be input parameters for varying the focal depth.

In some embodiments, each corrective function comprises a set of input parameters that define adjustments to achieve the desired wavefront correction. The input parameters may be based on the optical prescription for correcting a user's presbyopia when the wearer is focusing at a near-field focal depth. The system may correlate different viewing distances and corresponding corrective functions to compensate for refractive errors associated with accommodating at varying focal depths. Accordingly, different convergence points and focal depths of accommodation may be correlated with different prescription correction.

In some embodiments, this information may further be correlated with a set of head positions (e.g. head poses, orientations), and/or gaze directions. For example, if the user's head is tilted downward, the eyes may be accommodating at a certain (e.g., closer) focal depth. Accordingly, in various embodiments, programs specific for presbyopia may be pre-programed into the light field processor system (or downloaded) such that the right head position (e.g., head pose, orientation) and/or gaze orientation can be matched correctly with an amount of presbyopia correction. Different gaze directions and head orientations can be correlated with different prescription correction for assisting accommodation. The light field processor system thus may be configured to provide a different optical correction depending on a measured gaze direction and/or head position, head pose, or orientation.

At 1206, the system may detect, through gyroscopes, accelerometers, inertial measurement units (IMUs), other sensors, or combinations thereof, an orientation of the user's gaze and/or head position, head pose, or orientation. The gaze orientation (e.g., including the convergence point of the eyes) and/or head position, head pose, or orientation may be indicative of whether the wearer is viewing near or far and thus whether the wearer needs to accommodate, as described above. Accordingly, different corrective functions may be used for different focal depths of accommodation.

In some embodiments, the light field processor system comprises a sensor assembly 39, processor 32, and head pose processor 36 which may be configured to detect movement, tilt, and orientation of the user's head. In some embodiments, sensors may be operably coupled to the local processing module 70, which may execute logic to retrieve the detected head movement and/or determined head position, head pose, or orientation. A downward movement of the user's head may be indicative of focusing on an object in the near-field.

In some embodiment, the gaze orientation may be based on tracking the eye movement, as described above. For example, downward movement of one or more eyes of the user may be indicative of focusing on an object in the near-field (e.g., shifting view from the horizon to a book held below the horizon). Thus, if the eye tracking system determines that the user's eyes have shifted downward, an appropriate corrective function may be determined based on the presbyopia prescription. In another embodiment, the eye tracking system may be configured to determine whether the angle of convergence is increasing (i.e., the convergence point is becoming closer to the user). Such determination may be indicative of focusing on an object in the near-field. Thus, the light field processor system may be able to determine focal depth of accommodation.

In some embodiments, the system may utilize cameras 24 to track the position of each eye, which can be operatively coupled to the light field processor 70. In another embodiment, the system may utilize cameras 24 to perform glint detection and monitoring, in which, for example, the camera 24 tracks the position of a glint with respect to features of the eye (e.g., edge of the eye, intersection of the eye with an eye lid, pupil, etc.). The light field processor 70 may include software that, when executed, may be configured to track eye movement, glint movement, and/or determine the convergence point of the eyes. In some embodiments, the gaze orientation may be stored in the remote data repository 74.

In some embodiments, the remote processing module 72 may be configured to correlate gaze orientation, angle of convergence, and/or head position information with the optical prescription, all of which information may be stored locally or in the remote data repository 74.

At 1208, based on the detected gaze orientation and/or head position, the system consults the mapping table (e.g., the information stored at 1204) to determine an appropriate corrective function to computationally apply to the captured light field image data to produce compensated wavefronts. For example, based on the gaze orientation or direction and/or head position, the system may determine a focal depth at which the eye is accommodating. In various embodiments, the optical prescriptions may be correlated with one or more focal depths associated with accommodation. For example, different convergence points or focal depths associated with different amounts of accommodation may be correlated with a different optical prescriptions and corrective functions.

In various embodiments, at 1208, the system may retrieve the detected focal depth of accommodation and may consult the mapping stored at 1204. Based on the mapping, the system may determine the appropriate corrective function for that identified focal depth.

In some embodiments, the light field processor 70 may retrieve the detected gaze orientation stored in a digital memory at 1206. Or, it may receive the detected gaze orientation directly from the eye tracking system, sensor assembly 39, and/or head pose processor 36. The light field processor 70 may execute logic to access the mapping table stored at 1206 and, based on the gaze orientation, angle of convergence, and/or head position, select an appropriate corresponding corrective function to be computationally applied to the collected light field image data to compensate for the presbyopia.

At 1210, the appropriate compensating wavefront (e.g., positive spherical power) is computationally applied to the collected light field image data. At 1212, the modified light field image data is presented to the user. The processed light field image data may have wavefronts that are modified based on the selected corrective functions as applied at block 1210.

Accordingly, the method 1200 may be implemented to dynamically correct a user's presbyopia. The correction applied by the light field processor can be dynamically reconfigured (e.g., reconfigured in real-time as the optical prescription of the user changes and hence is repeatedly updated during use of the light field processor system). For example, the presbyopia prescription correction may be adjusted at a variety of intervals in time. The light field processor system may therefore be configured to dynamically correct for changes in a user's presbyopia prescription. The interval may be predetermined and based on an expected rate or occurrence of vision defects, deterioration, or changes. For example, the presbyopia of a user may change as the user ages.

In some embodiments, at 1210 the light field processor system may implement an eye-prescription configuration program. At 1210, the light field processor system can be configured to return to block 1202 to update or adjust the prescription based on inputs from the biofeedback system, as described above, to manually and interactively determine the user's prescription at each interval, without user activation. Such procedures can be scheduled by a protocol (e.g., configured to check once a month, a couple times a year, etc.) or when it is determined that vision—near vision for example—is deteriorating. In another embodiment, as described above, the biofeedback system may monitor movements and changes in the eye of the user (e.g., via camera 24 and light source 26) to determine that the user is struggling to accommodate. For example, the light field processor system may monitor vergence, pupil dilation, and/or movement and/or shape of the natural lens of the eye. The light field processor system may also use an autorefractor, or other technology as described herein, to monitor an image formed on the fovea of the retina. The light field processor system may then initiate an eye-prescription configuration program to determine a new optical prescription and/or adjust the corrective function (e.g., update the mapping table of focal depths and corrective functions).

In one or more embodiments, the light field processor system may allow the user to manually adjust the focus of one or more images presented to the user. For example, the system may be pre-programed with discrete steps in adjusting focus. The user may then specify the desired focus to the light field processor system through a user interface. In some embodiments, the user may have the option of incrementally increasing or decreasing a prescription (e.g., changing the focus) until the user arrives at a comfortable viewing focus. Or, the light field processor system may possibly incrementally increase or decrease a prescription automatically by utilizing the biofeedback system and other diagnostic technologies (see e.g., the description of phoropter and autorefractor technology herein). In some embodiments, such user input prescriptions may be associated with a particular gaze or head orientation and may be provided when the wearer has such a gaze or head orientation. But in some embodiments, such user input prescriptions may be applied independent of the gaze or head orientation and are not changed with change in gaze, line of sight, and/or head orientation.

The following paragraphs describe various example embodiments of the devices, systems, and methods described herein.

A wearable ophthalmic device, comprising: an outward facing head-mounted light field camera configured to receive light from a user's surroundings and to generate numerical light field image data; a light field processor configured to generate modified numerical light field image data by computationally introducing an amount of optical power to the numerical light field image data based on a viewing distance from the user to an object in the numerical light field image data; and a head-mounted light field display configured to generate a physical light field corresponding to the modified numerical light field image data.

The device of the preceding paragraph, further comprising a head-mounted accelerometer sensor to determine the user's head orientation, wherein the viewing distance is estimated based on the user's head orientation.

The device of any of the preceding paragraphs, further comprising one or more head-mounted eye tracking cameras to determine the user's gaze direction, wherein the viewing distance is estimated based on the user's gaze direction.

The device of any of the preceding paragraphs, further comprising one or more head-mounted eye tracking cameras to determine a convergence point of the user's gaze, wherein the viewing distance is estimated based on the convergence point of the user's gaze.

The device of any of the preceding paragraphs, wherein the amount of optical power is based on an optical prescription for the user.

The device of any of the preceding paragraphs, wherein the light field camera comprises an integral imaging camera.

The device of any of the preceding paragraphs, wherein the light field display comprises an integral imaging display.

The device of any of the preceding paragraphs, further comprising a manual control to specify the amount of optical power to introduce to the numerical light field image data.

The device of any of the preceding paragraphs, wherein the light field processor is configured to introduce the amount of optical power to the entire field of view of the numerical light field image data.

The device of any of the preceding paragraphs, wherein the light field processor is configured to introduce the amount of optical power only to a lower portion of the field of view of the numerical light field image data.

A method for using a wearable ophthalmic device, the method comprising: receiving light from a user's surroundings and generating numerical light field image data using an outward facing head-mounted light field camera; generating modified numerical light field image data by computationally introducing an amount of optical power to the numerical light field image data using a light field processor, the amount of introduced optical power being based on a viewing distance from the user to an object in the numerical light field image data; and generating a physical light field corresponding to the modified numerical light field image data using a head-mounted light field display.

The method of the preceding paragraph, further comprising determining the user's head orientation using a head-mounted accelerometer sensor, wherein the viewing distance is estimated based on the user's head orientation.

The method of any of the preceding paragraphs, further comprising determining the user's gaze direction using one or more head-mounted eye tracking cameras, wherein the viewing distance is estimated based on the user's gaze direction.

The method of any of the preceding paragraphs, further comprising determining a convergence point of the user's gaze using one or more head-mounted eye tracking cameras, wherein the viewing distance is estimated based on the convergence point of the user's gaze.

The method of any of the preceding paragraphs, wherein the amount of optical power is based on an optical prescription for the user.

The method of any of the preceding paragraphs, wherein the light field camera comprises an integral imaging camera.

The method of any of the preceding paragraphs, wherein the light field display comprises an integral imaging display.

The method of any of the preceding paragraphs, further comprising receiving the amount of optical power to introduce to the numerical light field image data from a manual control.

The method of any of the preceding paragraphs, further comprising introducing the amount of optical power to the entire field of view of the numerical light field image data.

The method of any of the preceding paragraphs, further comprising introducing the amount of optical power only to a lower portion of the field of view of the numerical light field image data.

Correction of Strabismus/Amblyopia

Another common visual ailment is strabismus, which is an inability of both eyes to align at a single convergence point in order to produce a fused stereo image. This typically results from an eye with weakened ocular muscles being unable to coordinate its motions with that of its normal counterpart. Similarly, amblyopia is a visual ailment where there is decreased vision in one or both eyes. This decreased vision may be caused by abnormal development of vision in infancy or during childhood. Amblyopia is sometimes referred to as a "lazy eye."

In some embodiments, a wearable light field processor system 600 may be used to treat or correct convergence deficiencies, such as deficiencies resulting from strabismus or amblyopia. As an example, if the convergence is offset in an angular fashion, a compensating prism correction may be computationally applied to bring the convergence point of both eyes together. The compensating prism correction may be computationally applied by the light field processor to the collected light field image data.

Where the convergence of both eyes is offset angularly, one or more of the following techniques may be used. In some embodiments, an eye tracking system may determine a gaze vector and/or a point of focus of a healthy eye. This information may be extrapolated to determine a targeted convergence point for both eyes. In certain embodiments, an eye tracking system and a depth sensing system may be used in conjunction to determine the convergence point of both eyes. In certain implementations, muscles of one or more eyes may be "re-trained" through a treatment protocol to gradually align the focus and/or convergence point of both eyes. The treatment protocol can include the methods described herein, including methods that are designed to strengthen muscles of a weaker eye and/or to stimulate neural responses to optic signals from a weaker eye.

The light field processor system 600 can be configured to selectively introduce a prismatic effect or an angular shift in images provided to the wearer. This can be done in a number of ways and for different purposes. For example, a computational compensating prism correction can be applied as an optical correction for the wearer (e.g., to compensate for convergence deficiencies in one or both eyes of the wearer). This correction can be applied to collected light field image data to account for the deficiencies of the wearer so that the wearer can achieve or approximate binocular single vision even where the wearer suffers from strabismus and/or amblyopia.

The compensating prism correction can be achieved by adjusting the locations of image data provided to the wearer. The light field processor can achieve this by laterally shifting (orthogonal to the normal line of sight or normal to the optical axis) the locations of the images presented in the display (as compared to where the image data would be projected in the absence of such intervention). The system 600 can be configured to detect the focal point or the alignment of the eyes of the wearer and to adjust the positions of the respective left and right images to be at a targeted point within the field of view of each eye. For example, the system 600 can include eye tracking to determine the gaze of each eye. When the gaze is determined, the system can be configured to position respective left and right images centered within the field of view of the respective left and right eyes. In some embodiments, to re-train a weaker eye, the system can gradually move the image presented to the weaker eye towards a desired or targeted convergence point. In this way, the weaker eye can be re-trained to properly look at the same point as the strong eye.

To determine the amount of prism correction to computationally apply, the light field processor system 600 can be configured to monitor where the image and light were being projected on the retina of the weak eye of the wearer. (This can be done using integrated eye imaging capabilities, as described herein.) If the prism correction allows the light to shine on a desired portion of the retina, then it is correct. If not, more or less is needed. As described herein, autorefractor technology, or other technologies (e.g., scanning laser ophthalmoscopy (SLO)), can be used to determine if the compensating prism correction has reduced or corrected the misaligned vision of the wearer. In some embodiments, the system 600 is configured to determine (or receive input indicating) whether the user has an exotropic or esotropic deviation. Once this deviation is known by the device, prism corrections can be computationally applied to the light field image data until the vision defect is substantially corrected. This may be determined automatically or it can be determined based on user input. In some embodiments, to determine a correct or suitable prism correction automatically, the system 600 can include one or more inward-facing cameras to measure angular deviation (e.g., a shift in fixation) and use the display to occlude one eye while changing the prism prescription in the other. In some embodiments, to determine a correct or suitable prism correction using user input, the system 600 can be configured to implement a test similar to a Maddox rod test. For example, the system 600 can provide a digital filter to filter light for the test. As another example, the system 600 can provide image sources from two different depth planes. (This can be done using light sources 714 which are configured to project light into the eye of the wearer.) Based on user input, the system 600 can adjust the prism correction until satisfactory conditions are met (e.g., a first image is aligned with a second image).

As another example, a computational compensating prism correction can be applied for a therapeutic purpose (e.g., to gradually re-train the eyes to arrive at a targeted convergence point). Methods for re-training eyes that emphasize the presentation of images of differing characteristics to respective eyes of the wearer are also discussed herein.

In some embodiments, the light field processor system 600 includes an eye tracking system. The eye tracking system can be configured to determine gaze of the wearer's eyes. The eye tracking system can include one or more sensors configured to sense properties of the eyes of the wearer. In some embodiments, the one or more sensors include cameras, as described herein. In various embodiments, the one or more sensors including cameras can be configured to image the glint and/or Purkinje images to determine a gaze. The eye tracking system can include an analysis module configured to determine a direction of gaze of the wearer's eyes based at least in part on the information acquired with the one or more sensors.

In some embodiments, the system 600 includes one or more outward facing cameras. In certain implementations, the one or more outward facing cameras can be similar to the cameras 16 described herein with reference to FIG. 5.

The system 600 can include one or more user interface features configured to allow a wearer or other person to provide input to the device. The user interface features can be integrated with the system. In some implementations, the user interface features are provided by a device or component that is not physically integrated with the system. For example, the user interface features can be provided by a device or system that is in communication with the device. This can be a smartphone, computer, tablet, or other computational device that is in wired or wireless communication with the device. In some embodiments, the user interface features can be provided by a combination of different devices and systems linked to the device (e.g., through wired or wireless communication networks or through components that are physically linked to the device or integrated with the device). The user interface features can be presented on a device with a touch screen wherein interaction with the touch screen provides input to the system 600. Voice recognition and/or virtual touch screen technology can also be employed. The user interface features can include capacitive features sensitive to touch, keyboards, buttons, microphones, photodetectors, or a variety of software-implemented features provided by a graphical user interface. In some embodiments, the user interface features include gesture detection components to allow a wearer to provide user input through gestures. In some embodiments, the user interface features include gaze detection components to allow a wearer to provide user input through gaze of the eyes (e.g., this can include selecting a button or other element when the wearer fixates on the button for a time or when the wearer blinks when fixated on the button). Such systems can be used for other devices and systems described herein. The user interface features can be presented on a device with a touch screen wherein interaction with the touch screen provides input to the wearable light field processor system.

In some implementations, the wearer, clinician, doctor, or other user can use the interface features to control aspects of the vision testing and/or therapy. This can be done, for example, to change the amount of computational prism correction applied, the amount of computational lateral shift of the images, to modify characteristics of enhanced images, or to otherwise configure testing or treatment of convergence deficiencies.

Figure 13:
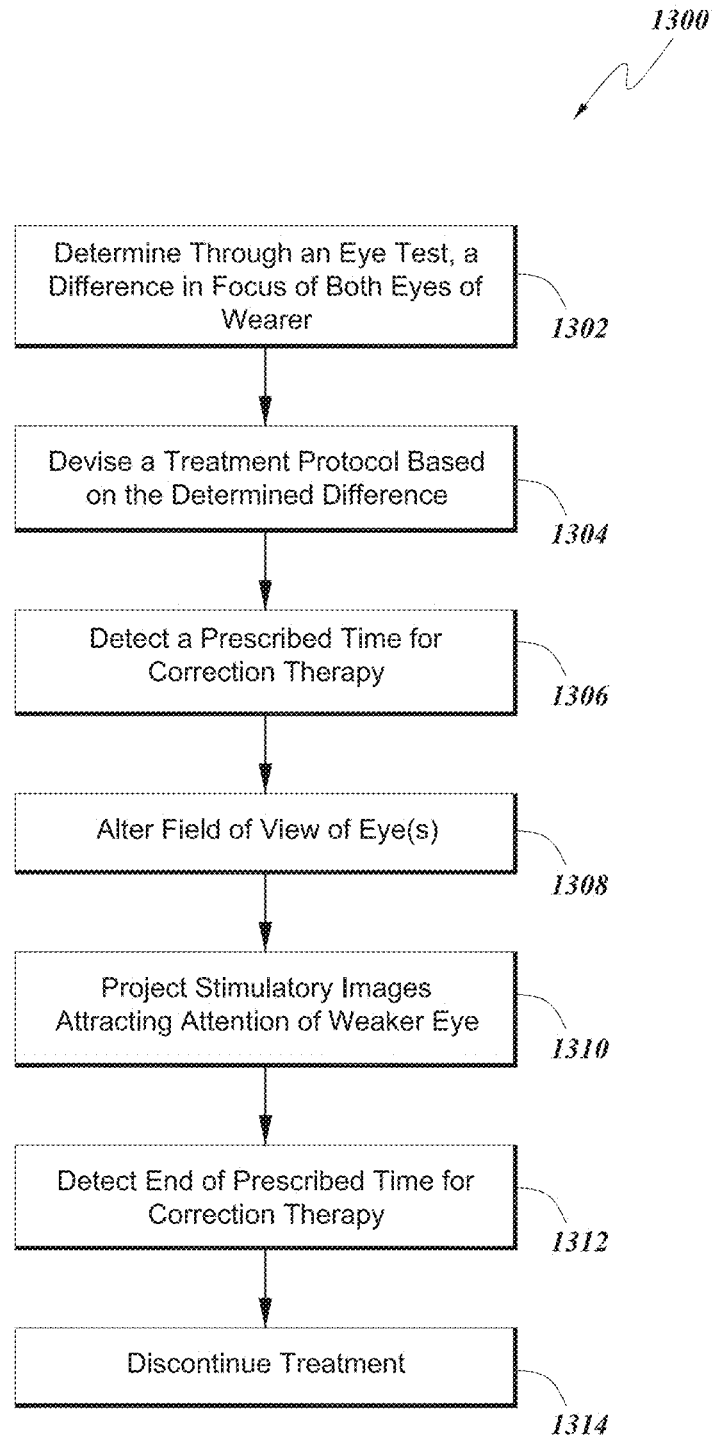
FIG. 13 illustrates an example method for using the light field processor system to treat convergence deficiencies, such as those caused by strabismus and/or amblyopia.

FIG. 13 illustrates an example method 1300 for using the light field processor system to treat convergence deficiencies, such as those caused by strabismus and/or amblyopia. For ease of description, the method 1300 will be described as being performed by a light field processor system 600, as described herein. The method 1300 includes a process of "re-training" a lazy eye or misaligned eyes by occluding or de-emphasizing the stronger eye. It should be appreciated that many treatment protocols may be devised based on a user's particular prescription, and the exact parameters and/or techniques may vary.

At block 1302, the light field processor system 600 determines a difference in the focus and/or convergence points of both eyes. As discussed herein, this difference may be determined based on user input or based on a prescription test performed by the light field processor system. Eye tracking and/or gaze detection can also be used. The light field processor system can be configured, for example, to perform any of the methods described herein for determining focus points and/or convergence points.

At block 1304, the light field processor system 600 selects a treatment protocol to help treat the wearer's visual defect. In some embodiments, the treatment protocol may be devised by a doctor or clinician or the treatment protocol may be devised at an external location and downloaded onto the light field processor system. The treatment protocol may comprise various parameters. For example, the treatment protocol may involve a frequency at which the treatment is administered. The treatment protocol may include information on the type of images to be presented to the wearer and/or differences in the two displays or images shown to each eye. For example, the treatment protocol can be based on a dichoptic presentation where images of differing characteristics are displayed to the wearer (e.g., different images or the same image with the version of the image shown to the left and/or right eyes altered). In some implementations, the image shown to the weaker eye can be enhanced and/or the image shown to the stronger eye can be diminished. For example, the image shown to the weaker eye can be altered to be made more interesting or compelling to the wearer (e.g., brightened, color-enhanced, three-dimensionally enhanced, sharpened focus, higher resolution, enhanced contrast, moving, higher refresh rate, etc.) Similarly, the image shown to the stronger eye can be altered to be less interesting or less compelling to the wearer (e.g., darkened, muted colors, flattened, blurred, lower resolution, lower contrast, static, lower refresh rate, etc.). In various implementations, only the images shown to the weaker eye are altered while the images shown to the stronger eye are not altered. In various implementations, only the images shown to the stronger eye are altered while the images shown to the weaker eye are not altered. In various implementations, the images shown both to the weaker eye and to the stronger eye are altered. The treatment protocol may include information on the duration of the protocol. The treatment protocol may employ interactive virtual objects, thereby making the "treatment" more enjoyable to the user and increasing user compliance to therapy regimen. The treatment protocol may employ dynamic images (e.g., movies, games, etc.) to make the treatment more enjoyable, thereby increasing compliance.

At block 1306, the light field processor system may detect or determine, based at least in part on a scheduler attached to the treatment protocol, a time or time window at which to start the treatment protocol. For example, the treatment protocol may be programmed such that re-training of the eye is to be performed daily at 10 PM or somewhere between 8 AM and 9 AM. The treatment protocol may only be prescribed once every week, for example. The treatment protocol can involve more treatment sessions such as at least twice a week, at least five times a week, every day and/or multiple times of day, such as at least, one, two, three, four, or five times a day. In some embodiments, the treatment protocol may be programmed in response to detecting that the eyes are becoming more or less misaligned. In various embodiments, the treatment protocol may be programmed to occur when the eyes have recovered from the previous treatment protocol.

At block 1308, the light field processor system alters the field of view of one or both eyes. This can include, for example, partially or fully computationally occluding the eye(s) (e.g., by blacking out all or a portion of the image data to be presented to each eye). In some embodiments, the light field processor system may present different images to each eye, sometimes in different locations within the field of view, to either strengthen a weaker eye or promote proper vergence for image fusion within the brain. It should be appreciated that this is simply one example technique, and many other techniques may be used to strengthen or re-train the muscles of the eyes. The occlusion may be a partial or complete occlusion. Full or partial defocus, blurring, attenuation, or other alteration to images presented to the wearer may be used as well.

In some embodiments, the light field processor system may skip block 1308. For example, in some treatment protocols, the respective fields of view of the stronger eye and the weaker eye are not altered. The light field processor system may present images of different visual characteristics to the wearer's eyes to encourage the weaker eye to gain strength.

As described herein, the content shown to the respective eyes can differ as well, whether or not the field of view of one or both of the eyes is altered. For example, more intriguing content can be shown to the weaker eye. This may be accomplished by projecting images to the weaker eye that are brighter, higher resolution, more complete, moving, higher contrast, three-dimensional, color-enhanced, from a plurality of depth planes, etc. As another example, less intriguing content can be shown to the stronger eye. This may be accomplished by projecting images to the stronger eye that are duller, lower resolution, missing portions, static, lower contrast, flattened, color-muted, from a single depth plane, etc. Intriguing content can be projected to the weaker eye at the same time as less intriguing content can be projected to the stronger eye, thereby encouraging the weaker eye to gain strength.

At block 1310, the light field processor system projects stimulatory images attracting the attention of the weaker eye. These stimulatory images may be presented at prescribed locations and/or with enhanced visual characteristics—color saturation, contrast, resolution, depth cues, three-dimensional effects, brightness, intensity, focus, etc., thereby encouraging the eyes to focus and/or converge at a targeted location and/or encouraging the visual content from the weaker eye to strengthen it. The virtual images can be moved over time and at a rate designated by the treatment protocol to draw the eyes together at points of vergence across multiple depth planes. When the eyes align at a common point of vergence, the images from each eye fuse and the brain sees one image instead of two. This may be achieved in the form of a game, for example.

In various embodiments, for example, the light field processor system can be configured to simultaneously present images to both eyes (dichoptic) for treatment or therapeutic purposes. The images presented to respective eyes can differ in visual characteristics. This difference can increase performance of a weaker eye over time. For example, to provide a stereoscopic image to the wearer, left and right images can be presented to the wearer. During treatment, the image corresponding to the weaker eye can be enhanced relative to the stronger eye. Enhancement of the image can include, for example and without limitation, increasing brightness of the image, increasing contrast of the image, increasing color saturation of the image, increasing intensity of the image, increasing three-dimensional effects of the image, adding content to the image, etc. Similarly, the image corresponding to the stronger eye can be diminished. Diminishment of the image can include, for example and without limitation, decreasing color saturation of the image, attenuating or decreasing intensity of the image, flattening the image, blurring the image, de-focusing the image, shadowing the image, partially or completely occluding the image, etc. In certain implementations, de-focusing the image can be accomplished by computationally presenting images to the respective eyes from different depth planes. In some embodiments, treatment can include enhancing images to the weaker eye and diminishing images to the stronger eye. In certain embodiments, treatment can include enhancing images to the weaker eye while not altering images to the stronger eye. In various embodiments, treatment can include diminishing images to the stronger eye while not altering images to the weaker eye. The enhancement and/or diminishment of images can be applied gradually and/or intermittently. For example, the quality of an image can be gradually enhanced or diminished every 30-60 seconds and/or when the light field processor system detects that the eyes have become more misaligned. As another example, an image can be enhanced or diminished for a time period and then that effect can be removed for a second time period. This can be alternated over the treatment period.

Treatment can also include, in some embodiments, varying depth planes from which images are presented. This can be similar to a Brock string where multiple depth planes are used to re-train eyes with convergence deficiencies. Images are projected from various depth planes, thereby allowing the eyes to converge and focus on images at varying depths. Varying depth planes can also be used to provide treatment similar to pencil pushups. This treatment includes presenting an image at a first depth plane (e.g., about 1 foot away or farther) and then moving the image closer to the wearer to a second depth plane. Moving the image can include gradually moving the depth plane closer to the wearer from the first depth plane to the second depth plane. While the image is being presented at this closer depth plane, the depth of the image can be adjusted so that the wearer can practice focusing on the image in a region where it is difficult to focus (e.g., the wearer has difficulties converging on the image). This treatment also includes providing an image at a third depth plane that is farther away than the first and second depth planes. While the image is being presented at the second depth plane, the wearer can alternate between focusing on the image at the second depth plane and the image being presented at the third depth plane. This can strengthen eye muscles, for example. These methods can be combined with enhancement and/or diminishment of images during treatment.

Treatment can include, in some embodiments, selective occlusion of one or both eyes. This can be done to present visually stimulating images at a targeted portion of the retina to increase effectiveness of the treatment. In some embodiments, the light field processor system is configured to use selective occlusion to block portions of objects seen by the wearer. Selective occlusion also includes intermittently occluding images in an eye. This can be done to alternate images to the eyes (e.g., alternate between presenting an image to the left eye and then to the right eye).

Treatment can include, in some embodiments, minor adjustments to a compensating prism correction to gradually influence convergence of the eyes. For example, the amount of compensating prism correction and/or lateral image shift can be reduced during treatment to influence a weaker eye to converge to a targeted point. The amount of compensating prism correction and/or lateral image shift can be reduced over time during a single treatment or over the course of multiple treatments.

At block 1312, the system detects the end of the prescribed time for the treatment protocol, possibly by detecting normal characteristics in the function of the eye for accommodation, vergence, etc. At such time, the light field processor system discontinues treatment at block 1314. This can include terminating occlusion or de-emphasis of the image data provided to the wearer, if occlusion or de-emphasis had been applied. In some embodiments, the wearer may manually administer the treatment protocol based on the wearer's schedule. Similarly, many other such treatment protocols may be envisioned.

In addition, or alternatively, a prescribed treatment protocol can be terminated or adjusted based on monitoring of a performance parameter. When the performance parameter reaches a desired value, state, or range, the treatment protocol can be terminated or adjusted. In some embodiments, the performance parameter is a biofeedback parameter. For example, in some embodiments, at block 1312, the light field processor system determines that the treatment should be discontinued by tracking performance of the wearer during treatment. When the wearer shows signs of fatigue or a lack of compliance, the light field processor system discontinues treatment at block 1314. For example, the light field processor system can include an eye tracking system that is configured to detect gaze of the wearer. The eye tracking system may detect that the wearer's performance during treatment (e.g., the wearer's ability to successfully focus on the images being presented) has deteriorated over time. This may indicate that the wearer is tired and further training or treatment would have limited benefits. In some embodiments, the light field processor system can track the performance of the wearer over time to determine whether the convergence deficiencies of the wearer are decreasing over time (e.g., during a single treatment and/or over multiple treatment sessions). If the lazy eye is drifting more, the system may initiate a stronger therapy. Or if the lazy eye is almost aligned with the strong eye, then the system may terminate treatment.

In some embodiments, at block 1312, the light field processor system receives input from a user, a clinician, or an external source, indicating that the treatment should be discontinued. When such user input is received, the light field processor system discontinues treatment at block 1314.

In some embodiments, at block 1312, the light field processor system automatically detects performance of the user during the administered treatment protocol. In block 1312, the light field processor system can be configured to return to block 1304 to update or adjust the treatment protocol based on the detected performance of the wearer during the administered treatment protocol. For example, if the angle of convergence of the weaker eye does not improve during treatment, the light field processor system can adjust the treatment protocol parameters and proceed with the method 1300 starting again at block 1304. In this way, the light field processor system can use the wearer's performance during testing as feedback to make adjustments to the treatment protocol and/or to determine when to terminate the treatment.

In various implementations, the light field processor system can be configured to terminate the treatment protocol prior to finishing. For example, if the light field processor system detects fatigue in the eye (e.g., the angle of convergence gets worse for weak eye), the light field processor system can be configured to terminate the treatment protocol at block 1312 by proceeding to block 1314.

Amblyopia or "lazy eye" is a condition in which one of the eyes is weaker than the other. This may be caused by the brain's preference to favor the inputs the stronger eye over the weaker. In some embodiments, the light field processor system may be programmed to perform a method similar to the method 1300 described with reference to FIG. 13 to enhance the visual stimulus to, and thereby gradually strengthen, the weaker eye and/or to reproduce the effects of an eye patch by selectively dimming an intensity of light or decreasing the level of visual stimulus entering the stronger eye. Other treatment and training systems and techniques as described above, for example, with reference to Strabismus may also be employed.

In various embodiments, to reduce distraction the view of the world in front of the wearer's eyes through the light field processor system is blacked out or otherwise not visible during examination and/or treatment.

Figure 14:
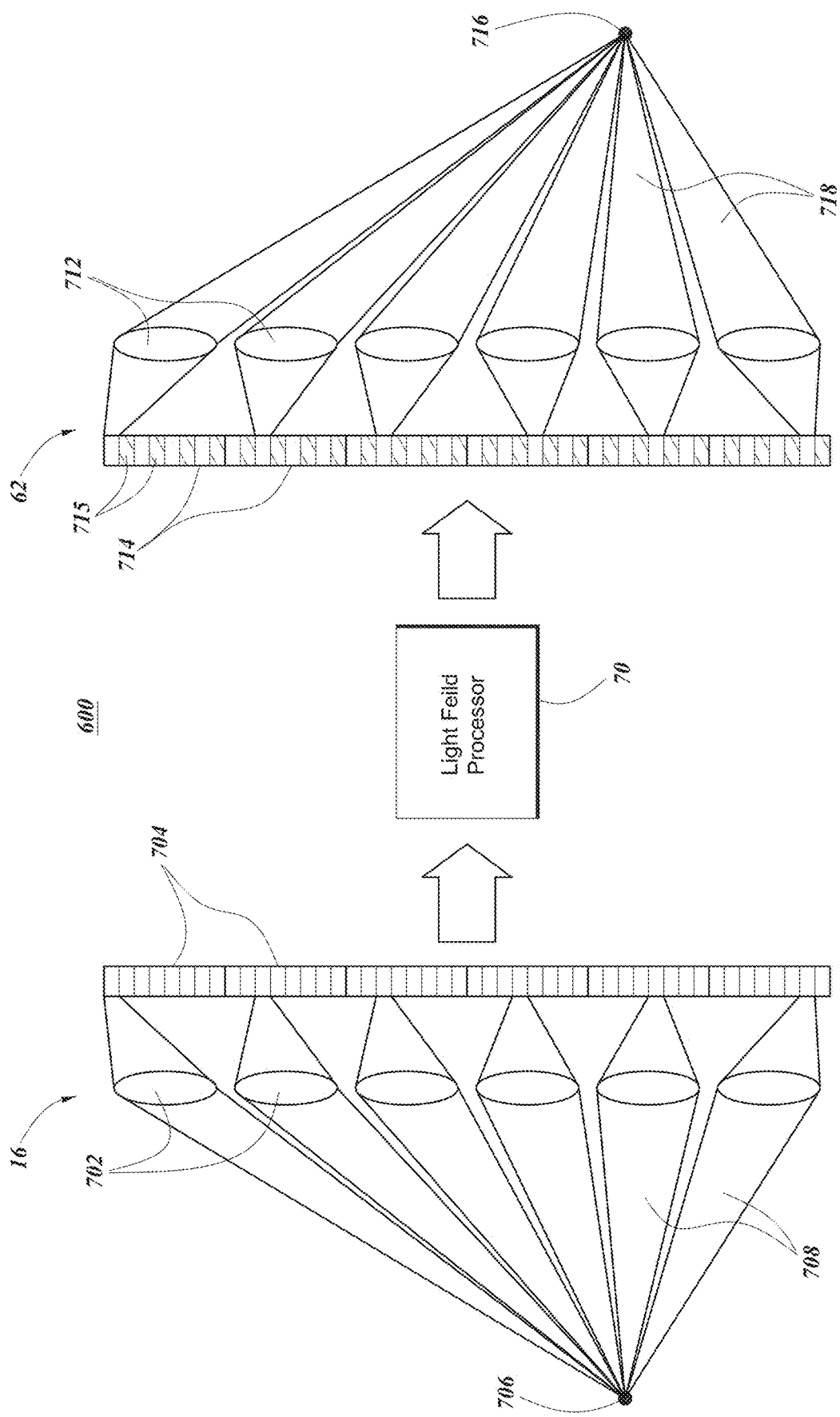
FIG. 14 is a schematic illustration of an embodiment of a light field processor system which includes an outward facing integral imaging camera, a light field processor, and an integral imaging display which also includes one or more photodetectors.

FIG. 14 is a schematic illustration of an embodiment of a light field processor system which includes an outward facing integral imaging camera 16, a light field processor 70, and an integral imaging display 62 which also includes one or more photodetectors. The outward facing integral imaging camera 16 and the light field processor 70 shown in FIG. 14 can be similar to those described elsewhere herein.

As discussed previously with respect to FIG. 7, the integral imaging display 62 includes a two-dimensional array of micro-lenses 712 and a two-dimensional array of light sources 714. The array of light sources 714 can be, for example, a red, green, blue (RGB) array of light emitting diodes (LEDs). Some embodiments may also include infrared emitting light sources for projecting infrared light into the wearer's eyes for any of the reasons discussed herein. Alternatively, the array of light sources 714 can be implemented as a liquid crystal display (LCD) panel or some other type of display panel. Each light source can be used to emit light corresponding to a pixel or sub-pixel of the processed integral image. The light emitted from each light source 714 is then projected by one of the lenslets 712 to a corresponding point 716 in space before the user's eye. In some embodiments, each lenslet 712 projects one processed elemental image. The overlap of light from each of the projected elemental images re-creates a physical light field which can be viewed by a user.

In FIG. 14, the integral imaging display 62 additionally includes a two-dimensional array of photodetectors 715 (illustrated as shaded boxes interspersed with the light sources 714). The photodetectors 715 can be sensitive to visible and/or infrared light. The photodetectors 715 can be used to collect light from the wearer's eye and digitize the collected light. In some embodiments, the photodetectors 715 image the eye of the wearer, including any anatomical portion thereof. In some embodiments, the photodetectors 715 are interspersed with and among the light sources 714. The photodetectors 715 and the light sources 714 may receive light from the same set of lenslets 712. Alternatively, the photodetectors 715 and the light sources 714 may be physically spaced apart (e.g., in separate clusters) sufficiently such that the photodetectors 715 use one or more different lenses than the light sources 714. One or more groups of photodetectors 715 with their associated lens(es) can form one or more cameras for capturing light from the wearer's eyes. In some embodiments, the one or more cameras are light field cameras for capturing light field image data from the wearer's eyes. The photodetectors 715 shown in FIG. 14 can be used to collect light from the wearer's eyes for any of the purposes discussed herein. For example in the autorefractor and aberrometer embodiments discussed herein, the photodetectors 715 can be used to capture and digitize light reflected from the wearer's retina(s). These signals can then be processed by the light field processor 70 to determine information about the wearer's vision (e.g., his or her optical prescription and/or higher order aberrations). In some embodiments, the photodetectors 715 capture light field data. In other embodiments, the photodetectors 715 capture conventional 2D images.

Although FIG. 14 illustrates an embodiment where the photo detectors 715 are integrated with the integral imaging display 62, this is not required. In other embodiments, the photodetectors 715 can be provided to the side of the integral imaging display 62 or anywhere else where they may be configured to obtain an adequate view of the wearer's eyes (e.g., using beam splitters, mirrors, prisms, etc.).

The following paragraphs describe various example embodiments of the devices, systems, and methods described herein.

A wearable ophthalmic device, comprising: a left outward facing head-mounted light field camera configured to receive light from a user's surroundings and to generate numerical light field image data for the user's left eye; a right outward facing head-mounted light field camera configured to receive light from a user's surroundings and to generate numerical light field image data for the user's right eye; a light field processor configured to generate modified numerical light field image data by introducing a translational shift to the numerical light field image data captured by the light field camera for one of the user's eyes based on a convergence point of the user's gaze; and a head-mounted light field display configured to generate a physical light field corresponding to the modified numerical light field image data.

The device of any of the preceding paragraphs, wherein computationally introducing a translational shift comprises computationally introducing prismatic power.

The device of any of the preceding paragraphs, wherein the light field camera comprises an integral imaging camera.

The device of any of the preceding paragraphs, wherein the light field display comprises an integral imaging display.

A method of using a wearable ophthalmic device, the method comprising: receiving light from a user's surroundings and generating numerical light field image data for the user's left eye using a left outward facing head-mounted light field camera; receiving light from a user's surroundings and generating numerical light field image data for the user's right eye using a right outward facing head-mounted light field camera; generating modified numerical light field image data by introducing a translational shift to the numerical light field image data captured by the light field camera for one of the user's eyes based on a convergence point of the user's gaze using a light field processor; and generating a physical light field corresponding to the modified numerical light field image data using a head-mounted light field display.

The method of the preceding paragraph, wherein computationally introducing a translational shift comprises computationally introducing prismatic power.

The method of any of the preceding paragraphs, wherein the light field camera comprises an integral imaging camera.

The method of any of the preceding paragraphs, wherein the light field display comprises an integral imaging display.

Correction of Other Eye Abnormalities

The systems described herein (e.g., system 600 in FIGS. 6, 7, and 14) can also be used to detect, diagnose, assess, correct, and/or treat a variety of other eye abnormalities or distortions using any of the techniques described in U.S. patent application Ser. No. 15/072,290 entitled "METHODS AND SYSTEMS FOR DIAGNOSING AND TREATING HEALTH AILMENTS," filed Mar. 16, 2016, the entire contents of which are hereby incorporated by reference. For example, the systems described herein can be used to perform contrast testing, visual field testing, or color blindness testing as described in U.S. patent application Ser. No. 15/072,290 and as now briefly summarized.

In some embodiments, the systems described herein (e.g., system 600) may be configured to test a wearer's contrast sensitivity. Contrast sensitivity testing may be used to assess a wearer's ability to distinguish different luminances in an image. Contrast sensitivity testing may indicate the presence of conditions such as age-related macular degeneration, amblyopia, and/or cataracts.

A system (e.g., system 600) may administer contrast sensitivity testing by projecting static or changing images using the integral imaging display 62. The system can then detect a response from the wearer. The image may be a high-contrast image whose contrast gradually decreases or a low-contrast image whose contrast gradually increases. For example, a dark grey image presented against a white background may be gradually lightened until the image becomes white or nearly white. The wearer may be directed to indicate when the image can no longer be discerned due to the similarity to the background color. The test may be repeated multiple times with the same or different images to gain a more accurate estimate of the wearer's contrast sensitivity. For example, an image may change to a different number/letter/shape each time it is lightened, and the wearer may be asked to report the number/letter/shape of the image after each change. Color variation between images and/or glare testing may be incorporated as well.

In some embodiments, the system may evaluate the wearer's contrast sensitivity using a static image. For example, the system may use an image such as a Pelli-Robson contrast sensitivity chart. The Pelli-Robson chart contains multiple rows of capital letters against a white background. The top left letter is printed in black, with each successive row and/or letter being printed in a lighter shade of grey, the bottom row and right letter being printed in a shade close to white. The system may project a Pelli-Robson chart or similar sequence of letters, numbers, shapes, or other patterns of increasing or decreasing contrast. The wearer may be asked to read the sequence of letter or numbers or describe shapes or patterns, providing a response via any of the response methods described herein. The system may then determine a contrast sensitivity of the wearer based on the lowest contrast for which the wearer is able to accurately detect the presence of a letter, number, shape, or other pattern.

In some embodiments using changing images, the wearer may be prompted automatically or by another user, such as a medical professional, to indicate when the image appears or disappears, and/or to indicate if the wearer can distinguish between images of different luminance. In other embodiments using static images, the user may be prompted to indicate the observed content of the image, such as visible letters, numbers, shapes, or other patterns. The user may then input the wearer's response through a user interface.

Contrast sensitivity testing may be performed in discrete tests on demand, or may be performed periodically and/or repeatedly over time. Repeated analysis may allow for the tracking of progressively decreasing or increasing contrast sensitivity through historical analysis of previous results, as well as for monitoring or detecting abnormalities. Thus, contrast sensitivity testing functions may be incorporated into a device worn only for ophthalmic diagnosis, or may be a part of a device worn regularly, such as for entertainment, work, or other purpose(s), so that examinations may be performed automatically at regular intervals and/or at various times of day, week, month, year, etc. In some embodiments, the frequency of regularly scheduled tests may be automatically adjusted based on trending of the contrast sensitivity testing results. If the system detects that the wearer is experiencing decreased contrast sensitivity, the system may initiate further testing and/or contact a clinician. For example, the system may contact a clinician if it detects that the wearer is having difficulty seeing in dark conditions or exhibiting accommodation/vergence fluctuations associated with struggling to focus. In augmented or virtual reality systems, the system may use the outward facing integral imaging camera 16 to provide alerts to a wearer. Alerts may be based on detection of hazardous conditions not visible to a wearer due to a deficiency in contrast sensitivity. The system may determine the presence of an invisible hazard based on a correlation of the images from the integral imaging camera 16 with known contrast sensitivity data of the wearer, such as light conditions in which the wearer has reduced contrast sensitivity. When a hazard is detected that the wearer is unlikely to be able to see, such as an incoming dark object or a hole in the ground during darkened nighttime conditions, the system may alert the wearer. Alerts may include visual, audio, or tactile notifications.

In some embodiments, the systems described herein may be configured to detect, diagnose, and/or compensate for visual field deficiencies. Visual field testing may be used to detect visual deficiencies in the central and/or peripheral vision by analyzing a subject's ability to see stationary and/or moving objects and/or images at various locations of the subject's visual field. Visual field testing may indicate the presence of various conditions, such as scotoma, trauma to the cornea, vitreous tears, traumatically induced cataracts, retinal hemorrhage, retinal detachment, macular degeneration, or intrabulbar hemorrhage (Torsion's syndrome).

A system (e.g., the system 600) may administer visual field testing by determining the ability of a subject to detect an image at various locations within the visual field. The system may project light into the eye of a wearer using, for example, the integral imaging display 62 to form an image in the eye. The system can then detect a response from the wearer. The image may be, for example, a small dot that can be clearly seen if projected in a healthy portion of the visual field but likely would not be seen if projected in a deficient portion. In some embodiments, the wearer may be prompted automatically or by another user, such as a medical professional, to indicate if the wearer saw an image and/or the time at which the wearer observed the image. The user may then input the wearer's response through, for example, any of the user interfaces discussed herein. In some embodiments, the system may require verification by the user of a characteristic of the image (e.g., a number, color, letter, shape, etc.) to ensure that the wearer saw the image.

In some embodiments, the system may be used to evaluate the wearer's visual field perception at the periphery of the field of view. For example, the system may provide a stationary fixation target near the optical axis. While the wearer's gaze is fixed at the fixation target, an image may be projected at an outer portion of the display, outside the wearer's visual field. The image may then be moved inward, toward the fixation target, until it enters the field of view. The wearer may be directed to indicate when the target becomes visible, such as by any of the response methods described herein. In some embodiments, the wearer may be directed to describe a characteristic of the image, such as a shape, number of apparent objects, or other feature. The test may be repeated in various quadrants or locations of the periphery of the wearer's visual field, such as at the left, right, top, and/or bottom of the visual field.

Visual field testing may be performed in discrete tests on demand, or may be performed periodically and/or repeatedly over time. Repeated analysis may allow for the tracking of progression of visual field deficiencies through a historical analysis of previous results. Thus, visual field testing functions may be incorporated into a device worn only for ophthalmic diagnosis, or may be a part of a device worn regularly, such as for entertainment, work, or other purposes, so that examinations may be performed automatically at regular intervals and/or at various times of day, week, month, year, etc. In some embodiments, the frequency of regularly scheduled tests may be automatically adjusted based on trending of the visual field testing results.

In augmented or virtual reality systems, the system may use the outward facing integral imaging camera 16 for providing alerts to a wearer. Alerts may be based on detection of hazardous conditions not visible to a wearer due to a visual field deficiency. The system may determine the presence of an invisible hazard based on a correlation of the images from the integral imaging camera 16 with known visual field data of the wearer, such as quadrants in which a wearer has reduced peripheral vision. When a hazard in a deficient quadrant is detected, such as an incoming object, a hole in the ground, or other condition, the system may alert the wearer. Alerts may include visual, audio, or tactile notifications.

The systems described herein may also administer a color test to test a wearer's deficiencies in detecting specific colors. For example, a system (e.g., system 600) may administer the Ishihara color test, which is designed to test for red-green color perception deficiencies. The test includes showing a series of colored plates ("Ishihara plates"). The color plate contains a circle of dots which appear to be randomized in size and randomized or uniform in color. Within each circle are patterns of dots which form a number or shape. In some circles the number or shape is clearly visible only for viewers with normal color vision but difficult or impossible to see for viewers who have a red-green perception deficiency. In other circles the number or shape is only visible for viewers with a red-green defect. In some embodiments, color plates may be selected and/or modified based on known conditions and/or previous responses of the wearer. Colors or other stimuli may be changed incrementally to determine the bounds of a wearer's color perception deficiency. That is, hues may change from a first color to a second color through a plurality of hues. For example, a wearer with a detected red-green deficiency may be presented with plates gradually changing the red color to orange or purple, and the wearer's response to each incremental change may be recorded.

In one or more embodiments, the system may be programmed in a manner similar to the above process flows to administer the Ishihara color test by providing virtual images of each of the color plates, and receiving user input regarding the color plate. Images of the color plates may be provided by the integral imaging display 62.

The system may automatically determine whether the user has a red-green vision defect or other defects based on the input received from the wearer in response to the color test. The user input regarding the color plate may be produced and/or received by any suitable method for a user to input a description of a number, letter, shape, or other image characteristic. For example, the input may be received through a user interface such as a keyboard, number pad, or touch screen having keys or virtual buttons corresponding to the numbers utilized in the Ishihara plates. In some embodiments, the system may be configured to receive a spoken input from the wearer, and to determine the wearer's response to the test using voice recognition. A user interface may further have an option for the wearer to indicate that no number or shape was observed.

In some embodiments, the system may be configured to determine if the wearer saw the number or shape in the projected Ishihara plate without conscious input from the wearer. For example, the system may detect a fixation of the gaze of the wearer (e.g., using an inward facing camera) on the location of the number or shape in the Ishihara plate for a sufficiently long period of time to be an indication that the number or shape was seen, while an extended period of scanning of the image by the wearer may indicate an inability to see the number or shape. For example, the system may track the wearer's gaze for a period of up to one second, five seconds, ten seconds, or longer.

In various embodiments, the system may use patterns and/or images other than Ishihara plates that test a wearer's ability to detect different colors. For example, the system may be configured to function as an RGB anomaloscope. A test based on color matching of two images and/or light sources is used to provide color detection testing. One source or image can have a fixed control color, while the other source or image is adjustable by the viewer (e.g., a fixed-spectral image that can be adjusted in brightness). The viewer may be presented with a variety of control colors, and attempts to match the adjustable image to the control image, or determine that a match cannot be made.

In various embodiments, the system may be configured to administer color testing repeatedly and/or periodically. For example, the system may test a wearer's color perception periodically, such as several times per day or one or more times per week, month, or year, and compare the results over time. In some embodiments, the frequency of regularly scheduled tests may be automatically adjusted based on trending color blindness testing results and/or based on a detection that the wearer is having difficulty distinguishing colors. In such cases, the system may be able to better detect the severity or time-variation of a wearer's color detection deficiency by testing the wearer's color vision at various times of day and in various light conditions. Similarly the system may be able to obtain more complete and/or accurate results by testing a wearer's color vision repeatedly at different depth planes, degrees of accommodation, and/or areas of the retina. Accordingly, the system may be able to vary the depth plane, accommodation, and/or area of the retina when administering a color vision test. Repeated testing over longer time periods, such as months or years, may allow for the tracking of any improvement or degeneration of a wearer's color detection deficiency, such as due to macular degeneration or any other progressive conditions.

The system may also be configured for therapeutic functions such as compensating for color detection deficiencies of the wearer. Therapeutic functions may include computationally modifying color, intensity, and/or other qualities of images and/or light from the world. For example, the systems may function as a color enhancer by computationally increasing the intensity of light in a portion of an image containing a color of reduced detection. In some embodiments, the system may computationally shift the color of such a region, such as by computationally changing the wavelength of the light or adding light of a different wavelength, so as to present light of a color that the wearer is better able to detect.

In embodiments comprising an augmented reality device, the system may similarly modify the wearer's view of light from the surrounding world. The augmented reality system may detect the colors of light entering the device in real time or near real time, and may computationally modify portions of the light or project additional light to correct for the wearer's color detection deficiency. For example, the system may use the outward-facing integral imaging camera 16 to image the world around the wearer. The system may use the integral imaging display 62 to project additional light of the same or different color to augment the intensity in areas of reduced detection ability so as to at least partially mitigate the color detection deficiency of the wearer. The system may further incorporate a labeling function, wherein the name of a known deficient color may be augmented over a region of the outside light determined to be of that color. In some embodiments, superposition may be used to enhance color in a portion of the display by projecting light of a desired amplitude, such as by adding a tint to the image.

Phoropter

Figure 15:
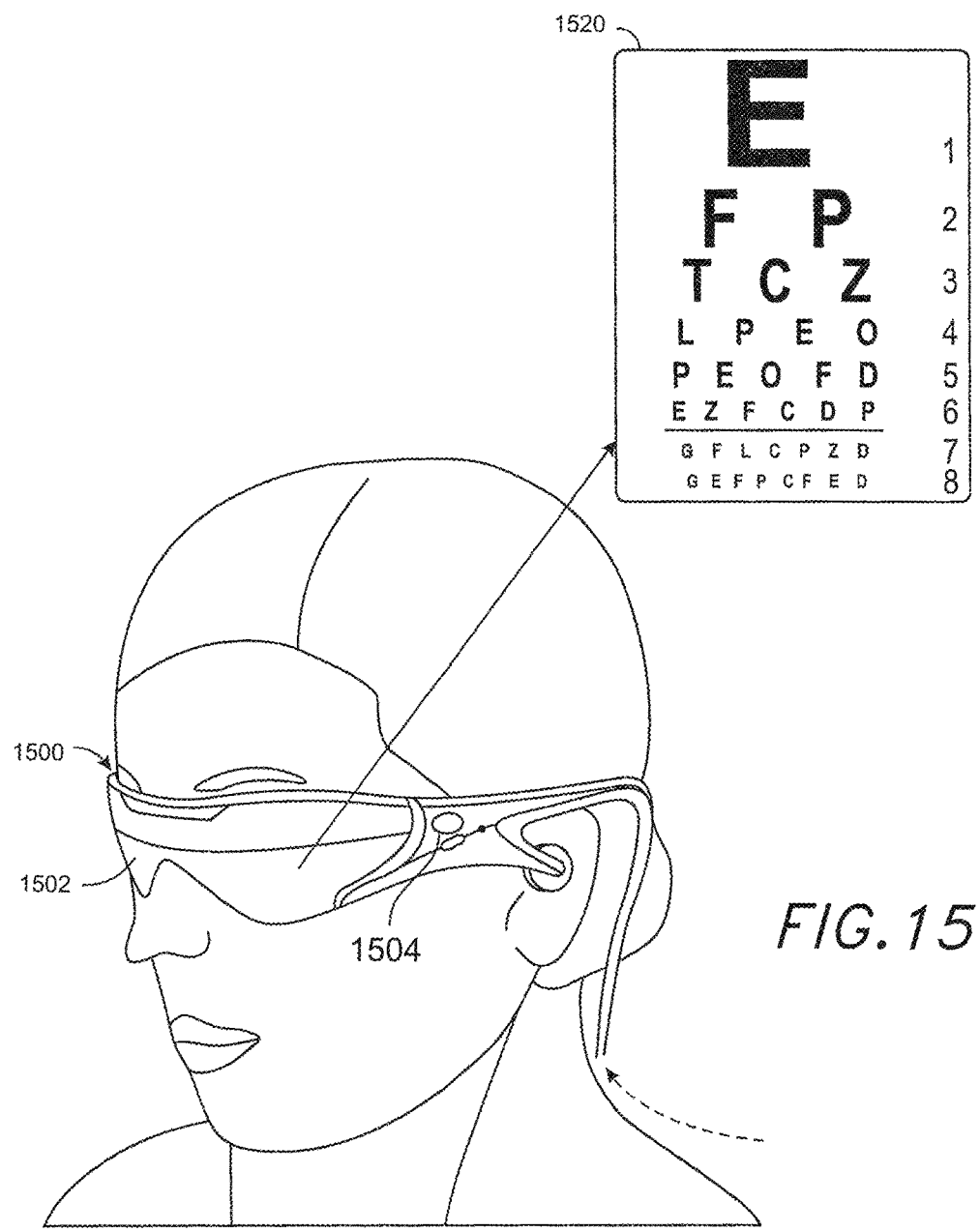
FIG. 15 illustrates how the wearable devices described herein can be used to function as a phoropter or refractor to determine a suitable refraction that corrects or improves the vision of a wearer or a patient.

FIG. 15 illustrates how the wearable devices described herein can be used to function as a phoropter or refractor to determine a suitable refraction that corrects or improves the vision of a wearer or a patient. For example, the light field processor systems described herein can be used to implement the phoropter shown in FIG. 15. The results of a test from the phoropter can be used, for example, to determine a wearer's or patient's optical prescription (e.g., for corrective lenses in glasses or contact lenses or for use in a light field processor system). It should be appreciated that such a system may be used to administer an eye exam, and this exam may typically be administered at a doctor's or clinician's office. In one or more embodiments, the patient's individual light field processor system may be used, possibly with doctor supervision, or the doctor's office may have its own version of the light field processor system that may be used for diagnostic purposes. Although FIG. 15 is discussed in connection with augmented reality, similar features can be included in a virtual reality device such as virtual reality eyewear as well.

A conventional phoropter is used by eye care professionals for eye examination and to determine a patient's refractive error and therefore corrective refractions to compensate for any ocular anomalies. Using this information, the eye care professional can determine an optical prescription of the patient's eyes to improve or correct the patient's vision. The conventional phoropter typically comprises different lenses that may be tested, and usually involves presenting an eye test chart of alphabets of varying sizes to test the patient's vision. The patient looks at the eye test chart and lenses of different refractive powers are placed in front of the patient's eyes to determine whether the patient's vision has improved. The conventional set up tends to be bulky, and requires the doctor to individually select a next step size in the lens. The clinician typically asks the patient's feedback on image clarity, and changes the lenses accordingly.

In contrast, some embodiments of the wearable light field processor system 1500 may be used to perform these same functions without a bulky phoropter setup. The wearable light field processor system 1500 includes an augmented (or virtual) reality display platform 1502 configured to project an image to the eye of a wearer. In some embodiments, the augmented or virtual reality display platform 1502 can be any of the light field processor systems 600 described herein. The display platform 1502 can be configured similarly to the display lens 106, as described herein, for example, with reference to FIG. 5. In some implementations, such as for light field processor systems, the display platform 1502 can also be configured to pass light from the world or environment through the display platform 1502 (e.g., through a lens in the front thereof and/or via the integral imaging camera 16) to the eye of the wearer. In this way, the wearer can see images projected with the display platform 1502 superimposed with what the wearer can see in the world. In some embodiments, rather than a physical eye test chart, a virtual eye test chart 1520 may be projected to the wearer using the display platform 1502 (e.g., via the integral imaging display 62). To provide functionality similar to a phoropter, the focus of the image can be varied computationally (as discussed herein) by the light field processor 70. The wearable light field processor system 1500 can be configured to administer or provide an eye exam by automatically providing incremental changes in an optical prescription by varying the focus of the image. This can be done by computationally varying the refractive power applied to image data by the light field processor 70 in the display platform 1502.

As described herein, the light field processor system 1500 can include a light field processor 70 that is configured to computationally alter one or more optical properties of image data provided to it. For example, the light field processor 70 can add or subtract optical power to or from the image data by, for example, altering the curvature of wavefronts in the light field image data or otherwise introducing positive or negative spherical/cylindrical optical power. The light field processor 70 can therefore provide a variable optical correction, such as sphere, cylinder and axis, or higher order aberration corrections.

In certain implementations, the display platform 1502 includes a display 62 which may also include the ability to not only project light into the wearer's eyes but also capture light therefrom (e.g., as discussed herein with respect to FIG. 14). The received light can be imaged or otherwise detected. This may be utilized in an eye exam where display 62 is configured to image the retina of the wearer to monitor images formed at the retina. To determine the accommodative state of the eye, a reflex from the retina (e.g., the reflex from an image projected into the eye of the wearer) can be measured using the display 62. This can result in a rapid measurement of the accommodative state of the eye. For example, a sequence of point source images (e.g., outside of the visible wavelength band in the infrared band) can be projected from various apparent depths by the display 62 into the eye of the wearer and the display 62 can simultaneously measure the reflex from the retina. The light field processor system 1500 can be configured to determine in real time the accommodative state of the eye by determining which depth plane corresponds to the brightest, smallest, or best focused image based on the reflex that is the most collimated. (The light field processor 70 can be used to provide image data from different apparent depths planes.) The light field processor system 1500 can be configured to project a beam of light from an optical source (e.g., the display 62) into the eyes of the wearer. A portion of the projected beam can be reflected, scattered, and/or diffracted by various anatomical features of the eye of the wearer and received by one or more imaging devices. An electronic hardware processor (e.g., the light field processor 70) can be used to analyze light received from the eye of the wearer to examine the various structures of the wearer's eye. This can result in a determination or approximation of the accommodative state of the eye, which may include the shape of the lens, the pupil constriction state, the vergence, dynamic accommodation, etc. In some embodiments, computational refractive correction can be provided by the augmented or virtual reality device 1500 using the light field processor 70.

In some implementations, to conduct an eye exam, the user/wearer may be presented with a variety of images of varying sizes, shapes, colors, brightness, contrast, etc., and the user/wearer may provide input as to the clarity of the image through a user interface 1504 of the light field processor system. In some embodiments, the light field processor system is configured to automatically determine the clarity of the image based at least in part on detecting whether the image is focused on the retina of the wearer. This can be done by imaging the retina of the user and measuring, analyzing, and/or observing the reflex from the retina of the projected image. Rather than physically changing lenses, as in a conventional phoropter, if the user/wearer indicates that a particular image is not clear, or that the image is not comfortably seen, the focus of the image may be automatically computationally varied to provide incremental changes in the corresponding or equivalent optical prescription. Thus, eye exams may be conducted seamlessly through the light field processor system locally or remotely. For example, a clinician or doctor can administer the eye exam remotely, such as, by way of example and without limitation, over a phone, using video conferencing, over a networked communication program, or the like. It should also be appreciated that, in some implementations, the eye exams may be conducted with or without direct interaction from a clinician or with less or minimal effort and time of the clinician.

In some embodiments, adjustments to the optical prescription may be automatically performed by the light field processor system based on physical changes of the eye while attempting accommodation and/or vergence. For example, the light field processor system may be programmed to detect certain patterns of eye behavior that are symptomatic of weakening eyes. Based at least in part on the tracked eye behavior, eye adjustments may be automatically made by the light field processor system. The system may for example, upon detecting that the wearer struggles to accommodate, initiate a phoropter examination such as described herein or the system may alert the wearer or clinician that the wearer is struggling to accommodate. In some embodiments, the system detects that the wearer struggles to accommodate by detecting microfluctuations in accommodation (e.g., small and/or rapid changes in lens shape, vergence, pupil size, etc.). In certain implementations, accommodative struggles can be detected by monitoring the focus state of an image projected onto the retina of the wearer, as described herein. If the reflex from the retina is fluctuating, the system can be configured to determine that the wearer is struggling to accommodate. The system might present the wearer with images, and test different optical corrections asking the users to provide feedback as to whether the optical correction improves the images. In some implementations, rather than asking for the wearers to provide feedback, or in addition to asking for feedback, the system can be configured to determine if the image is in focus by observing, measuring, and/or analyzing the image on the retina of the wearer. As discussed above, computational optical correction may be used to implement the different test corrections during the examination. In some embodiments, the system can be used to determine a phoria of the wearer by presenting images to eyes of the wearer one eye at a time. In certain implementations, the system can be used to monitor vergence of the wearer on a target. If the wearer is exophoric when attempting to focus on a close image (e.g., an image projected from a near depth plane), the system can be configured to determine that the wearer may be presbyotic or fatigued and/or whether the wearer may have strabismus or amblyopia. The system can also be configured to administer a variety of tests of visual field by providing images from a variety of different depth planes.

The image provided by the light field processor system can be a stored image. The wearable light field processor system 1500 can include a data store that includes one or more stored images suitable for conducting an eye exam or for determining an optical prescription for a wearer. The stored image may be letters, numbers, symbols etc., such as used in eye charts. The image may be presented to the viewer at the desired depth plane, such as at infinity or an otherwise large apparent distance, e.g., at least 20, 40, 60, 80, or 100 feet away. As described herein, the stored image can be processed to produce corrected wavefronts for projecting to the wearer. The corrected wavefronts can be configured to account for an optical prescription or anomaly of the wearer's eye. In some embodiments, the light field processor 70 in the display platform is used to computationally provide adjustments to the image that the wearer sees to account for the optical prescription. The light field processor 70 may also, for example, alter the intensity pattern comprising the image, for example, to compensate for distortion or fisheye wherein straight lines appear curved. For example, to compensate for pincushion distortion, some barrel distortion may be introduced into the intensity pattern that comprises the images. Similarly, to compensate for barrel distortion, some pin cushion distortion may be introduced into the intensity pattern that comprises the images. Other types of modifications to the intensity pattern that makes up the image may be introduced by software that is used to drive a spatial light modulator or light source to produce the desired intensity pattern. In some embodiments, the wearable augmented or virtual reality device 1500 can be configured to use the display platform 1502 to project images of varying size to the wearer or images from varying depth planes to the wearer. In some implementations, the image can include letters or shapes of varying sizes and/or projected from varying depth planes. In various implementations, the size and/or depth planes of the letters and/or shapes projected to the wearer can be varied during the eye exam. In some embodiments, the system can be configured to administer a brightness or glare test that include objective measurements of functional visual acuity in different brightness and glare conditions. In various embodiments, the system can be configured to administer a brightness acuity test to determine the functional visual acuity in various bright light conditions. For example, the system can be configured to simulate three or more bright-light conditions: 1) high-direct overhead sunlight; 2) medium-partly cloudy day; and 3) low-bright overhead commercial lighting. The visual acuity measurements can be similar to those that would be measured in these three conditions using a standard eye chart (e.g. the eye chart 1520). The result of such a test may be an assessment of functional visual acuity. Such tests can be used to test for sensitivity to bright light, photophobia, impaired scotopic vision, and the like. In some embodiments, the system can be configured to test individual colors. For example, the light field processor system can be configured to determine refractive errors for individual colors (e.g., red, green, blue, yellow, etc.). In some embodiments, the system can be configured to test a variety of depth planes. For example, the light field processor system can be configured to determine refractive errors for individual depth planes. This can result in an optical prescription that changes based at least in part on depth plane. Refractive correction for presbyopia may also be determined.

In some embodiments, the wearable augmented (or virtual reality) device 1500 can include one or more outward facing cameras. In certain implementations, the one or more outward facing cameras can be similar to the cameras 16 described herein with reference to FIG. 5 or the integral imaging cameras 16 described herein with reference to FIGS. 6-7. The outward facing cameras in an augmented reality display device can be configured to capture images the surrounding environment to determine, for example, where to superimpose a test image such as letters or symbols. For example, the light field processor system might superimpose an image of an eye chart, such as a standard Snellen chart or other visual acuity chart over an area in the field of view of the wearer corresponding to the wall of the optometrist's office. In another example, the outward facing cameras can be configured to capture images of an eye chart, such as a standard Snellen chart or other visual acuity chart that is actually on the wall of the optometrist's office. The wearable augmented or virtual reality device 1500 can then be configured to modify the captured image based at least in part on the desired depth plane for presenting the image. For example, the acquired image can be projected by the display platform 1502 at infinite accommodation. Then, through a user interface 1504, the light from the image can be computationally manipulated by the light field processor 70 to provide functionality similar to physically changing a lens with a conventional phoropter. For example, sphere, cylinder, or higher order aberration correction can be introduced. If cylinder is to be added, the appropriate axis can also be determined. In this way, an eye exam can be conducted to determine an optical prescription of the wearer. In some embodiments, the system is configured to objectively measure or estimate an optical prescription through observation, measurement, and/or analysis of the manipulated image, determining whether it is in focus on the retina of the wearer, as described elsewhere herein.

The wearable light field processor system 1500 can include one or more user interface features 1504 configured to allow a wearer or other person to provide input to the device. The user interface features 1504 can be integrated with the device 1500, as illustrated in FIG. 15. In some implementations, the user interface features 1504 are provided by a device or component that is not physically integrated with the device 1500. For example, the user interface features 1504 can be provided by a device or system that is in communication with the device 1500. This can be a smartphone, computer, tablet, or other computational device that is in wired or wireless communication with the device 1500. In some embodiments, the user interface features 1504 can be provided by a combination of different devices and systems linked to the device, e.g., through wired or wireless communication networks or through components that are physically linked to the device or integrated with the device. A touch screen, voice recognition system, or virtual touch screen are some examples of interfaces. Accordingly, the user interface features 1504 can include capacitive features sensitive to touch, keyboards, buttons, microphones, photodetectors, cameras, and/or a variety of software-implemented features provided by a graphical user interface. The user interface features 1504 can be presented on a device with a touch screen wherein interaction with the touch screen provides input to the wearable augmented or virtual reality device 1500. In various embodiments, a virtual touch screen is provided through the images projected to the user's eyes and sensors to sense the users moving body, e.g., finger. In some embodiments, the user interface features 1504 include gesture detection components to allow a wearer to provide user input through gestures. In some embodiments, the user interface features 1504 include gaze detection components to allow a wearer to provide user input through gaze of the eyes (e.g., this can include selecting a button or other element when the wearer fixates on the button for a time or when the wearer blinks when fixated on the button). Such user interface systems can be employed for other devices and systems described herein.

In the light field processor system, the user interface features 1504 can be used by the wearer to provide feedback regarding the quality of the image as perceived by the wearer. The wearer can provide feedback through the user interface features 1504 regarding whether the wearer can comfortably view the image being projected to the user for example as changes to the applied refractive power (e.g., incremental values of sphere, cylinder, and axis and/or higher order aberration correction) are provided incrementally. In this manner, an appropriate optical prescription for the wearer can be determined.

In some implementations, the clinician or doctor can also use the interface features 1504 to vary the focus and/or the depth plane from which the image is being projected to the wearer or the size of the image being projected. Such changes can be used to incrementally if desired.

Figure 16:
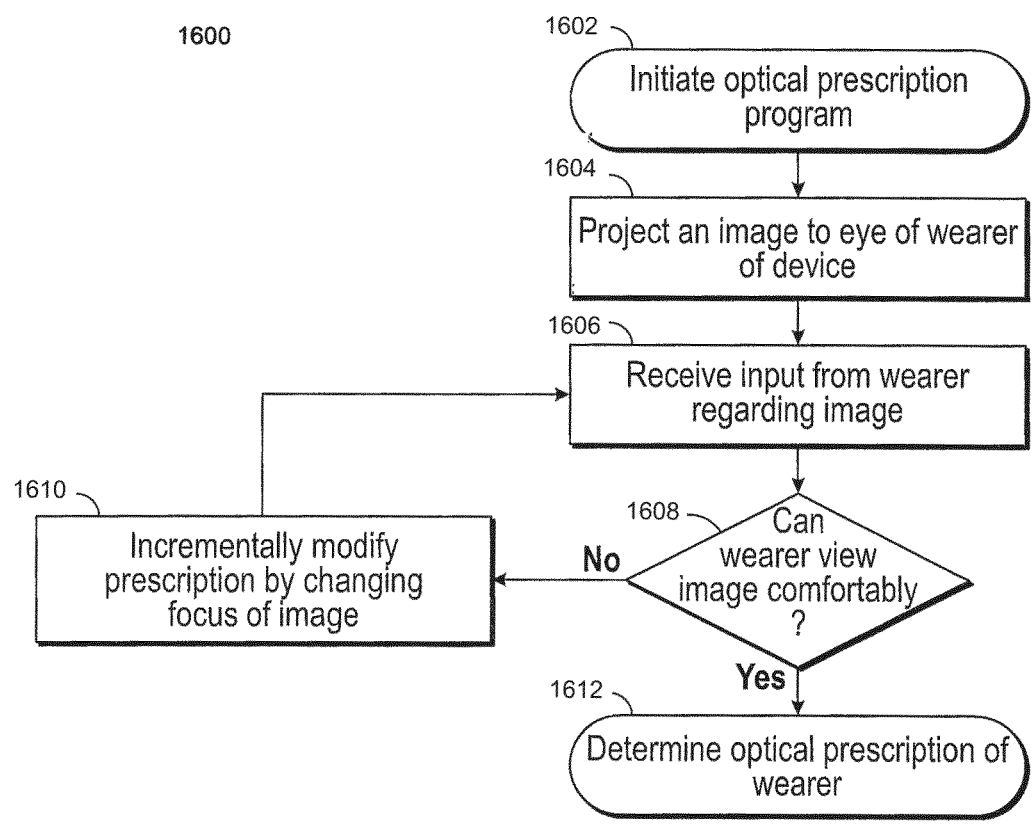
FIG. 16 illustrates an example method for determining an optical prescription of a wearer of a light field processor system configured for use as a virtual phoropter.

FIG. 16 illustrates an example method 1600 for determining an optical prescription of a wearer of a light field processor system configured for use as a virtual phoropter. For ease of description, the method 1600 will be described as being performed by a light field processor system, such as the augmented (or virtual) device 1500 described herein with reference to FIG. 15. However, it is to be understood that components or subparts of the various augmented reality (or virtual) devices disclosed herein, or other similar devices, may be used to perform any step, combination of steps, or portions of a step in the method 1600.

At block 1602, the ophthalmic device initiates an eye test program. The eye test program can be a stored process or sequence of functions provided by the ophthalmic device. Initiating the eye test program can include determining or retrieving a starting optical prescription, such as for a wearer that has previously undergone an eye test or other eye exam. In some implementations, the eye test program can integrate information about ocular anomalies of the wearer's eye(s), where the information about the ocular anomalies can be entered by the wearer or clinician, determined from a previous eye test program, or retrieved from a data store (e.g., a data store that is part of the light field processor system or a networked data store). Initiating the eye test program can include determining the image or sequences of potential images to be projected to the wearer. Initiating the eye test program can include determining whether a clinician or doctor is administering the eye exam or whether the examination is being self-administered by the wearer. In some embodiments, the ophthalmic device initiates the eye test program in response to input received from the wearer or a clinician.

At block 1604, the light field processor system projects an image to the wearer's eyes. For example, the light field processor system can project an alphabet, letters, and/or shapes of a targeted size to the wearer. The image can be a stored image or the image can be acquired by the light field processor system. The image can include elements configured to aid in determining visual acuity of the wearer, wherein the visual acuity elements comprise, for example and without limitation, icons, symbols, letters, shapes, or the like. The visual acuity elements of the image can have a variety of sizes within the image and/or the size of the visual acuity elements can be varied by the light field processor system.

At block 1606, the light field processor system receives user input regarding the image. The user input may indicate whether the wearer is able to view the image clearly or not. In one or more embodiments, the light field processor system may begin by projecting relatively small letters that increase in size until the received user input indicates that the wearer can see the projected image clearly. In some embodiments, the light field processor system is configured to present an eye chart, such as a conventional eye chart like the Snellen chart. In such embodiments, the received user input can include which portion or portions of the projected chart the wearer can see clearly.

At block 1608, the light field processor system determines whether the user can comfortably view the image (e.g., a projected eye chart). In some embodiments, the system is configured to receive user input through a user interface as to whether the user can comfortably view the image. As described above, examples of such a user interface may include a voice recognition system, a touch screen, or a virtual touch system.

In some embodiments, the user input received in block 1606 is automatically determined through analysis of physical and/or optical characteristics of the wearer. For example, the user input that is automatically determined includes analysis of whether the image is in focus by observing, measuring, and/or analyzing the retina of the wearer. As described herein, by measuring the reflex from the retina, the light field processor system can be configured to assess the quality or degree of focus of the image formed by the wearer's eye. In some embodiments, the light field processor system can be configured to project a pair of spots into the eye of the wearer. The reflex of these projected spots can be measured and analyzed to determine the quality of focus of the image. For example, where the images of the projected spots on the retina are aligned, the light field processor system may determine that the wearer is focusing on the projected image or that the wearer is accommodating properly at the targeted location.

In some embodiments, the light field processor system is configured to determine that the wearer can comfortably view the image based at least in part on detection of relaxed accommodation and/or vergence. As described herein, the light field processor system can include eye detection and/or tracking components configured monitor the eye. Such components may be able to detect accommodation, vergence, and/or pupil size of the wearer. Lens accommodation may be detected, for example, an autorefractor (as described in greater detail elsewhere herein) that measures a size of an image on the retina. Vergence and pupil size can be measured with one or more inward facing cameras. In some embodiments, the light field processor system monitors the fluctuations of the eye when the user is trying to focus on a targeted object or image. For example, when an eye focuses on a stationary stimulus, the power of the lens of the eye changes rapidly and continuously. When a person struggles to focus on a stationary object, these fluctuations can increase. This increase in fluctuation can be measured and/or observed by the light field processor system to determine that the wearer is not focusing on the targeted image or object. In some embodiments, the light field processor system can be configured to monitor these fluctuations and move the projected image (e.g., change the apparent depth plane from which it is being projected) until the wearer successfully focuses on the object. For example, the light field processor system can project the image from an apparent depth plane that is relatively near the wearer and push the image back (e.g., increase the distance between the wearer and the depth plane) until the light field processor system determines that the wearer is accurately focusing on the image.

Monitoring of the accommodation reflex of the eye can be employed by the light field processor system to determine if the wearer is not comfortable with the current prescription or if the wearer needs optical correction. An autorefractor can be used to determine whether the wearer is accommodating by monitoring the size of an image projected through the lens onto the retina, examples of which are described elsewhere herein. Such methods of monitoring accommodation can be used to determine whether the wearer is accommodating, which can be useful in assessing whether the wearer needs optical correction.

Vergence can be employed to assist in determining if an optical correction is needed as well, where vergence is monitored to test accommodation reflex. Using inward facing cameras and processing electronics, the light field processor system can be configured to track changes in the respective lines of sight of the left and right eyes and to determine the vergence. Such vergence information can be used to determine whether the wearer's eye is responding as expected to images presented at various depth planes. For example, if both eyes are substantially parallel and not converging when an image at a relatively close depth plane is being presented, the light field processor system can be configured to interpret this result as indicating that the wearer is not seeing the image comfortably or that the wearer has a vision defect. The vergence for different depth planes can be determined and whether the eyes match the proper vergence for a particular depth plane can be assessed. Likewise, potentially if vergence is observed to be inward for a depth plane that is at infinity, the wearer may need optical correction.

As another example, the light field processor system can test accommodation reflex by determining the size of the wearer's pupil or a change in the size of the wearer's pupil when an image is projected to the wearer. The light field processor system can be configured to track changes in the pupil size using an inwardly facing camera that images the eye and in particular the iris. This information can be used to determine whether the wearer's eye is responding as expected to images presented at various depth planes. For example, the size of the pupil is expected to constrict when looking at a closer object (compared to an object that is farther away). Thus, the light field processor system can be configured to present an image from a close depth plane and to track the response of the wearer's pupil. If the pupil does not constrict, or constrict sufficiently, the light field processor system can be configured to interpret this result as indicating that the wearer is not seeing the image comfortably.

Accordingly, to determine the comfort of the wearer in viewing an image, the light field processor system can determine the accommodation, vergence, and/or pupil size of a wearer as part of an examination of the accommodation reflex, when a particular image is projected to the user. Similarly, the comfort of the wearer can be determined when the image is projected through a variety of depth planes. In some embodiments, the light field processor system can compare the measured accommodation, vergence, and/or pupil size to an expected accommodation, vergence, and/or pupil size. If one or more of the measured characteristics are within a targeted range of the one or more expected characteristics, then the light field processor system can determine that the wearer is comfortably or correctly seeing the image (e.g., the wearer is seeing the image with expected, adequate, or normal visual acuity). If one or more of the measured characteristics are outside of the targeted range of the one or more expected characteristics, then the light field processor system can determine that the wearer is not comfortably or correctly seeing the image (e.g., the wearer is seeing the image with impaired visual acuity). In some embodiments, the light field processor system combines information regarding the measured characteristics with the information received or determined from the user input in block 1606 to determine whether the wearer comfortably sees the projected image. For example, when viewing an image from a relatively close apparent depth plane, the wearer's eyes are expected to converge or move towards one another, the pupils are expected to constrict, and the convexity of the lens is expected to increase. Deviation from one or more of these expectations can be interpreted as indicating that the user is not seeing the projected image comfortably or correctly (e.g., the wearer is seeing the image with impaired visual acuity).

If the light field processor system determines that the wearer is unable to comfortably view the image, for example, either by receiving input from the user through the user interface or by assessing the user's accommodation and/or vergence, the light field processor system proceeds to block 1610 to change the focus to incrementally increase the prescription (e.g., add or subtract more positive or negative sphere to get more a more positive or negative spherical wavefront). The system can also test for astigmatism and thus incrementally change the axis and cylinder. The light field processor system then returns to block 1606 to receive or determine user input to again determine whether the user can comfortably or uncomfortably view the image (e.g., with normal visual acuity). This loop can be repeated until the user comfortably sees the image.

In some embodiments, the light field processor system is configured to adjust the optical correction at block 1610 based at least in part on feedback received at block 1606 from the user input and/or objective assessment determined at block 1608 or as described elsewhere herein. In some embodiments, the light field processor system is configured to adjust the optical correction at block 1610 based at least in part on measurements of the accommodation, vergence, accommodation reflex, and/or pupil size of the wearer when viewing the projected image. Thus, in certain implementations, the light field processor system can be configured to conduct the eye examination using subjective and objective tests to determine an optical prescription for the wearer.

In some embodiments, a subjective element of the eye examination can include projecting an image and then projecting the image with a diopter change (e.g., ±0.01 D, ±0.1 D, ±0.125 D, ±0.25 D, ±0.5 D, ±1.0 D, or a substantially continuous change in diopter power, such as through a computational light field processor 70, and receiving user input regarding whether the image quality changed. In certain implementations, the light field processor system can also be configured to determine changes in the wearer's eyes (e.g., accommodation, vergence, pupil size, etc.) when the diopter value is changed. This objective test data can be combined with the subjective response of the wearer to determine if the change in diopter value results in a change in visual quality for the wearer.

If the light field processor system determines that the wearer is able to view the image comfortably, the light field processor system proceeds to block 1612 to determine the prescription of the wearer's eyes. It should be appreciated that, in some implementations, the same process may be repeated for both eyes (e.g., both eyes can be treated together applying the same correction to each eye or individually applying different correction to the left and right eyes). In some embodiments, this can be used to treat anisometropia where two different optical prescriptions are applied to the respective two eyes of the wearer. In some embodiments, the light field processor system can be configured to dynamically switch between optical prescriptions depending on what is being viewed by the wearer and/or what activities are being performed by the wearer. For example, lenses for anisometropia can be fatiguing for a wearer when primarily viewing images that are near or that are primarily far when compared to when a wearer is viewing images that are a mix of near, mid, and far ranges. Accordingly, the light field processor system can be configured to dynamically change the optical prescription applied in real time based at least in part on known optical prescriptions for treating a wearer's anisometropia, myopia, or hyperopia.

The method 1600 can be used to provide information to a light field processor system, such as the device 1500 described herein with reference to FIG. 15 or other similar devices described herein. Thus, the light field processor system can be configured to change the focus or other aspects of images being projected based on the optical prescription of the wearer as described herein. In some embodiments, the same wearable light field processor system that the wearer uses for entertainment, work, or other purposes can be used to perform the eye examinations described herein.

The method 1600 can be used to determine optical prescriptions, optical correction, or refractive correction for different depths. For example, there can be a first optical prescription for a far apparent depth plane, a second optical prescription for a mid-depth (intermediate) plane, and a third optical prescription for a near apparent depth plane or far and near, far and intermediate, near and intermediate.

The method 1600 and system can be used to correct or improve a wearer's vision where the wearer suffers from presbyopia. Different optical corrections can be applied to different depth planes and the associated content projected from those depth planes. Or the wearable light field processor system can be configured to switch between providing the prescriptions for far distance (if any) and near distance based on the sensed orientation of the user's head or eye. As described herein, orientation sensors or other sensors can be used to determine the orientation of the user's head or eye.

The method 1600 can be performed in real time to automatically determine an optical prescription of a wearer. This information can be stored in the light field processor system and used for future tests. For example, the light field processor system can be configured to update the wearer's current optical prescription for the wearer based on the examinations. For example, the light field processor system can be configured to monitor the eye and record the eye behavior of the wearer over time. Based at least in part on this information, the light field processor system can dynamically adjust the optical prescription of the wearer over time. For example, the light field processor system can measure the behavior of the eye when presenting an image at a known depth. The light field processor system can determine deviation from the expected eye response to the image to determine if the eye is behaving as expected. The light field processor system can be configured to initiate an examination and/or update the wearer's optical prescription or to initiate or schedule an updated eye examination if the light field processor system determines that the determined deviation is outside of a range (e.g., targeted, acceptable range of the expected behavior).

In some embodiments, the light field processor system can be configured to determine the optical prescription obtrusively. For example, this may occur where the light field processor system does not provide alternative functionality to the wearer while the eye examination is being conducted. In other words, this may occur where the wearer is requested to focus solely on the eye examination.

In some embodiments, the light field processor system can be configured to determine the optical prescription unobtrusively. For example, this may occur where the light field processor system is configured to acquire measurements of the wearer's eye behavior while the wearer is doing other things (e.g., watching movies, reading text, looking at images, etc.). The light field processor system can be configured to measure characteristics of the wearer's eyes while the wearer is performing these other activities, to compare measured characteristics of the wearer's eyes, to determine deviations from expected characteristics of the wearer's eyes. In some embodiments, the system can be configured to determine the optical prescription based at least in part on these determined deviations. In some embodiments the expected characteristics of the wearer's eyes can be based at least in part on the apparent depth planes and image properties being projected to the wearer. In some embodiments, when such deviations are detected, the system could ask the user to undergo an examination applied by the system or confirm a test optical correction as sufficient or insufficient. In some implementations, the light field processor system can be configured to track physical changes in the wearer's eyes while attempting accommodation and vergence while performing these other activities. In some embodiments, this information can be compared to measurements acquired while not attempting accommodation and vergence to determine the optical prescription.

In some embodiments, the light field processor system can be configured to objectively measure an optical prescription of a wearer. In various implementations, this may be accomplished without receiving feedback from the wearer regarding image quality. In certain implementations, this may be accomplished without projecting images of varying sizes to the user. For example, the light field processor system can be configured to project an image from a virtual infinite depth (e.g., the light field processor system puts the image at infinity). The light field processor system then measures the accommodation reflex, accommodation, vergence, and/or pupil size of the wearer. Based at least in part on the accommodation, vergence, and/or pupil size of the wearer and the deviation of the wearer's accommodation, vergence, and/or pupil size from what is expected, the light field processor system can objectively determine the wearer's optical prescription. For example, if the wearer's eyes are accommodating at +1 D when the image is being put at infinity, the light field processor system can objectively determine the optical prescription.

In some embodiments, the light field processor system can be calibrated to determine the proper diopter correction and/or account for the proper diopter correction based at least in part on the configuration of the display platform. For example, when adjusting the depth plane of an image being projected to a wearer, the light field processor system can be configured to be calibrated to correctly correlate the change in depth plane to a change in diopter or refractive power. In some embodiments, during calibration, the iris of the wearer is analyzed. The iris can be used to uniquely identify a patient and this unique identification can be used to access associated patient records to correlate the person and their medical records/prescriptions, etc.

In various embodiments, to reduce distraction, the view of the world in front of the wearer's eyes through the light field processor system is blocked or otherwise not visible during the examination. This can occur, for example, when images are presented to the viewer, although this approach is not necessary.

The light field processor system may be a system provided by the physician or clinician for testing at a medical facility or optometrist office or elsewhere. In other embodiments, the system may belong to the user and may be employed for other purposes such as entertainment (e.g., games and movies) and/or work activities. As described above, one benefit of implementing the examination on the user's system is that the examination can be conveniently undertaken multiple times (at least 2, 3, 4, 5, 6, 8, 10, 12, 16, 18, 24, or more times) throughout the year. In some embodiments, the frequency and/or schedule of examinations can be based at least in part on the rate of deterioration of the vision of the wearer. If the rate of deterioration increases, for example, the frequency of examinations can increase. Likewise, the examination can be performed with or without a medical professional, such as optometrist, ophthalmologist, nurse, technician, medical assistant etc.

The following paragraphs describe various example embodiments of the devices, systems, and methods described herein.

A wearable ophthalmic device, comprising: a light field processor configured to access numerical light field image data and to generate modified numerical light field image data by computationally introducing incremental amounts of positive or negative optical power to the numerical light field image data, thereby conducting an eye exam; and a head-mounted light field display configured to generate a physical light field corresponding to the modified numerical light field image data.

The device of the preceding paragraph, wherein the light field display comprises an integral imaging display with a two-dimensional array of micro-lenses and a corresponding two-dimensional array of photodetectors.

The device of any of the preceding paragraphs, wherein the light field image data comprises characters of varying sizes.

The device of any of the preceding paragraphs, further comprising a user interface configured to receive input from the user regarding the clarity of the physical light field.

The device of the preceding paragraph, wherein the light field processor is configured to incrementally change the optical power of the light field image data based on the user input.

The device of any of the preceding paragraphs, wherein the light field processor is configured to incrementally change the optical power of the light field image data based on observation of the user's eye.

The device of any of the preceding paragraphs, wherein the light field display comprises one or more infrared light sources configured to project infrared light into the user's eye to measure its accommodative state, and wherein the incremental amounts of positive or negative optical power are determined based on the accommodative state.

The device of the preceding paragraph, wherein the one or more infrared light sources are configured to project two or more infrared beams of different vergences into the user's eye to measure its accommodative state.

The device of any of the preceding paragraphs, further comprising an outward facing head-mounted light field camera configured to receive light from a user's surroundings and to generate additional numerical light field image data, wherein the light field processor is configured to computationally modify the additional numerical light field image data based on results of the eye exam.

A method of using a wearable ophthalmic device, the method comprising: accessing numerical light field image data and generating modified numerical light field image data by using a light field processor to computationally introduce incremental amounts of positive or negative optical power to the numerical light field image data, thereby conducting an eye exam; and generating a physical light field corresponding to the modified numerical light field image data using a head-mounted light field display.

The method of any of the preceding paragraphs, wherein the light field display comprises an integral imaging display with a two-dimensional array of micro-lenses and a corresponding two-dimensional array of photodetectors.

The method of any of the preceding paragraphs, wherein the light field image data comprises characters of varying sizes.

The method of any of the preceding paragraphs, further comprising receiving input from the user regarding the clarity of the physical light field using a user interface.

The method of the preceding paragraph, further comprising incrementally changing the optical power of the light field image data based on the user input.

The method of any of the preceding paragraphs, further comprising incrementally changing the optical power of the light field image data based on observation of the user's eye.

The method of any of the preceding paragraphs, further comprising projecting infrared light into the user's eye to measure its accommodative state using one or more infrared light sources in the light field display, and determining the incremental amounts of positive or negative optical power based on the accommodative state.

The method of the preceding paragraph, further comprising projecting two or more infrared beams of different vergences into the user's eye to measure its accommodative state using the one or more infrared light sources.

The method of any of the preceding paragraphs, further comprising: receiving light from a user's surroundings and generating additional numerical light field image data using an outward facing head-mounted light field camera; and computationally modifying the additional numerical light field image data based on results of the eye exam.

Retinoscopy

The wearable light field processor system described herein can be used as a retinoscope to determine vision defects of a wearer or a patient. In particular, the light field processor system can be used to detect myopia, hyperopia, astigmatisms, and/or other vision defects when operating as a retinoscope. The light field processor system can be configured to determine, for example, a refractive error of an eye of a patient by using retinoscopy techniques, such as neutralization. Neutralization includes adjusting refractive power in front of an eye until a light beam or spot swept across the eye forms an image at the retina that substantially ceases to move across the retina. The light field processor system may be configured to provide beams with differing optical correction until neutralization is achieved. The light field processor system can thus be configured to determine an optical prescription to correct identified vision defects. It should be appreciated that such a device may be used to administer an eye exam, and this exam may typically be administered at a doctor's or clinician's office or at a home by the wearer automatically. In one or more embodiments, the patient's individual light field processor system may be used, possibly with doctor supervision, or the doctor's office may have its own version of the light field processor system that may be used for diagnostic purposes. In various embodiments, this light field processor system can be configured similarly to the devices disclosed herein.

In some embodiments, the wearable light field processor system may be used to perform retinoscopy to identify vision defects using light that is swept across a wearer's eye. Examples of devices that can be configured to perform retinoscopy are described herein and include, for example and without limitation, the devices described herein with reference to FIGS. 5, 6, 7, 14, and 15. The wearable light field processor system can be configured to project a beam of light into the eye of a wearer. In some implementations, the light field processor system can be configured to display image data from the world or environment to the eye of the wearer. In this way, the wearer can see objects in the world in front of the wearer and can potentially fixate on distant or near objects depending, for example, on the type of retinoscopy test. The focus of the beam projected into the eye can be varied or otherwise provided with optical correction. As such, the wearable light field processor system can be configured to perform retinoscopy to measure refractive error of an eye of a wearer.

In some embodiments, the wearable light field processor system includes at least one light source (e.g., 714 in FIG. 14) configured to project light into the eye of the wearer. The light source(s) used for retinoscopy can be configured to provide a light beam that is swept across the eye of the wearer. In some embodiments, the wearable light field processor system also includes one or more sensors (e.g., 715 in FIG. 14) configured to measure light reflected from a retina in response to the light beam from the at least one light source being swept across the eye of the wearer. In various embodiments, the sensor(s) image the eye. The sensor(s) may comprise an eye tracking sensor or other inward facing optical sensor or camera that is configured to be directed to the eye, for example, to image the eye. The wearable light field processor system can be configured to perform retinoscopy to measure refractive error of the eye of the wearer. For example, the light field processor system can be configured to sweep the light beam across the eye of the wearer in one or more directions, to detect, measure, or image the reflection, or reflex, from the back of the eye of the wearer (e.g., the retina, the ocular fundus, etc.), and to determine vision defects through observation or measurement of the reflex. Optical correction can be computationally introduced to the light beam by the light field processor 70 and the reflex can be observed to determine when such optical correction is sufficient to offset the wearer's refractive error.

The at least one light source (e.g., 714 in FIG. 14) can be configured to provide a light beam that is moved across or around an eye of the wearer of the light field processor system. In certain implementations, the light source(s) provide a relatively narrow beam or strip of light that is moved across the eye. The beam of light may have a cross-section orthogonal to the direction of its optical path that is elongate, wherein this cross-section is longer in one direction than a perpendicular direction. Accordingly, the beam of light may form a strip of light on the eye in certain embodiments. The light provided by the light source(s) can be configured to be moved in one or more directions. When the light provided by the light source(s) is a relatively narrow beam or strip of light, the orientation of the beam or strip of light can be changed. Thus, the light source(s) can be configured to provide light that can be used to identify myopia, hyperopia, astigmatism, pigment, age-related macular degeneration, and other vision defects.

The sensor(s) (e.g., one or more of the photodetectors 715 in FIG. 14) can be configured to sense light reflected from the back of the eye or retina of the wearer (e.g., retinoscopic reflex, ret reflex, or reflex) of the light field processor system, and in various embodiments form an image the eye. Accordingly, the sensor(s) can be an image sensor or camera, one or more photodetectors, or other device that can provide a signal in response to detected light and possibly an image of the eye. In some embodiments, the sensor(s) can include one or more filters (e.g., bandpass filters tuned to pass bands of wavelengths that are expected for the reflex) tailored to preferentially pass the reflex from the eye of the wearer and to preferentially block light in other wavelength bands. The filters can be physical filters and/or filters applied in signal or image processing software.

The light source(s) and the sensor(s) (e.g., camera) can be coupled to a control system (e.g., the light field processor 70) that is configured to process information about the characteristics, direction, orientation, and/or position of the light provided by the light source(s) and to process information about the characteristics, direction, orientation, and/or position of the light detected by the sensor(s). From this information, the control system can be configured to determine one or more vision defects of the eye of the wearer. In some embodiments, the control system can be configured to modify the light provided by the light source(s) (e.g., the direction, orientation, as well as optical correction provide to the beam etc.) based at least in part on analysis of the light detected by the sensor(s). In some embodiments, the control system is configured to perform a pre-defined routine to determine vision defects. In some embodiments, the control system can adapt a retinoscopy routine based on results of analysis of the light detected by the sensor(s) at any point during the routine.

The light field processor system can be configured to project images to the wearer. As described herein, the light field processor system can provide images to the wearer corresponding to different apparent depth planes, both far and near. Accordingly, the wearer can fixate on the display, looking at images that simulate far and near objects. In this manner, the wearer can have either relaxed accommodation or may exhibit accommodation depending on the test.

The light field processor system can thus be configured to provide static and/or dynamic retinoscopy. For static retinoscopy, for example, the light field processor system can be configured to determine refractive errors when the wearer has relaxed accommodation. For dynamic retinoscopy, for example, the light field processor system can be configured to perform retinoscopy while the wearer accommodates at different distances. This can be accomplished by providing virtual images or objects on which the wearer focuses while performing retinoscopy. The apparent distance to the image or object can be changed while accommodation of the eye is tracked through the methods and systems described herein. Distance to the image can be changed by the light field processor 70 by varying the apparent depth plane in a manner such as described herein. For example, the light field processor can vary the curvature of wavefronts of image data projected into the eye to correspond to a specific focal length and associated depth plane. The apparent distance from the eye to the depth plane can thus be known. In some cases, the light field processor 70 which controls the projected beam has variable optical power that can be selected or adjusted computationally. Accordingly the apparent depth planes can be changed or adjusted as desired in such cases. Alternatively, or in addition, apparent distance to an object can also be changed by placing an actual object in the world in front of the wearer and within the field of view of the wearer that is seen through the display of the light field processor system (e.g., via the integral imaging camera 16), as described herein. Either of these approaches can be used to determine, for example, the wearer's accommodative response to changes in target distance. These approaches can also be used to determine, for example, the eye's near point. This can be compared to static retinoscopy that determines, among other things, the eye's far point.

The wearable light field processor system can include one or more user interface features configured to allow a wearer or other person to provide input to the device. The user interface features can be integrated with the device. In some implementations, the user interface features are provided by a device or component that is not physically integrated with the device. For example, the user interface features can be provided by a device or system that is in communication with the device. This can be a smartphone, computer, tablet, or other computational device that is in wired or wireless communication with the device. In some embodiments, the user interface features can be provided by a combination of different devices and systems linked to the device, e.g., through wired or wireless communication networks or through components that are physically linked to the device or integrated with the device. The user interface features can be presented on a device with a touch screen wherein interaction with the touch screen provides input to the wearable light field processor system. Voice recognition systems as well as virtual touch capability may be included in addition or as an alternative. Accordingly, the user interface features can include capacitive features sensitive to touch, keyboards, buttons, microphones, photodetectors, cameras or tracking sensors for tracking gestures such as pointing by the wearer or a variety of software-implemented features provided by a graphical user interface. In various embodiments, a virtual touch screen is provided through the images projected to the user's eyes and sensors to sense the users moving body, e.g., finger. In some embodiments, the user interface features include gesture detection components to allow a wearer to provide user input through gestures. In some embodiments, the user interface features include gaze detection components to allow a wearer to provide user input through gaze of the eyes (e.g., this can include selecting a button or other element when the wearer fixates on the button for a time or when the wearer blinks when fixated on the button). Such user interface systems can be employed for other devices and systems described herein.

In some implementations, the wearer, clinician or doctor can use the interface features to control aspects of the retinoscopy test. This can be done, for example, to change the characteristics of the image or light being provided and/or the depth plane from which the light or image is being projected. This can be used to alter the light and optical correction being provided to the wearer to determine an appropriate optical prescription for the wearer.

In some embodiments, the light field processor system may be configured to provide both static and dynamic retinoscopy. Since the focus of images can be dynamically modified through the light field processor 70, both types of retinoscopy may be performed with the same device. It should be appreciated that the light field processor system may also provide a static or swept path of light to the retina. This may be a light beam projected by a light source such as the integral imaging display 62. In some implementations, the light field processor system may comprise an additional component that is configured to sweep light across the retina or otherwise move light on the retina. The light field processor system can be used to perform retinoscopy and objectively determine refractive errors, which may be advantageous over other instruments that use subjective feedback from patients to determine refractive errors.

To provide static retinoscopy, the light field processor system is used when the accommodation of the eye of the wearer is relaxed. This can be accomplished, for example, through the use of cycloplegic drops in the eye of the wearer. A light spot or beam can be provided and moved across the eye of the wearer. Computational refractive corrections that can alter the shape of the wavefront can be applied to neutralize or compensate for vision defects. In some embodiments, when operating as a static retinoscope, an image provided by the light field processor system for the view used to fixate can be provided from an apparent depth plane that is far, e.g., effectively at infinity. In some embodiments, when operating as a static retinoscope, the light provided by the light field processor system that is swept across the eye can be provided from a static apparent depth plane. The apparent depth plane from which the virtual image is projected can be placed between infinity and about 0.1 m. In certain implementations, the light field processor system includes a spray or other delivery device to deliver eye drops or a spray used to dilate the pupil and/or relax accommodation of the eye of the wearer. For example, the light field processor system can be configured to spray cycloplegic drops in the eye of the wearer.

To provide dynamic retinoscopy, the light field processor system can be used when the eye of the wearer is allowed to accommodate. An image can be displayed to the wearer or an object can be provided for the wearer to fixate on. The apparent distance of the image or object can be varied so as to induce accommodation. In some embodiments, the accommodation of the eye of the wearer can be observed and/or measured. Using this technique, accommodation lag or lead may be measured.

The light field processor systems described herein can be used to switch between static retinoscopy and dynamic retinoscopy. This can be accomplished while the light field processor system is in use. The light field processor system can be configured to provide images from a variety of apparent depth planes for the wearer to view, allowing both static and dynamic retinoscopy to be performed. For example, the image provided by the light field processor system can be dynamically modified to switch between static retinoscopy and dynamic retinoscopy.

As was the case in previous embodiments, input may be received by the wearer to determine diagnosis. In some embodiments, the light field processor system may also include an eye scanning module configured to measure the response of the retina to the swept light. This response may be recorded and analyzed based on retinoscopy-specific algorithms to provide a diagnosis to the patient. For example, algorithms can be based at least in part on retinoscopy where a light is swept across an eye and the reflex is observed and measured wherein refractive errors are associated with observed or measured characteristics of the reflex. In some implementations, the direction of the reflex movement can be used to determine refractive errors. If, for example, the reflex moves in the same direction as the light that is swept across the eye, or demonstrates "with" movement, the light field processor system can determine that the eye of the wearer is hyperopic. Similarly, if the reflex moves in the opposite direction as the light that is swept across the eye, or demonstrates "against" movement, the light field processor system can determine that the eye of the wearer is myopic. If the reflex moves in a direction that is not parallel to the direction that the light is swept across the eye, the light field processor system can determine that the eye of the wearer is astigmatic. In addition, the direction of movement of the reflex relative to the direction of movement of the light provided to the eye can indicate whether positive or negative refractive power is required to correct the vision defect. For example, "with" movement indicates positive refractive power may be required to correct the refractive error, "against" movement indicates negative refractive power may be required, and oblique movement indicates cylindrical refractive power may be required. As described above, different optical correction (e.g., sphere and/or cylinder with varying axes) can be provided to determine the wearer's prescription and suitable refractive correction.

In some implementations, the speed of the reflex, combined with a virtual working distance of the light field processor system, may also be used to determine characteristics of a visual defect. For example, the speed of the reflex can be correlated to the ametropia or refractive error of the eye (e.g., faster speeds indicate lower ametropia or smaller refractive errors of the eye).

In some implementations, the width of the reflex may also be used to determine characteristics of a visual defect. For example, the width of the reflex can be correlated to the refractive error of the eye (e.g., wider reflexes indicate lower ametropia or smaller refractive errors of the eye).

In some implementations, the orientation of the reflex relative to the source light beam may also be used to determine characteristics of a visual defect. For example, a rotation of the orientation of the reflex relative to the source light beam can be indicative of astigmatism.

In some implementations, the relative brightness of the reflex may also be used to determine characteristics of a visual defect. For example, the relative brightness of the reflex can be used to determine the refractive error of the eye (e.g., brighter reflexes indicate lower ametropia or smaller refractive errors of the eye).

Any combination of the above characteristics of the reflex may be used as well to determine refractive errors. Similarly, changes in the above characteristics of the reflex may be used, alone or in any combination with one another, to determine whether refractive corrections improve or worsen the determined refractive error, where the refractive corrections are applied by the light field processor system and/or resulting from the addition or subtraction of refractive optical components or other components that introduce optical correction. In some embodiments, the light field processor system can be configured to determine in real time whether refractive corrections improve or worsen the determined refractive error. The light field processor system can be configured to measure or monitor accommodation reflex by measuring accommodation, vergence, and/or pupils size and fluctuations in these physical characteristics to assess whether the wearer is able to see an image with normal visual acuity. For example, the accommodation, vergence, and/or pupil size of an eye fluctuate when fixated on a stationary target. These fluctuations increase when the eye is having trouble focusing on the image. Accordingly, the light field processor system can be configured to monitor fluctuations in the characteristics of the eye and uses this biofeedback to assess the quality of the image seen by the wearer (e.g., whether the wearer is seeing an object or image with normal visual acuity).

Figure 17:
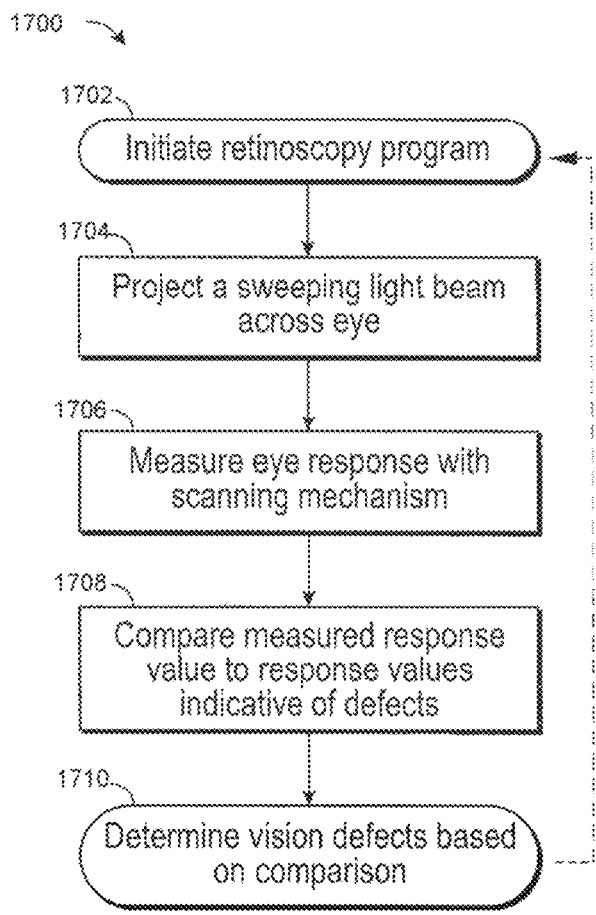
FIG. 17 illustrates an example method for measuring refractive error of a wearer of a light field processor system configured as an ophthalmic device to perform retinoscopy.

FIG. 17 illustrates an example method 1700 for measuring refractive error of a wearer of a light field processor system configured as an ophthalmic device to perform retinoscopy. For ease of description, the method 1700 will be described as being performed by a light field processor system, such as the ones described herein. However, some components or subparts of the various light field processor systems disclosed herein or other similar devices may be used to perform some steps, combinations of steps, or portions of a step in the method 1700.

At block 1702, the light field processor system initiates a retinoscopy program. The retinoscopy program can be a stored process or sequence of functions provided by the light field processor system. Initiating the retinoscopy program can include determining or retrieving a starting optical prescription, such as for a wearer that has previously undergone a retinoscopy test or other eye exam. In some implementations, the retinoscopy program can integrate information about ocular anomalies of the wearer's eye(s), where the information about the ocular anomalies can be entered by the wearer or clinician, determined from a previous retinoscopy program, or retrieved from a data store (e.g., a data store that is part of the light field processor system or a networked data store). Initiating the retinoscopy program can include the light beam to be projected to the wearer. Initiating the retinoscopy program can include determining whether a clinician or doctor is administering the eye exam or whether the examination is being self-administered by the wearer. In some embodiments, the light field processor system initiates the retinoscopy program in response to input received from the wearer or a clinician.

At block 1704, a beam of light is swept through the wearer's eye. The light can be, for example, a beam (e.g., a spot projected into the eye). The light may be collimated, converging, or diverging. The light can be swept across the eye or otherwise moved around the eye. The beam of light can be provided with an amount of optical correction/power to be tested (e.g., sphere and/or cylinder (with varying axes)), to determine defocus error and astigmatism.

At block 1706, an eye scanning component of the light field processor system is configured to measure a response of the wearer's eye in response to the swept light (e.g., reflex from the wearer's eye). The eye scanning component can be a camera or other sensor described herein (e.g., the integral image display 62, as controlled by the light field processor 70). The eye scanning component can be configured to analyze the measurements of the reflex to determine refractive errors. For example, the component (e.g., camera) can include analysis modules that are configured for a pattern recognition measurement, response pattern identification, sensor measurement, reflex tracking, brightness measurements, speed tracking, orientation determination, or the like. The retinoscope program may be pre-coded with pattern recognition algorithms to identify patterns and/or to analyze a given pattern. The retinoscope program may be pre-coded with previous images from the wearer to identify changes in a historical analysis.

At block 1708, the wearer's eyes' response may be compared against a correlation table that holds corresponding response values of various vision defects. For example, at block 1708, the light field processor system compares the information measured in block 1706 with a correlation table or other data corresponding to expected values of measurements for various vision defects. The comparison can be used to determine refractive errors based on the characteristics of the reflex measured in block 1706.

At block 1710, the values are compared in order to determine any vision defects. Examples of characteristics and their relationship with vision defects are described herein above. For example, the direction, speed, brightness, and/or width of the reflex can be used to determine refractive error. The shape of the reflex can be used to determine other vision defects such as astigmatism. In some embodiments, testing can be initiated if the wearer is struggling to focus or when problems with their vision occur, as represented by the dotted line from block 1710 to block 1702.

In various embodiments, to reduce distraction, the view of the world in front of the wearer's eyes through the light field processor system is blocked or otherwise not visible during retinoscopy. This can occur, for example, when images are presented to the wearer, although this approach is not necessary. In some embodiments, eye tracking, head pose (e.g., head orientation and gaze direction) tracking, and/or tracking of eye or facial tissue can be employed to monitor whether the wearer is distracted or fatigued. The system can be configured to dynamically filter out distractions based on the results of monitoring an eye tracking system.

The light field processor system may be a system provided by the physician or clinician for testing at a medical facility or optometrist office or elsewhere. In other embodiments, the system may belong to the wearer and may be employed for other purposes such as entertainment (e.g., games and movies) and/or work activities. As described above, one benefit of implementing retinoscopy on the wearer's system is that the procedure can be conveniently undertaken multiple times (at least 2, 3, 4, 5, 6, 8, 10, 12, 16, 18, 24, or more times) throughout the year. In some embodiments, the frequency or schedule of the procedure can be altered based on results and/or trends of retinoscopy test results. For example, if the test results indicate that vision defects are deteriorating or if the system detects the wearer is struggling with their vision (e.g., through analysis of accommodation fluctuations, vergence fluctuations, etc.), the frequency or schedule of the procedure can be altered to increase the frequency of procedures and/or shorten the time between procedures. Likewise, the procedure can be performed with or without a medical professional, such as optometrist, ophthalmologist, nurse, technician, medical assistant etc.

The following paragraphs describe various example embodiments of the devices, systems, and methods described herein.

A wearable ophthalmic device, comprising: a head-mounted light field display configured to generate a physical light field comprising a beam of light and to sweep the beam of light across a user's eye, thereby producing a retinal reflex; a head-mounted photodetector array configured to receive the retinal reflex and to generate numerical image data; and a light field processor configured to computationally introduce an amount of positive or negative optical power to the beam of light, and to determine an optical prescription for the user's eye based on the retinal reflex response to the beam of light.

The device of the preceding paragraph, wherein the photodetector array is part of a light field camera and the numerical image data comprises numerical light field image data.

The device of any of the preceding paragraphs, wherein the light field display comprises an integral imaging display.

The device of any of the preceding paragraphs, wherein the photodetector array is integrated with the light field display.

The device of the preceding paragraph, wherein the light field display comprises a microlens array shared with the light field camera.

The device of any of the preceding paragraphs, further comprising an outward facing head-mounted light field camera configured to receive light from a user's surroundings and to generate numerical light field image data, wherein the light field processor is configured to computationally modify the numerical light field image data based on the optical prescription.

A method for using a wearable ophthalmic device, the method comprising: generating a physical light field comprising a beam of light and sweeping the beam of light across a user's eye using a head-mounted light field display, thereby producing a retinal reflex; receiving the retinal reflex and generating numerical image data using a head-mounted photodetector array; and computationally introducing an amount of positive or negative optical power to the beam of light and determining an optical prescription for the user's eye based on the retinal reflex response to the beam of light using a light field processor.

The method of the preceding paragraph, wherein the photodetector array is part of a light field camera and the numerical image data comprises numerical light field image data.

The method of any of the preceding paragraphs, wherein the light field display comprises an integral imaging display.

The method of any of the preceding paragraphs, wherein the photodetector array is integrated with the light field display.

The method of the preceding paragraph, wherein the light field display comprises a microlens array shared with the light field camera.

The method of any of the preceding paragraphs, further comprising: receiving light from a user's surroundings and generating numerical light field image data using an outward facing head-mounted light field camera; computationally modifying the numerical light field image data based on the optical prescription.

Autorefractor

In one or more embodiments, the ophthalmic devices described herein (e.g., the light field processor system 600) may be configured to function as an autorefractor. An autorefractor provides an objective measurement of a person's refractive error. In contrast to a phoropter which may involve subjective responses from the patient, the autorefractor does not rely on responses from the user. A cycloplegic agent (e.g., eye drops) may be used to keep the ciliary muscles in a relaxed position, resulting in a loss of accommodation of the user. This relaxed position of the eye provides for a more consistent view of the retina. The patient may be asked to view an image projected by the autorefractor device. The image may move in and out of focus across depth planes as the machine takes readings to determine when the image is on the retina. The machine may average the results to determine a prescription.

To this end, the ophthalmic device may use a display (e.g., the integral imaging display 62, as controlled by the light field processor 70) to provide one or more images at varying apparent depths, and scanning, through an eye-scanning module (e.g., the photo sensors 715 in FIG. 14), to capture images of the retina while the eye is focused at the images of varying apparent depths. As was the case in previous examples, various algorithms may be used to determine when the patient properly focuses on the image, and subsequently determine an optical prescription for the user. The processor of the ophthalmic device may be used to perform a number of objective refractive examinations using visible or infrared light. In one or more embodiments, image quality analysis/contrast peak detection techniques may be used in analysis. Similarly, the Scheiner double pinhole alignment, Shack-Hartmann grid alignment and/or the retinoscopic reflex neutralization may be used as well.

In some embodiments, the light field processor system 600 in FIG. 14 can be configured as an autorefractor. As already discussed, the system 600 can be head-mounted so as to be aligned with a user's eye. The autorefractor system could be a binocular autorefractor capable of testing the refraction of both eyes of a patient simultaneously.

The integral imaging display 62 can be used, in conjunction with the light field processor 70, to transmit light with varying amounts of wavefront curvature to the eye. For example, the integral imaging display 62 can transmit light beams to the eye with different amounts of vergence, including light beams with positive vergence or negative vergence, as well as collimated beams. The amount of vergence can be controlled by the light field processor 70 based on the wavefront curvature of the image data provided to the integral imaging display 62. This can be done computationally without requiring physical lenses to change the vergence of the beam. The light provided by the light sources 714 can be in the visible or infrared spectrum.

As just described, the integral imaging display 62 can be used to controllably provide beams of light to the eye with a range of different vergences, from beams with positive vergence to collimated beams to beams with negative vergence. The beams of light which are output from the integral imaging display 62 propagate toward the user's eye along the visual axis. In some embodiments these beams may be transmitted through a beamsplitter which can be provided between the integral imaging display 62 and the eye. Such a beamsplitter could be aligned with the visual axis of the eye and could allow a separate camera to view the eye.

As already discussed, the autorefractor system can provide image data to the eye using beams of light with varying degrees of vergence. As this image data is provided to the eye, the photodetectors 715 in the integral imaging display 62 (or a separate camera that views the eye through a beam splitter camera) can be used to monitor the retina of the eye. The photodetectors 715 can provide retinal images to the light field processor 70. The light field processor 70 can then perform image processing algorithms on the retinal images to determine when the image data projected by the autorefractor system is best focused on the retina of the eye. Such image processing algorithms can include, for example, contrast peak detection. (Image data projected on the retina of the eye will generally have relatively low contrast when the image data is blurred and peak contrast when the image data is sharply focused by the eye.) The light field processor can calculate the refractive power of the eye based on the degree of vergence (whether positive, collimated, or negative) required to allow the eye to focus light on the retina. The light field processor 70 can determine image quality in multiple meridians in order to calculate not only spherical power of the eye but also cylindrical power and axis.

The light field processor can control the operation of the autorefractor system. In one example embodiment, the control method can include causing one or more of the light sources 714 to project an image toward the eye using beams of light having a first vergence value (whether positive, collimated, or negative). The light field processor 70 can then capture an image of the retina of the eye using the camera photodetectors 715. The light field processor 70 can analyze the captured retinal image to determine a metric of the quality of the image formed on the retina when using beams of light having the first vergence value.

The light field processor can then cause one or more of the light sources 714 to project the image toward the eye using beams of light having a second vergence value that is different from the first vergence value. The light field processor 70 can then once again capture an image of the retina of the eye using the photodetectors 715 and analyze the retinal image to determine a metric of the quality of the image formed on the retina when using beams of light having the second vergence value. The light field processor 70 can then compare the first image quality metric with the second image quality metric. Based on this comparison, the light field processor 70 can select a third vergence value to use when projecting the image toward the eye using any of a variety of optimization algorithms. The light field processor 70 can then calculate a third image quality metric indicative of the quality of the image formed on the retina when using beams of light having the third vergence value. This process can be performed iteratively until the image quality metric is maximized or otherwise determined to be sufficient. Finally, the light field processor can compute the refractive power of the eye based on the vergence value corresponding to this image quality metric. In addition, the light field processor 70 can initiate execution of the phoropter method described herein if the autorefractor system identifies refractive error(s) above a threshold. The phoropter system can be used as check on the accuracy of the measurements by the autorefractor system, or vice versa. In this way, the autorefractor system and the phoropter system described herein can be used jointly to characterize a patient's vision.

Figure 18A:
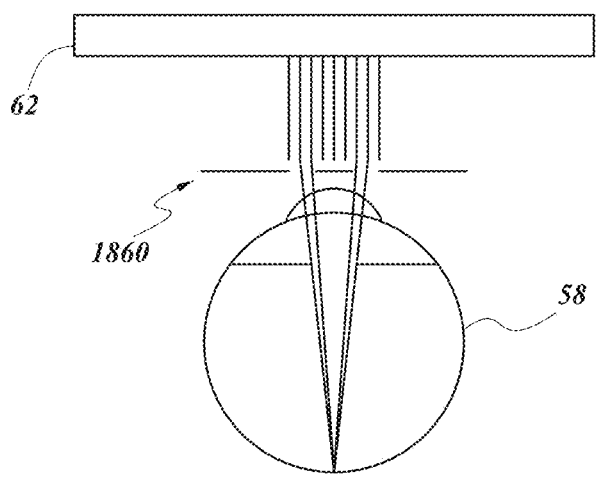
FIGS. 18A-18C illustrate an example embodiment of an augmented and/or virtual reality system configured as an autorefractor.

FIG. 18A illustrates another example embodiment of an augmented and/or virtual reality system configured as an autorefractor. The autorefractor system can include all of the features of the autorefractor system 600 illustrated in FIG. 14 (though the light field processor 70 and the integral imaging camera 16 are not shown). In addition, the autorefractor system illustrated in FIG. 18A can include a Scheiner's pinhole disc 1860 located along the optical path of the system before the eye 58. The Scheiner's disc 1860 can be located, for example, between the integral imaging display 62 and the eye 58. This is an opaque disc with two or more small apertures. As illustrated in FIG. 18A, when a collimated beam of light is incident upon the Scheiner's disc 1860, the beam is blocked from being transmitted to the eye except for rays of light which are able to pass through the two apertures. In the case of an emmetropic eye, the rays of light transmitted through each of the two apertures are focused to a common spot on the retina of the eye 58. Thus, a retinal image taken by the photo sensors 715 would reveal a single spot.

Figure 18B:
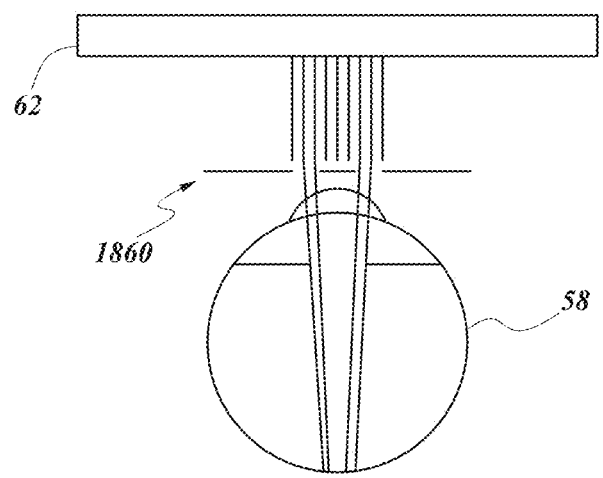
Figure 18C:
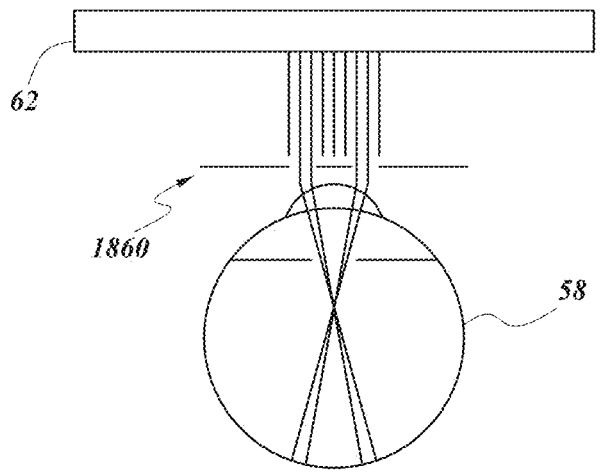

While FIG. 18A illustrates the effect on an emmetropic eye of a collimated beam passing through a Scheiner's disc 1860, FIGS. 18B and 18C respectively show the same effect on a hyperopic eye and on a myopic eye. As seen in FIG. 18B, the optical power of the hyperopic eye is not strong enough to focus the rays of light transmitted through the two apertures of the Scheiner's disc 1860 to a single spot. Thus, a retinal image taken by the photo sensors 715 would reveal two distinct spots in the case of a collimated beam illuminating a Scheiner's disc in front of a hyperopic eye. As seen in FIG. 18C, the optical power of the myopic eye is too strong, which results in the rays of light transmitted through the two apertures of the Scheiner's disc 1860 being focused in front of the retina. This, too, results in two distinct spots being formed on the retina.

The autorefractor system 600 can therefore vary the vergence of the beam of light which is incident upon the Scheiner's disc until a single spot is formed on the retina of the eye. The refractive power of the eye 58 can be calculated based on the beam vergence required to form a single spot on the retina.

The light field processor 70 can control the operation of the autorefractor system 600. In one example embodiment, the control method can include causing one or more of the light sources 714 to project a beam of light having a first vergence value (whether positive, collimated, or negative) onto the Scheiner's disc 1860. The light field processor 70 can then capture an image of the retina of the eye 58 using the photo sensors 715. The light field processor 70 can analyze the retinal image to determine the number of spots which are evident. If only a single spot is evident, the processor can calculate the refractive power of the eye 58 based on the first vergence value. Alternatively, if multiple spots are evident, the processor 2606 can select a second vergence value that is different from the first vergence value. The light field processor 70 can then cause a beam of light having the second vergence value to be projected onto the Scheiner's disc 1860. The light field processor 70 can once again capture an image of the retina of the eye 58 using the photo sensors 715 and analyze the retinal image to determine the number of spots which are evident. If a single spot is evident, the light field processor 70 can calculate the refractive power of the eye 58 based on the second vergence value. Otherwise, the third vergence value can be selected and the process can be iteratively repeated until a single spot is formed on the retina. The light field processor 70 can then compute the refractive power of the eye 58 based on that vergence value.

Any of the autorefractor or other diagnostic methods described herein can be used for real-time adjustments while the user is watching content to ensure the content is focused. In addition, monitoring of the user's refractive error can be performed on a long term basis (e.g., weeks, months, or years) to provide longitudinal monitoring and analysis of the user's refractive error. The frequency of regularly-scheduled tests may be automatically adjusted based on trending of the test.

The following paragraphs describe various example embodiments of the devices, systems, and methods described herein.

A wearable ophthalmic device, comprising: a head-mounted light field display configured to generate a physical light field comprising a beam of light and to direct the beam of light into a user's eye, thereby producing a retinal reflex; a head-mounted photodetector array configured to receive the retinal reflex and to generate numerical image data; and a light field processor configured to control the light field display, to analyze the retinal reflex using the numerical image data, and to determine an optical prescription for the user's eye based on the analysis of the retinal reflex.

The device of the preceding paragraph, wherein the light field processor is further configured to computationally introduce an amount of positive or negative optical power to the beam of light based on the analysis of the numerical image data.

The device of any of the preceding paragraphs, wherein the photodetector array is part of a light field camera and the numerical image data comprises numerical light field image data.

The device of any of the preceding paragraphs, wherein the light field display comprises an integral imaging display.

The device of any of the preceding paragraphs, wherein the photodetector array is integrated with the light field display.

The device of any of the preceding paragraphs, further comprising a disc with at least two pinholes, the disc being positioned in front of the eye such that the beam of light passes through the pinholes.

The device of any of the preceding paragraphs, wherein the light field processor is configured to analyze the retinal reflex to determine the focus of the light on the retina.

The device of any of the preceding paragraphs, further comprising an outward facing head-mounted light field camera configured to receive light from a user's surroundings and to generate numerical light field image data, wherein the light field processor is configured to computationally modify the numerical light field image data based on the analysis of the retinal reflex.

A method of using a wearable ophthalmic device, the method comprising: generating a physical light field comprising a beam of light and directing the beam of light into a user's eye using a head-mounted light field display, thereby producing a retinal reflex; receiving the retinal reflex and generating numerical image data using a head-mounted photodetector array; and controlling the light field display, analyzing the retinal reflex using the numerical image data, and determining an optical prescription for the user's eye based on the analysis of the retinal reflex using a light field processor.

The method of the preceding paragraph, further comprising computationally introducing an amount of positive or negative optical power to the beam of light based on the analysis of the numerical image data using the light field processor.

The method of any of the preceding paragraphs, wherein the photodetector array is part of a light field camera and the numerical image data comprises numerical light field image data.

The method of any of the preceding paragraphs, wherein the light field display comprises an integral imaging display.

The method of any of the preceding paragraphs, wherein the photodetector array is integrated with the light field display.

The method of any of the preceding paragraphs, further comprising transmitting the beam of light through a disc with at least two pinholes, the disc being positioned in front of the eye.

The method of any of the preceding paragraphs, further comprising analyzing the retinal reflex to determine the focus of the light on the retina using the light field processor.

The method of any of the preceding paragraphs, further comprising: receiving light from a user's surroundings and generating numerical light field image data using an outward facing head-mounted light field camera; and computationally modifying the numerical light field image data based on the analysis of the retinal reflex.

Aberrometer

In one or more embodiments the light field processor system 600 may function as an aberrometer. An aberrometer measures irregularities in the eye, possibly including defocus, regular astigmatism, and higher-order aberrations (e.g., spherical aberration, coma, trefoil, irregular astigmatism). Even higher-order aberrations can have a significant impact on the quality of vision, and may affect depth perception, contrast, color perception, night vision, etc. Identifying higher-order aberrations in addition to lower-order aberrations can help produce more accurate prescription eye wear.

In order to identify refractive errors, the aberrometer may send a beam of light into the eye. In some embodiments the beam of light is infrared light. The light passes through the cornea and the lens of the eye and is reflected back by the retina. The reflected light may then be measured by the aberrometer to produce data regarding the refractive errors (including higher-order refractive errors) of the eye. Aberrometers are often used to gather data for the performing laser vision correction surgery. The map created by the aberrometer directs the delivery of laser light that precisely re-shapes the cornea.

In some embodiments, an aberrometer system can include elements of the light field processor system 600. For example, an aberrometer system can include the light field processor 70 and the integral imaging display 62. In some embodiments, the integral imaging display is the sort illustrated in FIG. 14, which includes photo sensors 715. The integral imaging display 62 of the light field processor system 600 may be used to produce light having a desired wavefront. As was the case in previous embodiments, the response to the applied stimulus may be measured. It should be appreciated that wavefronts of different frequencies may be applied. Similarly, visible or non-visible light may be projected into the eye. In one or more embodiments, the captured data may be processed to determine any abnormalities.

The wavefronts of light which are output from the integral imaging display 62 propagate toward the user's eye along the visual axis. In some embodiments, the integral imaging display 62 outputs a probe beam of light having planar wavefronts. But the integral imaging display 62 can also be controlled by the light field processor to output a probe beam having positive or negative optical power. The probe beam enters the eye 58 and is eventually backscattered by the retina. As the probe beam propagates through the eye, its planar wavefronts can be affected by irregularities or imperfections in the optics of the eye 58. Such irregularities or imperfections can cause the wavefronts to likewise become irregular.

Once the backscattered probe beam exits the eye, it propagates back toward the integral imaging display 62. These wavefronts which exit the eye are typically irregular. The specific shape of the aberrated wavefronts is dependent upon the irregularities or imperfections in the eye 58. The system may include a relay lens system that relays the wavefronts at approximately the pupil plane of the eye to the array 712 of micro lenses.

The array of micro lenses 712, in conjunction with the photo sensors 715, can act as a wavefront aberrometer which is capable of measuring and characterizing the shape of these wavefronts. Specifically, a Shack-Hartmann type wavefront sensor. The array of lenslets 712 spatially sample the incident wavefronts at many different locations. The photo sensors 715, which can be for example CCD or CMOS elements, can act as a detector. Each lenslet focuses a spot of light on the detector. The precise location of each spot on the detector depends upon the local curvature of the wavefront at the location of the corresponding lenslet. The detector therefore creates an image which consists of an array of spots. This image can be analyzed by the light field processor 70 to determine the precise location of each spot, which is in turn indicative of the wavefront curvature at the location of the corresponding lenslet. In this way, the light field processor 70 can determine the curvature of the wavefront at each spatial location sampled by the lenslet array. Based on the shape of a measured wavefront, the processor can calculate aberrations of the eye, including both lower-order and higher-order aberrations. These aberrations can be represented numerically as, for example, Zernike coefficients.

Once the light field processor 70 has determined the aberrations of the eye 58, it can output those measurements in, for example, numerical or graphical form. The measurements can be used to determine a treatment plan for the eye 58, such as a corrective optical prescription. In addition, the measurements of the aberrations of the eye 58 can be used by the light field processor to computationally correct incoming image data from the integral imaging camera 16, thus providing a crisper image to the user. For example, in some embodiments, the light field processor 70 can be used to computationally control the shape of the wavefronts output by the integral imaging display 62 as it projects virtual and/or augmented reality image data into the eye 58. In this way, the image data provided to the user can be specially corrected based upon the higher and/or lower aberrations of the user's own eye(s).

The following paragraphs describe various example embodiments of the devices, systems, and methods described herein.

A wearable ophthalmic device, comprising: a head-mounted light field display configured to generate a physical light field comprising a beam of light and to direct the beam of light into a user's eye, thereby producing a retinal reflex; a head-mounted light field camera configured to receive the retinal reflex and to generate numerical light field image data; and a light field processor configured to control the light field display, to analyze the retinal reflex using the numerical light field image data, and to determine higher-order aberrations of the eye based on the analysis of the retinal reflex.

The device of the preceding paragraph, wherein the light field processor is further configured to computationally introduce an amount of positive or negative optical power to the beam of light.

The device of any of the preceding paragraphs, wherein the light field display comprises an integral imaging display.

The device of any of the preceding paragraphs, wherein the light field camera is integrated with the light field display.

The device of the preceding paragraph, wherein the light field display comprises a microlens array shared with the light field camera.

The device of the preceding paragraph, wherein the light field camera comprises a Shack-Hartmann sensor.

The device of any of the preceding paragraphs, further comprising an outward facing head-mounted light field camera configured to receive light from the user's surroundings and to generate additional numerical light field image data, wherein the light field processor is configured to computationally modify the additional numerical light field image data based on the higher-order aberrations of the eye.

A method of using a wearable ophthalmic device, the method comprising: generating a physical light field comprising a beam of light and directing the beam of light into a user's eye using a head-mounted light field display, thereby producing a retinal reflex; receiving the retinal reflex and generating numerical light field image data using a head-mounted light field camera; and controlling the light field display, analyzing the retinal reflex using the numerical light field image data, and determining higher-order aberrations of the eye based on the analysis of the retinal reflex using a light field processor.

The method of the preceding paragraph, further comprising computationally introducing an amount of positive or negative optical power to the beam of light using the light field processor.

The method of any of the preceding paragraphs, wherein the light field display comprises an integral imaging display.

The method of any of the preceding paragraphs, wherein the light field camera is integrated with the light field display.

The method of the preceding paragraph, wherein the light field display comprises a microlens array shared with the light field camera.

The method of the preceding paragraph, wherein the light field camera comprises a Shack-Hartmann sensor.

The method of any of the preceding paragraphs, further comprising: receiving light from the user's surroundings and generating additional numerical light field image data using an outward facing head-mounted light field camera; and computationally modifying the additional numerical light field image data based on the higher-order aberrations of the eye using the light field processor.

Macular Degeneration

In one or more embodiments, the light field processor system 600 may be configured to detect, diagnose and/or compensate for macular deficiencies. Macular deficiencies (e.g., holes, cysts, degeneration, etc.) are damages at the macular and foveal tissue in the retina that create anomalies, dead spots or regions of reduced sensitivity to light or devoid of sensitivity to light in the user's field of view. Common forms of macular deficiency include age-related macular degeneration (AMD), Stargardt disease, Best disease, and other degenerative conditions. Age-related macular degeneration includes "dry" AMD, characterized by atrophy of the retinal pigment epithelial layer, and "wet" AMD, in which vision loss occurs due to complications from abnormal blood vessel growth in the retina. Macular deficiencies may result in anomalies, dead spots or regions of reduced sensitivity to light in various parts of the field of view, as well as loss of contrast or color sensitivity. Frequently, anomalies, dead spots or regions of reduced sensitivity occur near the center of the field of view rather than at the periphery.

The light field processor system 600 may be configured to detect or diagnose macular deficiencies by determining the ability of a portion of the retina to detect an image. In some embodiments, the light field processor system may include a user display device 62, such as the integral imaging display shown in FIGS. 6, 7, and 14 which can project light into the eye of a wearer to form an image in the eye. The user display device 62 may include a display lens, screen, etc. 106 which may be mounted to a user's head or eyes by a housing or frame 108.

The system can then detect a response from the wearer. For example, the image may be a small dot that can be clearly seen if projected to a healthy portion of the retina but likely would not be seen if projected to a deficient portion. In some embodiments, the wearer may be prompted automatically or by another user, such as a medical professional, to indicate if the wearer saw an image. The user may then input the wearer's response through a user interface. In some embodiments, the light field processor system may increase accuracy by using the photo sensors 715 in the integral imaging display device 62, separate eye tracking cameras 24, or similar detection methods to observe if an involuntary reaction occurs in response to the projection of the image, such as a change in focus or gaze or continued eye scanning, without requiring a conscious input. Eye tracking cameras 24 may be inward-facing (i.e., directed toward the user's eye) cameras, as illustrated in FIG. 5. In some embodiments, the light field processor system may directly prompt the wearer to indicate if the image was observed, such as by a manual input or by consciously directing the wearer's gaze to the image or to a projected virtual button image. A virtual button image may be projected by the display lens 106, and the wearer's selection of the button may be detected by the eye tracking cameras 24 or through gesture recognition.

In some embodiments, the test described above may be repeated at different portions of the retina, or with different images at the same portion of the retina, to detect areas of macular deficiency. For example, a particular portion of the retina where an image can be seen by the wearer may be determined to be healthy, while a portion of the retina where the same image cannot be seen may be determined to be deficient. In another example, an image consisting primarily of longer wavelength visible light, such as red light, may first be projected. An image consisting primarily of shorter wavelength visible light, such as blue light, may then be projected to the same portion of the retina, and any disparity in visibility to the wearer may be indicative of a loss of color sensitivity in the wearer. In some embodiments, a plurality of images differing in contrast, saturation, hue, intensity, periodicity or spatial frequency, or any other characteristic may be presented to the wearer at different locations on the wearer's retina so as to diagnose various sensitivity losses due to macular deficiencies. Images of the wearer's retina may be used in addition to the results of the testing described above to improve the reliability of macular deficiency diagnosis. Such images may be obtained, for example, by the system described with respect to FIG. 14, an ophthalmoscope or funduscope, optical coherence tomography, or other imaging technology.

Macular deficiency testing may be performed in discrete tests on demand, or may be performed periodically and/or repeatedly over time. Repeated analysis may allow for the tracking of progressive macular deficiencies, such as age-related or other macular degeneration. Thus, macular deficiency diagnosis functions may be incorporated into a device worn only for ophthalmic diagnosis, or may be a part of a device worn regularly, such as for entertainment, work, or other purpose(s), so that examinations may be performed automatically at regular intervals and/or at various times of day, week, month, year, etc. In some embodiments, the wearer may be notified before an automatic examination is administered, such as by an alert sound and/or a visually displayed message. Results of macular deficiency testing may be evaluated in real time at the device for evaluation and/or diagnosis, or may be transmitted via the cloud or other network to be evaluated remotely. Remote evaluation and/or diagnosis of anomalies or other macular deficiency may be transmitted back to the device to enable the treatment or compensation methods described below. Unique characteristics of the wearer's eye may be recorded by the device and used for identity verification to ensure the security and privacy of the transmitted data. For example, the photo sensors 715 may image the iris and the light field processor 70 may perform pattern recognition to determine whether the identity of the wearer corresponds to the identity of the person to whom the test results correspond. The system may then display the test results only if the wearer is the person to whom the test results correspond.

The light field processor system may help compensate for macular degeneration by directly projecting light into the retina and specifically targeting healthy cells at the periphery of the macula. By changing where light is projected, the device can selectively target healthy cells and improve the user's quality of vision. In one or more embodiments, the light projecting source comprises an integral imaging display with LED light sources configured to project images into different portions of the user's eyes. The system may comprise other types of displays that can be configured to selectively project light onto different portions of the retina. This technology may be leveraged to selectively project pixels of an image to the healthy retinal cells, and reduce, minimize, or alter the nature of light projected to the damaged areas. For example, pixels projected to the anomaly may be magnified or made brighter. It should also be appreciated that this technique may also require modifications to the projected image data itself, and the light field processor may alter the nature of the image such that the user does not notice a significant difference when viewing the image.

The light field processor system may modify the wearer's view of light from the world. The system may detect the light entering the device in real time or near real time, and may modify portions of the light or project additional light to correct for the wearer's macular deficiency. For example, the system may use outward-facing cameras, such as the integral imaging camera 16, to image the world. The system may then project an image of the world to the wearer. The projected image data may be altered such that pixels may be selectively projected to healthy retinal cells, while pixels projected to anomalies may be reduced, minimized, magnified, brightened, or otherwise altered in magnification, intensity, hue, saturation, spatial frequency, or other quality. The system may also be used to generally darken bright rooms and/or brighten nighttime views for wearers with difficulty adjusting to changing light conditions due to macular degeneration.

The light field processor system may use outward facing camera(s) to provide alerts to a wearer. Alerts may be based on detection of hazardous conditions not visible to a wearer due to a macular deficiency. The system may determine the presence of an invisible hazard based on a correlation of the images from the outward facing camera(s) with known macular deficiency data of the wearer, such as location of anomalies on the retina. When a hazard in a blind spot is detected, such as an incoming object, a hole in the ground, or other condition, the system may alert the wearer. Alerts may include visual, audio, or tactile notifications. In cases of complete blindness, the system may be configured to detect the presence of a desired item (e.g., a chair, a table, a bed, etc.) and provide proximity information to the wearer, such as by audible notification.

Figure 19:
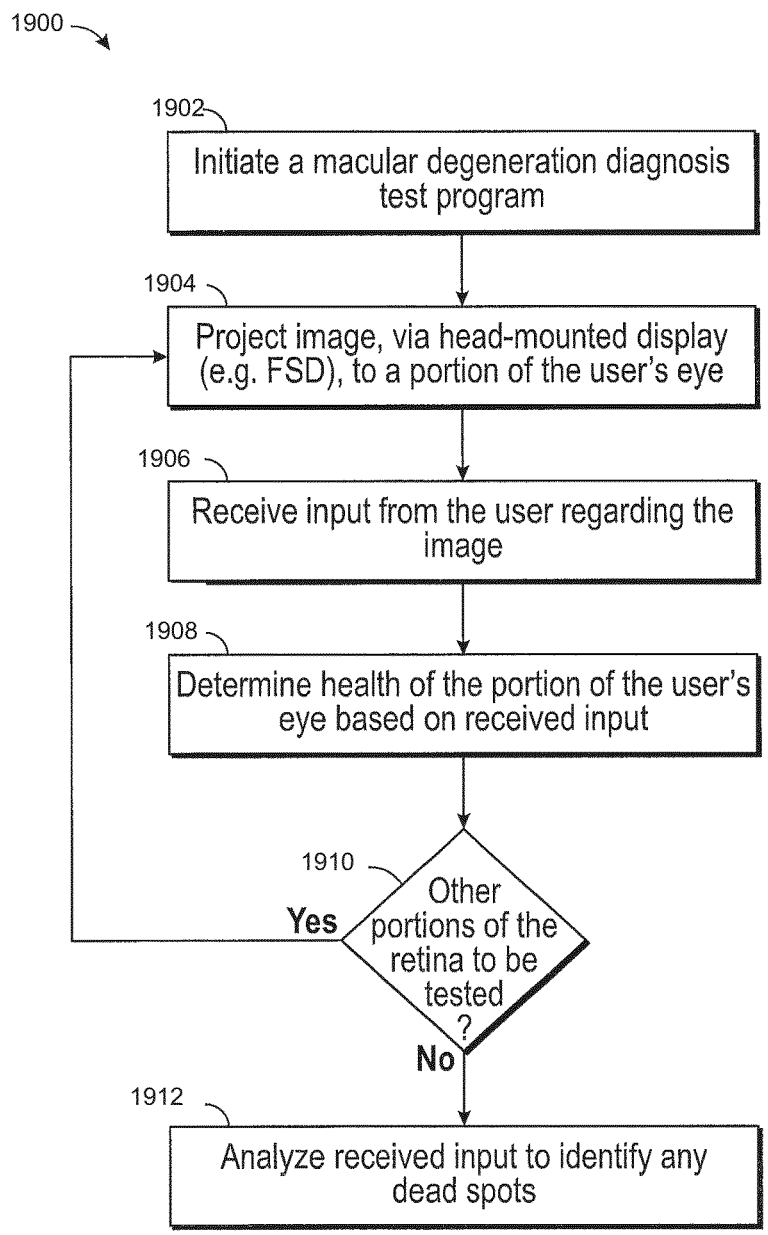
FIG. 19 shows a method for using the systems described herein to diagnose, detect, and/or identify any areas of macular degeneration.

In one or more embodiments, the light field processor system may diagnose or evaluate the user's eye anatomy to determine a location of macular degeneration. Referring now to FIG. 19, an example process flow 1900 to diagnose, detect, and/or identify any areas of macular degeneration is provided. At 1902, a macular degeneration diagnosis/evaluation program may be initiated. As was the case in many embodiments described above, the program may be pre-coded or downloaded into the light field processor system. At 1904, an image is projected, for example through one or more integral imaging displays 62, to a particular portion of the user's eye. For example, an image (e.g., a small dot, a small shape, etc.) is directed to the center of the user's eye (e.g., formed at the center of the retina).

At 1906, the system may receive input, through any type of user interface, regarding a quality of the image as seen by the user. For example, the user may be asked to rate the quality of the image from 1 to 10. Or, in another embodiment, the image may be projected with increasing or decreasing visual stimulus, and the user may have to identify when the image appears or disappears from the user's vision, is reduced in visual stimulus, and/or moves. In some embodiments, the system may detect the time required for the wearer to answer, as a wearer taking a long time to answer may be having difficulty seeing the stimulus. Similarly, many such techniques may be used, such as Pelli Robson or sine-wave grating tests. At 1908, based on the received user's input, the system may determine the health of that portion of the user's eye.

At 1910, the system may determine if other portions of the eye need to be similarly diagnosed and/or evaluated. If yes, steps 1904-1908 are repeated. After the various other portions of the eye have been similarly tested, at 1912, the results of the health of the various portions of the user's eye are analyzed, and any anomalies may be identified.

In one or more embodiments, the AR system behaves like a visuscope containing a small graticule target for the measurement of eccentric fixation. The light projecting source may project an image on the patient's retina, and the patient may be asked to look at the center of the target. The position of the foveal reflex relative to the center of the graticule target may indicate whether, and to the extent, the patient has eccentric fixation. Similarly, the direction and degree of eccentric fixation may be determined through the above process.

If it is determined that the user has one or more anomalies, the light field processor system may be configured to project a modified image to the user's eye such that the majority of the image is viewed through healthy peripheral retinal cells, and any pixels projected to the anomalies are adjusted. It should be appreciated that the image to be projected may need to be modified through predetermined algorithms such that the user views the image through the healthy cells, but does not notice a significant change in the image itself.

The following paragraphs describe various example embodiments of the devices, systems, and methods described herein.

A wearable ophthalmic device, comprising: a head-mounted light field display configured to generate a physical light field comprising a beam of light and to direct the beam of light to a selected sub-portion of the retina of a user's eye, thereby generating retinal reflex; a head-mounted photodetector array configured to receive the retinal reflex and to generate numerical image data; and a light field processor configured to control the light field display, to analyze the retinal reflex using the numerical image data from the photodetector array, and to determine the health of the selected sub-portion of the retina based on the analysis of the retinal reflex.

The device of the preceding paragraph, further comprising a user interface configured to receive input from the user regarding the health of the selected sub-portion of the retina.

The device of any of the preceding paragraphs, further comprising an outward facing head-mounted light field camera configured to receive light from the user's surroundings and to generate numerical light field image data, wherein the light field processor is configured to computationally modify the numerical light field image data based on the health of the retina so as to shift a selected portion of the light field image data such that it is incident on a healthy portion of the retina.

A method for using a wearable ophthalmic device, the method comprising: generating a physical light field comprising a beam of light and directing the beam of light to a selected sub-portion of the retina of a user's eye, thereby generating retinal reflex; receiving the retinal reflex and generating numerical image data using a head-mounted photodetector array; and controlling the light field display, analyzing the retinal reflex using the numerical image data from the photodetector array, and determining the health of the selected sub-portion of the retina based on the analysis of the retinal reflex using a light field processor.

The method of the preceding paragraph, further comprising receiving input from a user interface regarding the health of the selected sub-portion of the retina.

The method of any of the preceding paragraphs, further comprising: receiving light from the user's surroundings and generating numerical light field image data using an outward facing head-mounted light field camera; and computationally modifying the numerical light field image data based on the health of the retina so as to shift a selected portion of the light field image data such that it is incident on a healthy portion of the retina using the light field processor.

Re-Rendering Image Data from Outward Facing Camera

The various systems described herein may include one or more outward facing cameras to capture image information from the ambient environment, and this image information may subsequently be displayed as images and/or video presented to the wearer of the system. In some embodiments, the image information presented by the system to the wearer may be re-rendered to provide image information that is modified relative to image information originally captured by the camera. The modification may be performed by a processor (e.g., an image processor) that receives the image information captured by the cameras and processes the image information to include changes that are later communicated to light modulators that generate the displayed images and/or videos. In some embodiments, the wearer's view of the world and particular features in that view may be modified as desired for diagnostic or therapeutic purposes.

With reference to FIG. 5, the head-mounted health system may include one or more outward facing cameras 16 to image the world around the wearer. The system may process the image information (e.g., image(s) and/or video) captured by the camera(s) 16 to re-render the image information for display to the wearer. In some embodiments, the device may project light from the display device 108 to the wearer's eye so as to project a re-rendered image of the world to the wearer. The re-rendering techniques described herein can be applied to light field image information collected from light field cameras, or to any other type of image information collected by any other type of camera. Similarly, the re-rendered image information can be displayed by a light field display device (if the re-rendered image information consists of light field image data) or any other type of display device.

In some embodiments, in the re-rendering step, the processor (e.g., the light field processor 70) may be configured to selectively modify properties of the image that will be displayed to the wearer. For example, the processor may be configured to selectively alter portions of the image based on a distribution of healthy and unhealthy cells in a retina of the wearer so that those portions are projected to healthy retinal cells, while portions of the image projected to unhealthy retinal cells may be reduced, minimized, magnified, brightened, or otherwise altered in magnification, intensity, hue, saturation, spatial frequency, or other quality. Similarly, any desired portion of the image may be modified in magnification, intensity, hue, saturation, spatial frequency, or any other quality as required to mitigate and/or compensate for any known ophthalmic condition of the wearer. The wavefront of the image may also be modified and/or reshaped so as to mitigate focus-related conditions in some embodiments. In other examples, the system may also be used to generally darken bright rooms and/or brighten nighttime views for wearers with difficulty adjusting to changing light conditions, by, for example, substituting all or portions of the user's view of the world with re-rendered content, which may present a darker or lighter view of the world, as desired. The image data can be darkened or lightened using known image processing techniques. In another example, the system may modify or shift colors to enhance the vision of the wearer, including colorblind wearers. It will be appreciated that the system may include an augmented reality display or a virtual reality display, and that re-rendering image information as disclosed herein may be applied in displaying content on either type of display.

With continued reference to FIG. 5, in some embodiments, the health system may have one or more forward and outward facing cameras 16 that image the world around (e.g., in front of) the wearer. The system may be configured to determine various characteristics of the image, such as the intensity, hue, saturation, and/or spatial frequency of regions of the image. The system may process, and reproduce to the wearer, via the display device 108, an image of the world based on the information captured by the outward facing cameras 16, with some modifications of brightness, magnification, color, wavefront, and/or other parameters, as described above. In some embodiments, the display device may project only a partial image to the eye of the wearer, with the partial image augmenting light passing through the display (e.g., as in some augmented reality embodiments) to the eye of the wearer to produce the desired modification. For example, the augmented reality system may shift the color of portions of the image based on a known color detection deficiency of the wearer. In another example, the augmented reality system may enhance the difference in brightness between two or more portions of the image based on a known contrast sensitivity deficiency of the wearer.

The following paragraphs describe various specific examples of re-rendering techniques which can be applied by a processor to image information collected using the systems described herein.

Dimming is a re-rendering operation which can be performed on image information collected by an outward facing camera prior to being displayed to a wearer of the system. For example, all or a portion of the field of view of the image information can be computationally dimmed. Or in other words, the brightness of the image information can be computationally reduced by a processor prior to displaying the captured image information to the user. The computational dimming of the captured image information can be performed manually in response to a user input. Alternatively, the computational dimming of the captured image information can be performed automatically based on the ambient lighting conditions (as detected by the camera 16 or another sensor). Dimming of the image information can be beneficial in many different scenarios. For example, bright light can be a major factor in triggering migraine headaches or in causing sensory overload in people who are prone to seizures, or in people who suffer from autism or social anxiety. Thus, dimming of the collected image information prior to displaying it to the user can help prevent adverse responses to bright light for people who suffer from these and other conditions.

In some embodiments, the entire field of view encompassed by the image information is dimmed. In other embodiments, dimming can be selectively applied to different portions of the field of view. For example, in some embodiments, eye tracking technology (provided using, for example, the systems and techniques described herein) can be used to determine where in the field of view the user is fixating and the image information can be selectively dimmed in the portion of the field of view corresponding to that point. Conversely, the image information could be selectively dimmed in portions of the field of view other than where the user is fixating. This can be done to, for example, provide emphasis for the portion of the field of view of the image information that the user is actively viewing. While selective dimming of a portion of the field of view of the image information can be controlled by eye tracking technology based on where the user is looking, it can alternatively be controlled based on gestures or other user inputs as well.

Conversely to dimming, increasing brightness is another re-rendering operation which can be performed on image information collected by an outward facing camera prior to being displayed to a wearer of the system. The brightness of the image information can be computationally increased by a processor. Alternatively, or additionally, the brightness of the image information can be increased by increasing the sensitivity of the sensor used to capture the image information or by illuminating the scene in the user's field of view with visible or infrared light and then capturing the reflection of that light from the scene as part of the image information.

In some embodiments, the brightness of the entire field of view encompassed by the image information is increased by the processor. In other embodiments, the brightness can be selectively increased to different portions of the field of view. For example, using eye tracking technology, the brightness of the portion of the field of view where the user is looking can be selectively increased. The converse is also possible where the brightness of the portion of the field of view other than where the user is looking can be selectively increased. The portion of the field of view that is selectively brightened can also be controlled in other ways, such as by user gestures or other control inputs.

Enhancing the brightness of the image information can be used in a number of different ways. For example, enhanced brightness of the image information can be used to help those who suffer from seasonal affective disorder. In some embodiments, the systems described herein can be used in conjunction with, and be communicatively coupled to, other sensors which detect a user's physiological parameters such as body temperature, heart rate, blood pressure, movement, etc. The processor can monitor this sensory input and automatically enhance brightness of the image information based on the user's mood, productivity, attentiveness, etc., which can be surmised from the sensory input. In addition, flickering brightness has been shown to increase blood flow and ocular vasculature. Thus, the processor can cause the brightness of the image information to flicker at a selected frequency so as to stimulate blood flow in the user's eyes.

Blurring is another re-rendering operation which can be performed on image information collected by an outward facing camera prior to being displayed to a wearer of the system. Blurring can be performed by a processor computationally by, for example, applying a low pass digital filter to all or a portion of the captured image information. The low pass filter can be, for example, a Gaussian blur filter. Application of a blurring filter can improve image quality by reducing image noise. In addition, a reduction in noise combined with a softer image and blended details and colors could reduce the potential for sensory overload which could benefit people who suffer from autism and/or social anxiety. Blurring can be applied to the entire field of view of the image information or just to a portion of it. If blurring is selectively applied to only a portion of the field of view of the image information, then that portion can be chosen based on where the user is fixating. For example, eye tracking technology can be used to determine where the user is looking and blurring can be applied to that portion of the field of view or to the portion of the field of view other than where the user is looking. Alternatively, a user can select a portion of the field of view to be blurred with a gesture or other control input.

Conversely to blurring, sharpening is another re-rendering operation which can be performed on image information collected by an outward facing camera prior to being displayed to a wearer of the system. Once again, the sharpening operation can be applied to the entire field of view of the image information or just a portion of it. If the sharpening operation is applied only to a portion of the field of view of the image information, that portion can be chosen using eye tracking technology based on the location where the user is looking. For example, the sharpening operation can be applied to the portion of the field of view where the user is looking or to the portion of the field of view other than where the user is looking. Or a gesture or other control input can also be used to select a portion of the field of view of the image information for sharpening.

Edge detection and/or edge enhancement are still other re-rendering operations which can be performed on image information collected by an outward facing camera prior to being displayed to a wearer of the system. Once again, these operations can be computationally performed to the entire field of view of the image information or just to a portion of it.

Edge detection and/or edge enhancement operations can be used in conjunction with object or feature recognition algorithms, which can also be applied to the image information as re-rendering operations. These types of algorithms can recognize objects within the field of view shown by the image information. The processor can then insert an augmented reality tag or label for any recognized object. For example, the tag or label can be inserted into the image information and superimposed over, or provided around or near, the recognized object. The tag or label can provide any desired type of information about the object. In addition, a processor may apply augmented reality features which highlight a recognized object within the field of view of the image information. For example, if an object is recognized then its edges can be bolded. Alternatively, any other augmented reality feature which would tend to draw the user's attention can be added to the object.

Object recognition algorithms can also be used to identify objects which trigger a physical or emotional reaction when viewed by the user. For example, the systems described herein can be used in conjunction with, and be communicatively coupled to, other sensors which detect a user's physiological parameters such as body temperature, heart rate, blood pressure, etc. The output of the sensors can be monitored to determine when the user has a physical or emotional response to something he or she is viewing. Object recognition and eye tracking technology can be used to determine whether the user was viewing a specific object when the physical or emotional response occurred. The system can then output data indicative of objects, times, image data, etc. which triggered a response and/or provide a notification to the user. This type of functionality could be beneficial to many different types of people. For example it could help determine what people who suffer from Alzheimer's disease struggle with in day-to-day life. Or it could help people who suffer from, for example, obsessive-compulsive disorder or post-traumatic stress disorder to determine what triggers a reaction.

In some embodiments, if an object is recognized by the object recognition algorithm, the processor could replace or alter the recognized object with an augmented reality object or feature. For example, if an autistic user struggles in social environments, then recognized people within the field of view of the captured image information could be replaced with animated augmented reality characters. This can help an autistic user feel more comfortable in interacting in the social environment. In addition, the processor can implement a type of exposure therapy in which the animations become less drastic overtime, thereby allowing the user to become more comfortable with real life people over time.

Color alterations are additional re-rendering operations which can be performed on captured image information before it is displayed to the user. A variety of such computational color alterations are possible: a selected color in the image information can be mapped to another color; white balance can be altered; color temperature can be altered; etc. In the case of users who suffer from any type of color blindness, the processor can alter colors in the image information in such a way so as to improve contrast for the user. For example, the system can computationally attenuate two colors that a person who suffers from color blindness cannot see. By attenuating the stimulating colors and reducing or removing the maximum spectral overlap, the distinction between the signals stimulated in the cone cells can be improved.

In addition, blue light exposure has been shown to improve decision-making. Thus, in some embodiments, a blue tint can be added computationally to the image information so as to take advantage of this effect. As another example, red light exposure can affect the oxygen generation of mitochondria on the retina, which can help reduce the effects of macular degeneration. Thus, in some embodiments, a red tint can be added computationally to the image information so as to take advantage of this effect.

Additional re-rendering operations which can be applied to the captured image information include zooming in, zooming out, and shifting the image information laterally. These operations can be controlled in a variety of ways, including by gestures or other user inputs or based on where the user is looking (as indicated by eye tracking technology). When computationally magnifying the image information, a weighted average of pixels can be calculated using, for example, a Gaussian function to be able to scale up an image without losing much of its detail. Magnification and lateral shifting of the image information can be beneficial for many people, including those who suffer from macular degeneration. For example, a location within the field of view of the image information where the user is looking can be magnified to reduce the relative impact of the macular dead spot (by increasing the virtual size of the viewing target) and/or shifted so that it appears on healthy retina cells in the user's eye. In addition to zooming in, the system can also zoom out. For example, the outward facing camera(s) can be used to capture image information from a larger field of view which extends beyond the wearer's normal field of view and then the system can computationally compress the image information from this larger field of view to fit within the user's normal field of view.

In addition, lateral shifting of the field of view of the image information can help those who suffer from nystagmus, which causes involuntary movements of the eyes. For example, eye tracking technology can be used to monitor the eye movements of a nystagmus patient and the field of view of the image information can be shifted in sync with the involuntary eye movements so as to help stabilize the field of view for the user. Rather than moving the image information in sync with the involuntary eye movements, the image information may alternatively be moved slightly out of sync (e.g., at a slightly slower frequencies) for certain durations of time to slow the involuntary eye movements as a form of therapy. A similar technique can be used to help those who suffer from oscillopsia, which is a visual defect in which the field of view of the patient oscillates. The processor can cause the field of view of the image information to oscillate in sync with the eyes of the user so as to help stabilize his or her vision. In addition, therapy can be provided by slowing the oscillation of the field of view of the image information over time to help train the user's eyes so as to reduce their amount of oscillation.

Yet another re-rendering operation is to computationally increase the resolution of the image information captured by the system's outward facing camera(s). This can be accomplished using known upsampling techniques. The higher resolution image information can then be displayed to the user. By digitally increasing the resolution of the image information, the wearer of the system can experience a perceived increase in visual acuity.

In some embodiments, the re-rendering operations discussed thus far may be applied in real time to image information captured by an outward facing camera for display to the user. However, an additional operation which can be performed is playback of non-real-time image information. For example, image information collected at an earlier point in time (e.g., seconds, minutes, hours, days, etc. earlier) can be played back to the user. In such cases, the system may include memory which records captured image information on a continuing basis such that image information from any desired prior point in time can be selected for playback on command. The prior image information can be played back in normal time, or it can be played back slower or faster than normal speed. The user can control this functionality with gestures or other control inputs.

Any of the foregoing re-rendering operations can be performed automatically or based on user input. The systems described herein can include various input controls, such as interactive elements or menus that the user can navigate in order to control settings, preferences, functions, etc.; eye tracking; gesture control; head pose; voice; etc. In addition, these functions can also be performed by using a fundus camera, a diode laser, an image sensor, an infrared charge-coupled device (CCD) camera and a high-resolution digital CCD camera, all of which could be attachments on the device.

The following paragraphs describe various example embodiments of the devices, systems, and methods described herein.

A wearable ophthalmic device, comprising: an outward facing head-mounted light field camera configured to receive light from a user's surroundings and to generate numerical light field image data; a light field processor configured to computationally modify the numerical light field image data to generate modified numerical light field image data; and a head-mounted light field display configured to generate a physical light field corresponding to the modified numerical light field image data.

The device of the preceding paragraph, wherein the light field processor is configured to computationally dim at least a portion of the numerical light field image data.

The device of any of the preceding paragraphs, wherein the light field processor is configured to computationally brighten at least a portion of the numerical light field image data.

The device of the preceding paragraph, wherein the light field processor is configured to control brightness based on an indication of the user's mood.

The device of any of the preceding paragraphs, wherein the light field processor is configured to cause the brightness to flicker to enhance blood flow in the user's eye.

The device of any of the preceding paragraphs, wherein the light field processor is configured to computationally magnify at least a portion of the numerical light field image data.

The device of any of the preceding paragraphs, wherein the light field processor is configured to computationally blur at least a portion of the numerical light field image data.

The device of any of the preceding paragraphs, wherein the light field processor is configured to computationally detect or enhance edges in the numerical light field image data.

The device of any of the preceding paragraphs, wherein the light field processor is configured to cause the light field display to play back a physical light field corresponding to the numerical light field image data from a previous moment in time.

The device of the preceding paragraph, wherein the light field processor is configured to playback the light field image data faster or slower than normal speed.

The device of any of the preceding paragraphs, wherein the light field processor is configured to detect an object in the numerical light field image data captured by the light field camera.

The device of the preceding paragraph, wherein the light field processor is configured replace or modify the detected object with an augmented reality feature.

The device of any of the preceding paragraphs, wherein the light field processor is configured to determine whether the detected object elicits a detectable physical or emotional response from the user.

The device of any of the preceding paragraphs, wherein the light field processor is configured to computationally alter a color in the numerical light field image data.

The device of the preceding paragraph, wherein the light field processor is configured to computationally increase the color blue in the numerical light field image data to enhance a user's decision making.

The device of any of the preceding paragraphs, wherein the light field processor is configured to computationally increase the color red in the numerical light field image data to enhance the health of the retina.

A method of using a wearable ophthalmic device, the method comprising: receiving light from a user's surroundings and generating numerical light field image data using an outward facing head-mounted light field camera; computationally modifying the numerical light field image data to generate modified numerical light field image data using a light field processor; and generating a physical light field corresponding to the modified numerical light field image data using a head-mounted light field display.

The method of the preceding paragraph, further comprising computationally dimming at least a portion of the numerical light field image data.

The method of any of the preceding paragraphs, further comprising computationally brightening at least a portion of the numerical light field image data.

The method of the preceding paragraph, further comprising controlling brightness based on an indication of the user's mood.

The method of any of the preceding paragraphs, further comprising causing the brightness to flicker to enhance blood flow in the user's eye.

The method of any of the preceding paragraphs, further comprising computationally magnifying at least a portion of the numerical light field image data.

The method of any of the preceding paragraphs, further comprising computationally blurring at least a portion of the numerical light field image data.

The method of any of the preceding paragraphs, further comprising computationally detecting or enhancing edges in the numerical light field image data.

The method of any of the preceding paragraphs, further comprising causing the light field display to play back a physical light field corresponding to the numerical light field image data from a previous moment in time.

The method of the preceding paragraph, further comprising playing back the light field image data faster or slower than normal speed.

The method of any of the preceding paragraphs, further comprising detecting an object in the numerical light field image data captured by the light field camera.

The method of the preceding paragraph, further comprising replacing or modifying the detected object with an augmented reality feature.

The method of any of the preceding paragraphs, further comprising determining whether the detected object elicits a detectable physical or emotional response from the user.

The method of any of the preceding paragraphs, further comprising computationally altering a color in the numerical light field image data.

The method of the preceding paragraph, further comprising computationally increasing the color blue in the numerical light field image data to enhance a user's decision making.

The method of any of the preceding paragraphs, further comprising computationally increasing the color red in the numerical light field image data to enhance the health of the retina.

Computer Vision and Sensor Based Detection of Triggering Events

In some of the embodiments described herein, the light field processor system starts, ends, modifies, etc. a diagnosis or treatment protocol based on triggering events, such as a condition or emotional state of the user, or based on an event or detected condition in the user's environment. Other triggering events may also be applicable. In some cases, such triggering events can be detected by a computer vision system.

A triggering event can be detected using a variety of techniques. A triggering event may be determined based on reactions of the user. For example, the light field processor system can analyze data acquired by the inward-facing imaging system or by a physiological sensor. The light field processor system can use the data to determine the user's emotional state. The light field processor system can detect the presence of a triggering event by determining whether the user is in a certain emotional state (such as angry, scared, uncomfortable, etc.). As an example, the light field processor system can analyze the user's pupil dilation, heart rate, respiration rate, or perspiration rate to determine the user's emotional state.

The triggering event can also be detected using computer vision techniques. For example, the light field processor system can analyze the images acquired by the outward facing imaging system to perform scene reconstruction, event detection, video tracking, object recognition, object pose estimation, learning, indexing, motion estimation, or image restoration, etc.

One or more computer vision algorithms may be used to perform these tasks. Non-limiting examples of computer vision algorithms include: Scale-invariant feature transform (SIFT), speeded up robust features (SURF), oriented FAST and rotated BRIEF (ORB), binary robust invariant scalable keypoints (BRISK), fast retina keypoint (FREAK), Viola-Jones algorithm, Eigenfaces approach, Lucas-Kanade algorithm, Horn-Schunk algorithm, Mean-shift algorithm, visual simultaneous location and mapping (vSLAM) techniques, a sequential Bayesian estimator (e.g., Kalman filter, extended Kalman filter, etc.), bundle adjustment, Adaptive thresholding (and other thresholding techniques), Iterative Closest Point (ICP), Semi Global Matching (SGM), Semi Global Block Matching (SGBM), Feature Point Histograms, various machine learning algorithms (such as e.g., support vector machine, k-nearest neighbors algorithm, Naive Bayes, neural network (including convolutional or deep neural networks), or other supervised/unsupervised models, etc.), and so forth.

One or more of these computer vision techniques can also be used together with data acquired from other environmental sensors (such as, e.g., microphone) to detect the presence of the triggering event.

The triggering event may be detected based on one or more criteria. These criteria may be defined by a user. The presence of the triggering event may also be indicated by a user's interactions. For example, the user may make a certain pose (e.g., a hand gesture or a body pose) or actuate a user input device indicating the presence of the triggering event.

Additionally or alternatively, the criteria may also be learned based on the user's behaviors. For example, the light field processor system can monitor when a user turns off the light field processor system. The light field processor system can observe that the user often turns off the light field processor system in response to a certain type of virtual content (e.g., certain types of scenes in a movie). The light field processor system may accordingly learn the user's behavior and predict a triggering event based on the user's behavior. As another example, the light field processor system can associate the user's emotional state based on the user's previous interactions with virtual content. The light field processor system can use this association to predict whether a triggering event is present when the user is interacting with a virtual object.

Machine Learning of Triggering Events

A variety of machine learning algorithms can be used to learn triggering events. Once trained, the machine learning algorithm can be stored by the light field processor system. Some examples of machine learning algorithms can include supervised or non-supervised machine learning algorithms, including regression algorithms (such as, for example, Ordinary Least Squares Regression), instance-based algorithms (such as, for example, Learning Vector Quantization), decision tree algorithms (such as, for example, classification and regression trees), Bayesian algorithms (such as, for example, Naive Bayes), clustering algorithms (such as, for example, k-means clustering), association rule learning algorithms (such as, for example, a-priori algorithms), artificial neural network algorithms (such as, for example, Perceptron), deep learning algorithms (such as, for example, Deep Boltzmann Machine, or deep neural network), dimensionality reduction algorithms (such as, for example, Principal Component Analysis), ensemble algorithms (such as, for example, Stacked Generalization), and/or other machine learning algorithms. In some embodiments, individual models can be customized for individual data sets. For example, the wearable device can generate or store a base model. The base model may be used as a starting point to generate additional models specific to a data type (e.g., a particular user), a data set (e.g., a set of additional images obtained), conditional situations, or other variations. In some embodiments, the wearable light field processor system can be configured to utilize a plurality of techniques to generate models for analysis of the aggregated data. Other techniques may include using pre-defined thresholds or data values.

The criteria can include a threshold condition. If the analysis of the data acquired by the environmental sensor indicates that the threshold condition is passed, the light field processor system may detect the presence of the triggering event. The threshold condition may involve a quantitative and/or qualitative measure. For example, the threshold condition can include a score or a percentage associated with the likelihood of the triggering event is occurring. The light field processor system can compare the score calculated from the environmental sensor's data with the threshold score. If the score is higher than the threshold level, the light field processor system may detect the presence of the triggering event. In other embodiments, the light field processor system can signal the presence of the triggering event if the score is lower than the threshold.

The threshold condition may also include letter grades such as such as "A", "B", "C", "D", and so on. Each grade may represent a severity of the situation. For example, "A" may be the most severe while "D" may be least severe. When the light field processor system determines that an event in the user's environment is severe enough (as compared to the threshold condition), light field processor system may indicate the presence of a triggering event and take action (e.g., starting, ending, or altering a diagnostic or treatment protocol).

The threshold condition may be determined based on objects (or people) in the user's physical environment. For example, a threshold condition may be determined based on the user's heart rate. If the user's heart rate exceeds a threshold number (e.g., a certain number of beats per minute), the light field processor system may signal the presence of the triggering event. As yet another example, the threshold condition may be determined based on the presence of certain objects in the user's environment.

The threshold condition may also be determined based on the virtual content, or based on the user's interaction with the virtual content. For example, the threshold condition may be the duration of the user watching a piece of virtual content.

CONCLUSION

As discussed herein, the disclosed head-mounted displays may advantageously form part of a user-wearable diagnostic or health system, which may be used for performing health-related diagnostics, monitoring, and therapeutics on the user. In some embodiments, the health-related diagnostics, monitoring, and therapeutics may include ophthalmic diagnostic analyses, monitoring, and therapies. In view of the disclosure herein, however, it will be appreciated that the diagnostic or health system is not limited to ophthalmic applications and may be applied generally to health-related diagnostics, monitoring, and therapeutics.

It will be appreciated that each of the processes, methods, and algorithms described herein and/or depicted in the figures may be embodied in, and fully or partially automated by, code modules executed by one or more physical computing systems, hardware computer processors, application-specific circuitry, and/or electronic hardware configured to execute specific and particular computer instructions. For example, computing systems can include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some embodiments, particular operations and methods may be performed by circuitry that is specific to a given function.

Further, certain embodiments of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. In some embodiments, the non-transitory computer-readable medium may be part of one or more of the light field processor 70, the local processing and data module 70, the remote processing module 72, and remote data repository 74. The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities can be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto can be performed in other sequences that are appropriate, for example, in serial, in parallel, or in some other manner. Tasks or events may be added to or removed from the disclosed example embodiments. Moreover, the separation of various system components in the embodiments described herein is for illustrative purposes and should not be understood as requiring such separation in all embodiments. It should be understood that the described program components, methods, and systems can generally be integrated together in a single computer product or packaged into multiple computer products.

In the foregoing specification, the invention has been described with reference to specific embodiments thereof. It will, however, be evident that various modifications and changes may be made thereto without departing from the broader spirit and scope of the invention. For example, the projected light and images for embodiments disclosed herein may be provided by various types of displays, including liquid crystal displays, micromirror-based displays (e.g., DLP displays), scanning fiber displays (FSDs), and OLED displays.

The specification and drawings are, accordingly, to be regarded in an illustrative rather than restrictive sense.

Indeed, it will be appreciated that the systems and methods of the disclosure each have several innovative aspects, no single one of which is solely responsible or required for the desirable attributes disclosed herein. The various features and processes described above may be used independently of one another, or may be combined in various ways. All possible combinations and sub-combinations fall within the scope of this disclosure.

Certain features that are described in this specification in the context of separate embodiments also can be implemented in combination in a single embodiment. Conversely, various features that are described in the context of a single embodiment also can be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination. No single feature or group of features is necessary or indispensable to each and every embodiment.

Headings are used throughout this application as an organizational aid for the reader. These headings may group together examples of methods, apparatuses, and structures that may generally relate to a particular topic noted in the headings. It will be appreciated, however, that while the various features discussed under the heading may relate to a particular topic, the headings should not be understood to indicate that the features discussed under a given heading are limited in applicability only to the topic or topics that listed in the heading.

Indeed, as shown in various figures (e.g., FIG. 5), structures for various health analyses and/or therapies may coexist in the same health system. Moreover, as disclosed herein, the same feature may be applied to facilitate multiple health analyses and/or therapies. For example, structures used for delivering medication may also be utilized for various diagnostics, as disclosed herein. Consequently, health systems according to some embodiments may include various combinations of the structural features disclosed herein, including combinations of features disclosed under different headings. In addition, the health system may be configured to perform various combinations of the health analyses and therapies disclosed herein, including those disclosed under different headings.

It will be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted can be incorporated in the example methods and processes that are schematically illustrated. For example, one or more additional operations can be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products. Additionally, other embodiments are within the scope of the following claims. In some cases, the actions recited in the claims can be performed in a different order and still achieve desirable results.

Accordingly, the claims are not intended to be limited to the embodiments shown herein, but are to be accorded the widest scope consistent with this disclosure, the principles and the novel features disclosed herein.

What is claimed is:

1. A wearable ophthalmic device, comprising:
   a head-mounted light field display configured to generate a physical light field comprising a beam of light and to direct the beam of light into a user's eye, thereby producing a retinal reflex;
   a head-mounted photodetector array configured to receive the retinal reflex and to generate numerical image data; and
   a light field processor configured to control the light field display, to analyze the retinal reflex using the numerical image data, and to determine an optical prescription for the user's eye based on the analysis of the retinal reflex.

2. The device of claim 1, wherein the light field processor is further configured to computationally introduce an amount of positive or negative optical power to the beam of light based on the analysis of the numerical image data.

3. The device of claim 1, wherein the photodetector array is part of a light field camera and the numerical image data comprises numerical light field image data.

4. The device of claim 1, wherein the light field display comprises an integral imaging display.

5. The device of claim 1, wherein the photodetector array is integrated with the light field display.

6. The device of claim 1, further comprising a disc with at least two pinholes, the disc being positioned in front of the eye such that the beam of light passes through the pinholes.

7. The device of claim 1, wherein the light field processor is configured to analyze the retinal reflex to determine the focus of the light on the retina.

8. The device of claim 1, further comprising an outward facing head-mounted light field camera configured to receive light from a user's surroundings and to generate numerical light field image data, wherein the light field processor is configured to computationally modify the numerical light field image data based on the analysis of the retinal reflex.

9. A method of using a wearable ophthalmic device, the method comprising:
   generating a physical light field comprising a beam of light and directing the beam of light into a user's eye using a head-mounted light field display, thereby producing a retinal reflex;
   receiving the retinal reflex and generating numerical image data using a head-mounted photodetector array; and
   controlling the light field display, analyzing the retinal reflex using the numerical image data, and determining an optical prescription for the user's eye based on the analysis of the retinal reflex using a light field processor.

10. The method of claim 9, further comprising computationally introducing an amount of positive or negative optical power to the beam of light based on the analysis of the numerical image data using the light field processor.

11. The method of claim 9, wherein the photodetector array is part of a light field camera and the numerical image data comprises numerical light field image data.

12. The method of claim 9, wherein the light field display comprises an integral imaging display.

13. The method of claim 9, wherein the photodetector array is integrated with the light field display.

14. The method of claim 9, further comprising transmitting the beam of light through a disc with at least two pinholes, the disc being positioned in front of the eye.

15. The method of claim 9, further comprising analyzing the retinal reflex to determine the focus of the light on the retina using the light field processor.

16. The method of claim 9, further comprising:
   receiving light from a user's surroundings and generating numerical light field image data using an outward facing head-mounted light field camera; and
   computationally modifying the numerical light field image data based on the analysis of the retinal reflex.

* * * * *